US009783574B2

(12) United States Patent
Pemberton et al.

(10) Patent No.: US 9,783,574 B2
(45) Date of Patent: Oct. 10, 2017

(54) CARDIOVASCULAR THERAPEUTICS

(75) Inventors: Christopher Joseph Pemberton, Christchurch (NZ); Arthur Mark Richards, Christchurch (NZ); Christopher John Charles, Christchurch (NZ); Maithri Siriwardena, Rangitikei (NZ)

(73) Assignee: Otago Innovation Limited, North Dunedin (NZ)

( * ) Notice: Subject to any disclaimer, the term of this patent is extended or adjusted under 35 U.S.C. 154(b) by 412 days.

(21) Appl. No.: 13/589,082

(22) Filed: Aug. 17, 2012

(65) Prior Publication Data

US 2013/0072431 A1    Mar. 21, 2013

Related U.S. Application Data

(60) Provisional application No. 61/525,140, filed on Aug. 18, 2011.

(51) Int. Cl.
| C07K 7/06 | (2006.01) |
| C07K 5/083 | (2006.01) |
| C07K 5/103 | (2006.01) |
| C07K 5/062 | (2006.01) |
| A61K 38/08 | (2006.01) |
| A61K 38/22 | (2006.01) |

(52) U.S. Cl.
CPC ............ *C07K 7/06* (2013.01); *C07K 5/06043* (2013.01); *C07K 5/0808* (2013.01); *C07K 5/101* (2013.01); *A61K 38/08* (2013.01); *A61K 38/2242* (2013.01)

(58) Field of Classification Search
None
See application file for complete search history.

(56) References Cited

U.S. PATENT DOCUMENTS

| 3,155,590 A | 11/1964 | Miller et al. |
| 3,391,416 A | 7/1968 | Riggles, Jr. |
| 3,488,418 A | 1/1970 | Holliday et al. |
| 5,252,714 A | 10/1993 | Harris et al. |
| 6,120,789 A | 9/2000 | Dunn |
| 6,193,996 B1 | 2/2001 | Effing et al. |
| 6,262,121 B1 | 7/2001 | Kawaji et al. |
| 6,309,380 B1 | 10/2001 | Larson et al. |
| 6,362,190 B2 | 3/2002 | Shafer et al. |
| 6,410,041 B1 | 6/2002 | Lewis et al. |

FOREIGN PATENT DOCUMENTS

| WO | 01/07617 A1 | 2/2001 |
| WO | 2005/052593 A1 | 6/2005 |
| WO | WO 2005072055 A2 * | 8/2005 |
| WO | 2008/030122 A1 | 3/2008 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Agrawal (Ed.), Protocols for Oligonucleotides and Analogs, Synthesis and Properties, 1993, vol. 20, Humana Press Inc., NJ (Table of Contents).
Altschul, J. Mol. Evol., 1993, 290-300, 36(3).
Altschul et al., J. Mol. Biol., 1990, 403-410, 215(3).
Ansel et al. (Eds.), Pharmaceutical Dosage Forms and Drug Delivery Systems, 7th Ed., 1999, Lippincott-Williams & Wilkins, Philadelphia, PA (Table of Contents).
Arshady., Polymer Eng. Sci., 1990, 915-924, 30(15).
Aulton (Ed.), Pharmaceutics: The Science of Dosage Form Design, 2nd Ed., 2002, Churchill Livingstone, Edinburgh, NY (Table of Contents).
Bodmeier et al., J. Pharm. Sci., 1990, 32-36, 79(1).
Buckton et al., Int. J. Pharm., 1991, 153-158, 74(2-3).
Chafi et al., Int. J. Pharm., 1992, 265-274, 67(3).
Coligan et al.(Eds.), Current Protocols in Immunology vol. 1, 1991, Wiley-Interscience, New York, NY, USA (Table of Contents Only).
De Arnab, Application of Peptide-Badsed Prodrug Chemistry in Drug Development, 2013, Springer (Table of Contents).
Douglas et al., CRC Crit. Rev. Ther. Drug Carrier Syst., 1987, 233-261, 3.
Fites et al., J. Pharm. Sci., 1970, 610-613, 59(5).
Freshney (Ed.), Culture of Animal Cells, 2nd Ed., 1987, Alan R. Liss, Inc., NY (Table of Contents).
Gait (Ed.), Oligonucleotide Synthesis: A Practical Approach, 1984, IPL Press, Oxford, Washington DC (Table of Contents).
Harlow et al. (Ed.), Antibodies, A Laboratory Manual, 1988, Cold Spring Harbor Press, New York (Table of Contents).
Harlow et al. (Ed.), Using Antibodies: A Laboratory Manual, 1999, Cold Spring Harbor Publications, NY (Table of Contents).
Henikoff et al., Proc. Natl. Acad. Sci. USA, 1992, 10915-10919, 89(22).
Hermanson (Ed.), Bioconjugate Techniques, 1996, Academic Press, San Diego, CA (Table of Contents).
Higuchi, J. Pharm. Sci., 1963, 1145-1149, 52(12).
Hunt et al., Biochem. Biophys. Res. Commun., 1995, 1175-1183, 214(3).
Karlin et al., Proc. Natl. Acad. Sci. USA, 1993, 5873-5787, 90(12).
Kibbe, Handbook of Pharmaceutical Excipients, 3rd Ed., 2005, American Pharmaceutical Association, WA (Table of Contents).
Laghoueg et al., Int. J. Pharm., 1989, 133-139, 50(2).
McMurray et al., Heart failure, Lancet, 2005, 1877-1889, 365(9474).
Miller et al. (Eds.), Gene Transfer Vectors for Mammalian Cells, 1987, Cold Springs Harbor, NY (Table of Contents).
Mullis et al. (Eds.), The Polymerase Chain Reaction, 1994, Birkhauser (Table of Contents).
Omland et al., Heart, 1996, 232-237, 76(3).
Oppenheim, Int. J. Pharm., 1981, 217-234, 8(3).
Osborne et al., Pharm. Tech., 1997, 58-66, 21(11).
Pemberton et al., Am. J. Physiol. Heart Circ. Physiol., 2004, H1522-H1529, 287.

(Continued)

*Primary Examiner* — Brian J Gangle
*Assistant Examiner* — Andrea McCollum
(74) *Attorney, Agent, or Firm* — Carol L. Francis; Bozicevic, Field & Francis LLP

(57) ABSTRACT

Compounds and compositions comprising a B-type natriuretic signal peptide fragment agent, and methods of use thereof, are provided for the treatment or prevention of cardiovascular diseases, disorders, and conditions.

14 Claims, 14 Drawing Sheets

(56) References Cited

OTHER PUBLICATIONS

Piuhola et al., Clin. Sci. (Lond.), 2008, 293-304, 114(4).
Potter et al., Endocr. Rev., 2006, 47-72, 27(1).
Saito et al., J. Agric. Food Chem., 2003, 3668-3674, 51(12).
Sambrook et al. (Eds.), Molecular Cloning: A Laboratory Manual, 2nd Ed., 1989, Cold Spring Harbor Press (Table of Contents).
Samuelov et al., J. Pharm. Sci., 1979, 325-329, 68(3).
Schlosky et al., J. Controlled Release, 1986, 87-108, 3(1-4).
Siriwardena et al., Circulation, 2010, 255-264, 122(3).
Stadlbauer et al., Chemistry, 2008, 2536-2541, 14(8).
Stein et al., Am. Heart J., 1998, 914-923, 135(5 (Part 1)).
Sweetman (Ed.), Martindale: The Complete Drug Reference, 33rd Edition, 2002, Pharmaceutical Press, Chicago (Table of Contents, 1360, 1860).
Tateyama et al., Biochem. Biophys. Res. Commun., 1992, 760-767, 185(2).
Theroux et al., Circulation, 1998, 1195-1206, 97(12).
US National Institutes of Health, Guide for the Care and Use of Laboratory Animals, 8th Ed., 2011, Washington, DC (NIH publication No. 85-23) (Table of Contents).
Weir et al. (Eds.), Handbook in Experimental in Immunology 4th Ed., 1986, 1, Blackwell Scientific Publications (Table of Contents).
Wiese et al., Circulation, 2000, 3074-3079, 102(25).
Wild (Ed.), The Immunoassay Handbook, 3rd Ed., 2005, 103, 121-126, Elsevier Ltd.
Yasue et al., Circulation, 1994, 195-203, 90(1).
Yazici et al., Pharmaceut. Dev. Technol., 1996, 175-183, 1(2).
Yoshimura et al., Circulation, 1993, 464-469, 87(2).
Zenter et al., J. Controlled Release, 1985, 217-229, 2.

\* cited by examiner

FIGURE 2
A
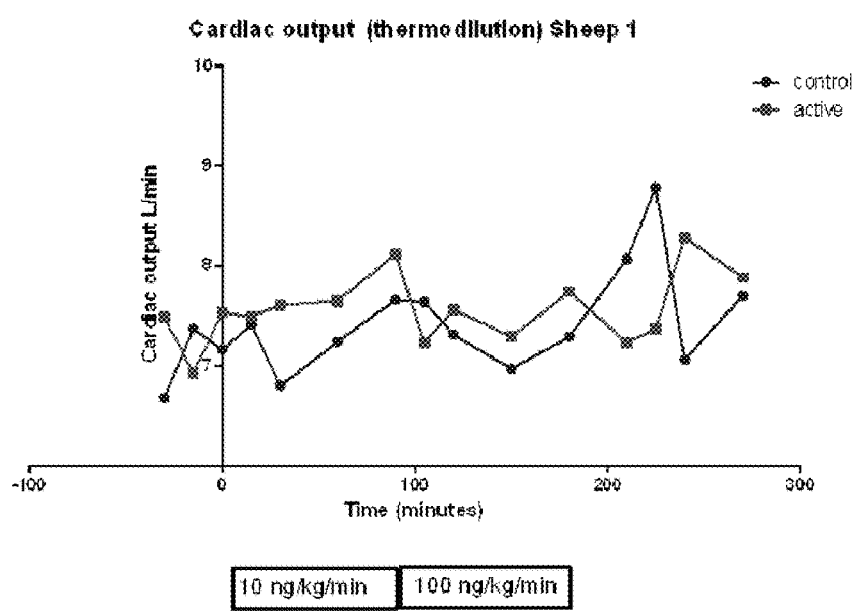
B
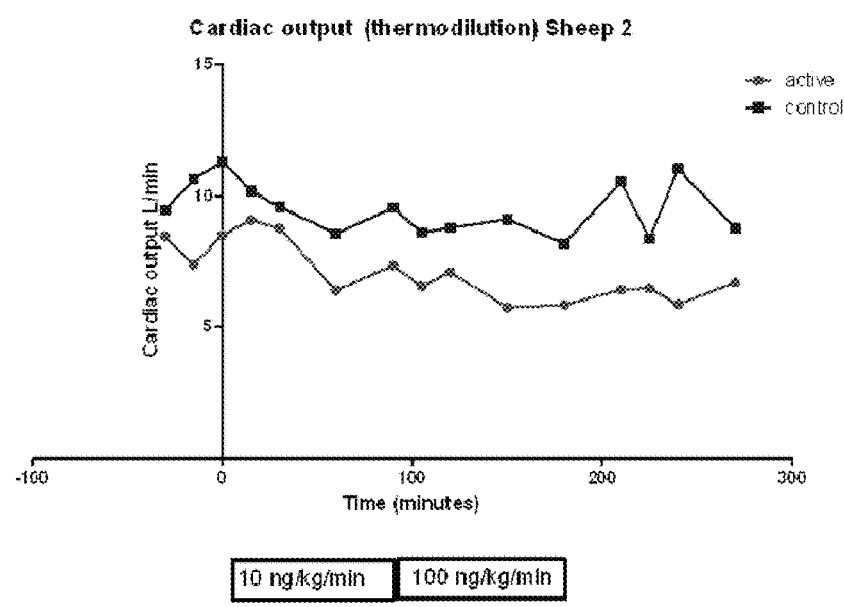

Preconditioning

FIGURE 7
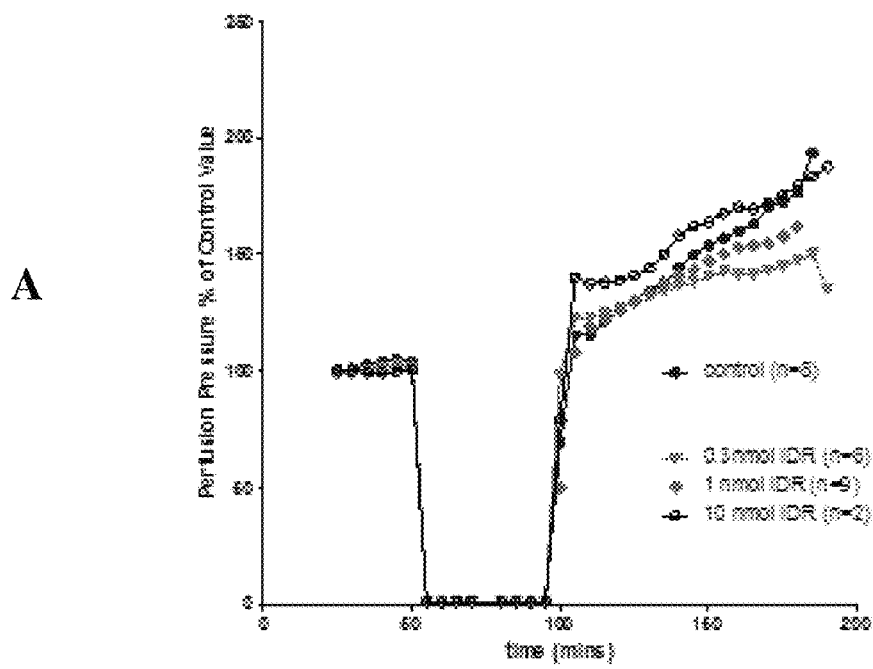
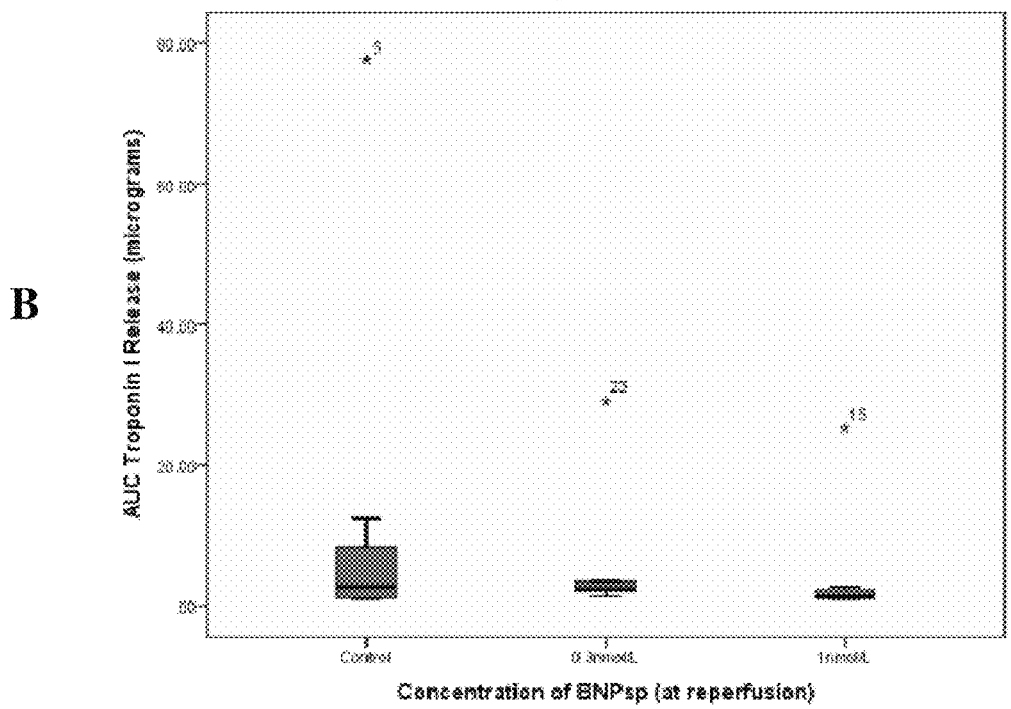

Developed pressures in isolated hearts receiving altered BNPsp sequences

CARDIOVASCULAR THERAPEUTICS

RELATED APPLICATION

This patent application claims the benefit of and priority to U.S. provisional patent application Ser. No. 61/525,140, filed 18 Aug. 2011, which is hereby incorporated by reference in its entirety for any and all purposes.

SEQUENCE LISTING

The instant application contains a Sequence Listing which has been submitted in ASCII format via EFS-Web and is hereby incorporated by reference in its entirety. Said ASCII copy, created on Nov. 13, 2012, is named OTA1101U.txt and is 8,973 bytes in size.

FIELD

The inventions relate to pharmaceuticals, compositions and methods useful for treating, preventing and ameliorating the effects of cardiovascular diseases, disorders and conditions, as well as articles and kits comprising such compounds and compositions.

BACKGROUND

The following includes information that may be useful in understanding the present invention. It is not an admission that any of the information, publications or documents specifically or implicitly referenced herein is prior art, or essential, to the presently described or claimed inventions. All publications and patents mentioned herein are hereby incorporated herein by reference in their entirety.

Heart disease, including ischemic heart disease, myocardial infarctions and other acute coronary syndromes, as well as heart failure, is a major health problem throughout the world.

It is understood, for example, that myocardial infarctions are a significant source of mortality among those individuals with heart disease. Myocardial infarction (MI) or acute myocardial infarction (AMI), commonly known as a heart attack, is the interruption of blood supply to a part of the heart, causing heart cells to die. This is most commonly due to occlusion (blockage) of a coronary artery following the rupture of a vulnerable atherosclerotic plaque, which is an unstable collection of lipids and white blood cells (especially macrophages) in the wall of an artery. The resulting ischemia and oxygen shortage, if left untreated for a sufficient period of time, can cause damage or death (infarction) of heart muscle tissue, i.e., the myocardium. Classical symptoms of acute myocardial infarction include sudden chest pain (typically radiating to the left arm or left side of the neck), shortness of breath, nausea, vomiting, palpitations, sweating, and anxiety. Approximately one quarter of all myocardial infarctions, however, are "silent," i.e., without chest pain or other symptoms. Immediate treatment for suspected acute myocardial infarction includes oxygen, aspirin, and sublingual nitroglycerin. Most cases of ST elevation MI (STEMI, also sometimes referred to as transmural myocardial infarction, or Q-wave myocardial infarction) are treated with thrombolysis or percutaneous coronary intervention (PCI). NSTEMI (non-ST elevation MI, also sometimes referred to as nontransmural myocardial infarction, or non-Q-wave myocardial infarction) is managed with medication, although PCI is often performed during hospital admission. Heart attacks are the leading cause of death for both men and women worldwide.

Heart failure (HF), often called congestive heart failure (CHF), is a clinical syndrome characterized by systemic perfusion inadequate to meet the body's metabolic demands as a result of impaired cardiac pump function, i.e., it is generally defined as the inability of the heart to supply sufficient blood flow to meet the needs of the body. Heart failure is a common, costly, disabling, and potentially deadly condition. McMurray J J, Pfeffer M A (2005) "Heart failure". Lancet 365 (9474): 1877-89. In developed countries, around 2% of adults suffer from heart failure, but in those over the age of 65, this increases to 6-10%. Id. Currently, it is estimated that more than 5 million Americans are afflicted with heart failure, approximately 2% of the population. American Heart Association. Heart Disease and Stroke Statistics—2008 Update. Dallas: American Heart Association, 2008. Both the human suffering and the financial burden associated with HF are substantial. Patients with heart failure account for about 1 million hospital admissions annually, and another 2 million patients have heart failure as a secondary diagnosis. One third of these patients are readmitted within 90 days for recurrent decompensation. Common causes of heart failure include myocardial infarction and other forms of ischemic heart disease, hypertension, valvular heart disease, and cardiomyopathy. McMurray J J, Pfeffer M A (2005) "Heart failure". Lancet 365 (9474): 1877-89.

Heart failure may be further subdivided into systolic or diastolic heart failure. In systolic heart failure, there is reduced cardiac contractility, whereas in diastolic heart failure there is impaired cardiac relaxation and abnormal ventricular filling. The most common cause of heart failure is left ventricular (LV) systolic dysfunction (about 60% of patients). In this category, most cases are a result of end-stage coronary artery disease, either with a history of myocardial infarction or with a chronically underperfused, yet viable, myocardium. In many patients, both processes are present simultaneously. Other common causes of LV systolic dysfunction include idiopathic dilated cardiomyopathy, valvular heart disease, hypertensive heart disease, toxin-induced cardiomyopathies (e.g., doxorubicin, herceptin, alcohol), and congenital heart disease. Heart failure can also develop as a result of right ventricular infarction, pulmonary hypertension, chronic severe tricuspid regurgitation, or arrhythmogenic right ventricular dysplasia. A less-common cause of heart failure is high-output failure caused by thyrotoxicosis, arteriovenous fistulae, Paget's disease, pregnancy, or severe chronic anemia. Diastolic LV dysfunction (impaired relaxation) usually is related to chronic hypertension or ischemic heart disease. Other causes include restrictive, infiltrative, and hypertrophic cardiomyopathies. Inadequate filling of the right ventricle can result from pericardial constriction or cardiac tamponade. Patients at high risk for developing heart failure are those with hypertension, coronary artery disease, diabetes mellitus, family history of cardiomyopathy, use of cardiotoxins, and obesity. Heart failure is a common syndrome, especially in older adults. Although more patients survive acute myocardial infarction because of reperfusion therapy, most have at least some residual LV systolic dysfunction, which can lead to heart failure. Currently, heart failure has no cure. While treatments such as medicines and lifestyle changes can help people live longer and more active lives, researchers continue to look for new ways to treat heart failure and its complications.

Chest pain is a nonspecific symptom that can have cardiac causes, and the term angina is typically reserved for pain syndromes arising from presumed myocardial ischemia. The term unstable angina was first used to signify the intermediate state between myocardial infarction and the more chronic state of stable angina. The old term, preinfarction angina, conveys the clinical intent of intervening to attenuate the risk of myocardial infarction or death. Patients with this condition have also been categorized according to their presentation, diagnostic test results, or course over time; these categories include new-onset angina, accelerating angina, rest angina, early postinfarct angina, and early postrevascularization angina. Unstable angina is considered to be an acute coronary syndrome in which there is no release of the enzymes and biomarkers of myocardial necrosis. Although the etiology and definition of unstable angina can be broad, interplay between disrupted atherosclerotic plaque and overlaid thrombi is present in many cases of unstable angina, with consequent hemodynamic deficit or microembolization. This is distinct from stable angina, in which the typical underlying cause is a fixed coronary stenosis with compromised blood flow and slow, progressive plaque growth that allows for the occasional development of collateral flow.

"Acute Coronary Syndrome" (ACS) has been applied to a group of coronary disorders that result from ischemic insult to the heart. ACS includes patients who have or are at high risk of developing an MI. Patients with ACS present to the physician with conditions that span a continuum that includes unstable angina, STEMI, NSTEMI and transmural (Q-wave) MI. ACS also include cardiac ischemia, and is believed to result largely from thrombus deposition and growth within one or more coronary arteries, resulting in a partial or complete occlusion of the artery, and frequently involves rupture of the plaque, resulting in an ischemic injury. ACS may also be precipitated by a coronary vasospasm or increased myocardial demand. For review, see, e.g., Davies, Clin. Cardiol. (Supp. I): 12 17 (1997). The seriousness of ACS is underlined by the morbidity and mortality that follow the ischemic insult. For example, workers have estimated that within four to six weeks of presentation with ACS, the risk of death or a subsequent MI is 8-14%, and the rate of death, MI, or refractory ischemia is 15-25%. Theroux and Fuster, $Circulation$ 97:1195 1206 (1998). Given that the total number of deaths in the U.S. from acute MI is about 600,000, the search within the art for information that relates to the therapeutic management of ACS has understandably been extensive.

B-type natriuretic peptide (BNP or BNP-32) is a 32-amino acid neurohormone that is synthesized in ventricular myocardium and released into the circulation in response to ventricular dilation and pressure overload. The plasma concentration of BNP is elevated among CHR patients, and increases in proportion to the degree of left ventricular dysfunction and the severity of CHF symptoms. For review, see, e.g., Wiese et al., $Circulation$ 102: 3074 9 (2000); Yasue et al., $Circulation$ 90: 195 203 (1994); Yoshimura et al., $Circulation$ 87: 464 9 (1993); Stein and Levin, $Am. Heart J.$ 135: 914 23 (1998); and Omland et al., $Heart$ 76: 232 7 (1996). The precursor to BNP is synthesized as a 134-amino acid precursor molecule referred to as "pre pro BNP," which is cleaved into a signal peptide comprising amino acids 1-26 and a 108-amino acid molecule consisting of amino acids 27-134, referred to as "pro BNP." Pro BNP is proteolytically processed into a 76-amino acid N-terminal peptide (amino acids 1-76), referred to as "NT pro BNP" and the 32-amino acid mature hormone, referred to as BNP or BNP 32 (amino acids 77-108). It has been reported that NT pro-BNP, BNP-32, and the pre pro BNP can circulate in human plasma. See, e.g., Tateyama et al., Biochem. Biophys. Res. Commun. 185: 760 7 (1992); Hunt et al., Biochem. Biophys. Res. Commun. 214: 1175 83 (1995).

In August 2001, hBNP (native peptide) was approved by the FDA under the trade name Natrecor (nesiritide) for the treatment of acute congestive heart failure. Natrecor was the first drug approved for the treatment of CHF in over twelve years. It is administered by intravenous continuous infusion over a period of 48 hours in patients with acute decompensated or advanced CHF who have dyspnea at rest or with minimal activity. As the drug is expensive and requires hospitalization, Natrecor is only used for the most acute cases. Additionally, the therapeutic usefulness of BNP is limited by endopeptidase degradation, as well as natriuretic peptide clearance receptor (NPR-C) mediated internalization, which causes these proteins to have a fairly short half-life in vivo. For example, the plasma half life of BNP is estimated to be approximately 20 minutes (Potter et al., Endocrine Reviews 27(1):42-72 (2006)), and previous therapeutic administration of these peptides has been limited to time consuming intravenous infusion, typically in a hospital or other medical care facility.

There remains a need in the art for new therapeutics useful in treating patients having or at risk for developing cardiovascular diseases, disorders and conditions, including ischemic heart disease, acute coronary syndromes and heart failure. There is a particular need for new therapeutics that span the entire spectrum of cardiovascular diseases, disorders and conditions associated with ischemia and/or oxidative stress. Such therapeutics are described and claimed herein, based on surprising discoveries indicating, for example, that signal peptide fragments of BNP are novel cardioprotective and therapeutic agents.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction.

In one aspect, the inventions provided herein include compounds. The compounds are useful for the treatment of cardiovascular disorders. In another aspect, the inventions include compositions comprising or consisting essentially of one or more of those compounds.

Compounds of the invention, which in a non-limiting preferred embodiment are isolated or substantially pure, include the following peptides: LHLAFLGGRS (SEQ.ID.NO:1), LHLAFLGGR (SEQ.ID.NO:2), LHLAFLGG (SEQ.ID.NO:3), LHLAFLG (SEQ.ID.NO:4), LHLAFL (SEQ.ID.NO:5) and LHLAF (SEQ.ID.NO:6), LHLA (SEQ.ID.NO:7), LHL (SEQ.ID.NO:8), LH (SEQ.ID.NO:9). In the above peptides shown as SEQ.ID.NO:1-9, any one or more of the Leucines (L) can be substituted with Isoleucine (I), with D-leucine or D-isoleucine, or with tert-leucine, norleucine, L-allo-isoleucine, D-allo-isoleucine, D-tert-leucine and D-norleucine, and/or the histidine can be substituted with any non-naturally occurring amino acid that has or is prepared to have a side chain terminating with an imidazole ring all of which are SEQ.ID.NO:1-9 analogs.

Compounds of the invention, which in a non-limiting preferred embodiment are isolated or substantially pure, also include peptides according to the following Formula I:

LHX$_1$X$_2$X$_3$X$_4$X$_5$X$_6$X$_7$X$_8$ (SEQ ID NO: 10)

wherein X$_1$ is Norleucine, Ile, Val, Met, Ala, Phe or Gly; X$_2$ is Val, Leu, Ile or Gly; X$_3$ is Leu, Val, Ile, Ala, Tyr or Gly; X$_4$ is Norleucine, Ile, Val, Met, Ala, Phe or Gly; X$_5$ is Pro, Ala, Arg or Ser; X$_6$ is Pro, Ala, Arg or Ser; X$_7$ is Arg, Gln, Asn or Gly; and X$_8$ is Thr or Gly.

Compounds of the invention, which in a non-limiting preferred embodiment are isolated or substantially pure, also include peptides according to the following Formula II:

LHX$_1$X$_2$X$_3$X$_4$X$_5$X$_6$X$_7$ (SEQ ID NO: 11)

wherein X$_1$ is Norleucine, Ile, Val, Met, Ala, Phe or Gly; X$_2$ is Val, Leu, Ile or Gly; X$_3$ is Leu, Val, Ile, Ala, Tyr or Gly; X$_4$ is Norleucine, Ile, Val, Met, Ala, Phe or Gly; X$_5$ is Pro, Ala, Arg or Ser; X$_6$ is Pro, Ala, Arg or Ser; and X$_7$ is Arg, Gln, Asn or Gly; provided that where X$_1$ is Norleucine, Ile, Val, Met, Ala, Phe or Gly, X$_2$ can also be Ala, X$_3$ can also be Phe, X$_4$ can also be Leu, X$_5$ can also be Gly, X$_6$ can also be Gly, and X$_7$ can also be Arg;

where X$_2$ is Val, Leu or Ile or Gly, X$_1$ can also be Leu, X$_3$ can also be Phe, X$_4$ can also be Leu, X$_5$ can also be Gly, X$_6$ can also be Gly, and X$_7$ can also be Arg;

where X$_3$ is Leu, Val, Ile, Ala, Tyr or Gly, X$_1$ can also be Leu, X$_2$ can also be Ala, X$_4$ can also be Leu, X$_5$ can also be Gly, X$_6$ can also be Gly, and X$_7$ can also be Arg;

where X$_4$ is Norleucine, Ile, Val, Met, Ala, Phe or Gly, X$_1$ can also be Leu, X$_2$ can also be Ala, X$_3$ can also be Phe, X$_5$ can also be Gly, X$_6$ can also be Gly, and X$_7$ can also be Arg;

where X$_5$ is Pro, Ala, Arg or Ser, X$_1$ can also be Leu, X$_2$ can also be Ala, X$_3$ can also be Phe, X$_4$ can also be Leu, X$_6$ can also be Gly, and X$_7$ can also be Arg;

where X$_6$ is Pro, Ala, Arg or Ser, X$_1$ can also be Leu, X$_2$ can also be Ala, X$_3$ can also be Phe, X$_4$ can also be Leu, X$_5$ can also be Gly, and X$_7$ can also be Arg;

where X$_7$ is Lys, Gln, Asn or Gly, X$_1$ can also be Leu, X$_2$ can also be Ala, X$_3$ can also be Phe, X$_4$ can also be Leu, X$_5$ can also be Gly, and X$_6$ can also be Gly.

Compounds of the invention, which in a non-limiting preferred embodiment are isolated or substantially pure, also include peptides according to the following Formula III:

LHX$_1$X$_2$X$_3$X$_4$X$_5$X$_6$ (SEQ ID NO: 12)

wherein X$_1$ is Norleucine, Ile, Val, Met, Ala, Phe or Gly; X$_2$ is Val, Leu, Ile or Gly; X$_3$ is Leu, Val, Ile, Ala, Tyr or Gly; X$_4$ is Norleucine, Ile, Val, Met, Ala, Phe or Gly; X$_5$ is Pro, Ala, Arg or Ser; and X$_6$ is Pro, Ala, Arg or Ser; provided where X$_1$ is Norleucine, Ile, Val, Met, Ala, Phe or Gly, X$_2$ can also be Ala, X$_3$ can also be Phe, X$_4$ can also be Leu, X$_5$ can also be Gly, X$_6$ can also be Gly, and X$_7$ can also be Arg;

where X$_2$ is Val, Leu or Ile or Gly, X$_1$ can also be Leu, X$_3$ can also be Phe, X$_4$ can also be Leu, X$_5$ can also be Gly, X$_6$ can also be Gly, and X$_7$ can also be Arg;

where X$_3$ is Leu, Val, Ile, Ala, Tyr or Gly, X$_1$ can also be Leu, X$_2$ can also be Ala, X$_4$ can also be Leu, X$_5$ can also be Gly, X$_6$ can also be Gly, and X$_7$ can also be Arg;

where X$_4$ is Norleucine, Ile, Val, Met, Ala, Phe or Gly, X$_1$ can also be Leu, X$_2$ can also be Ala, X$_3$ can also be Phe, X$_5$ can also be Gly, X$_6$ can also be Gly, and X$_7$ can also be Arg;

where X$_5$ is Pro, Ala, Arg or Ser, X$_1$ can also be Leu, X$_2$ can also be Ala, X$_3$ can also be Phe, X$_4$ can also be Leu, X$_6$ can also be Gly, and X$_7$ can also be Arg;

where X$_6$ is Pro, Ala, Arg or Ser, X$_1$ can also be Leu, X$_2$ can also be Ala, X$_3$ can also be Phe, X$_4$ can also be Leu, X$_5$ can also be Gly, and X$_7$ can also be Arg.

Compounds of the invention, which in a non-limiting preferred embodiment are isolated or substantially pure, also include peptides according to the following Formula IV:

LHX$_1$X$_2$X$_3$X$_4$X$_5$ (SEQ ID NO: 13)

wherein X$_1$ is Norleucine, Ile, Val, Met, Ala, Phe or Gly; X$_2$ is Val, Leu, Ile or Gly; X$_3$ is Leu, Val, Ile, Ala, Tyr or Gly; X$_4$ is Norleucine, Ile, Val, Met, Ala, Phe or Gly; and X$_5$ is Pro, Ala, Arg or Ser; provided that where X$_1$ is Norleucine, Ile, Val, Met, Ala, Phe or Gly, X$_2$ can also be Ala, X$_3$ can also be Phe, X$_4$ can also be Leu, X$_5$ can also be Gly, X$_6$ can also be Gly, and X$_7$ can also be Arg;

where X$_2$ is Val, Leu or Ile or Gly, X$_1$ can also be Leu, X$_3$ can also be Phe, X$_4$ can also be Leu, X$_5$ can also be Gly, X$_6$ can also be Gly, and X$_7$ can also be Arg;

where X$_3$ is Leu, Val, Ile, Ala, Tyr or Gly, X$_1$ can also be Leu, X$_2$ can also be Ala, X$_4$ can also be Leu, X$_5$ can also be Gly, X$_6$ can also be Gly, and X$_7$ can also be Arg;

where X$_4$ is Norleucine, Ile, Val, Met, Ala, Phe or Gly, X$_1$ can also be Leu, X$_2$ can also be Ala, X$_3$ can also be Phe, X$_5$ can also be Gly, X$_6$ can also be Gly, and X$_7$ can also be Arg;

where X$_5$ is Pro, Ala, Arg or Ser, X$_1$ can also be Leu, X$_2$ can also be Ala, X$_3$ can also be Phe, X$_4$ can also be Leu, X$_6$ can also be Gly, and X$_7$ can also be Arg.

Compounds of the invention, which in a non-limiting preferred embodiment are isolated or substantially pure, also include peptides according to the following Formula V:

LHX$_1$X$_2$X$_3$X$_4$ (SEQ ID NO: 14)

wherein X$_1$ is Norleucine, Ile, Val, Met, Ala, Phe or Gly; X$_2$ is Val, Leu, Ile or Gly; X$_3$ is Leu, Val, Ile, Ala, Tyr or Gly; and X$_4$ is Norleucine, Ile, Val, Met, Ala, Phe or Gly; provided that where X$_1$ is Norleucine, Ile, Val, Met, Ala, Phe or Gly, X$_2$ can also be Ala, X$_3$ can also be Phe, X$_4$ can also be Leu, X$_5$ can also be Gly, X$_6$ can also be Gly, and X$_7$ can also be Arg;

where X$_2$ is Val, Leu or Ile or Gly, X$_1$ can also be Leu, X$_3$ can also be Phe, X$_4$ can also be Leu, X$_5$ can also be Gly, X$_6$ can also be Gly, and X$_7$ can also be Arg;

where X$_3$ is Leu, Val, Ile, Ala, Tyr or Gly, X$_1$ can also be Leu, X$_2$ can also be Ala, X$_4$ can also be Leu, X$_5$ can also be Gly, X$_6$ can also be Gly, and X$_7$ can also be Arg;

where X$_4$ is Norleucine, Ile, Val, Met, Ala, Phe or Gly, X$_1$ can also be Leu, X$_2$ can also be Ala, X$_3$ can also be Phe, X$_5$ can also be Gly, X$_6$ can also be Gly, and X$_7$ can also be Arg.

Compounds of the invention, which in a non-limiting preferred embodiment are isolated or substantially pure, also include peptides according to the following Formula VI:

LHX$_1$X$_2$X$_3$ (SEQ ID NO: 15)

wherein X$_1$ is Norleucine, Ile, Val, Met, Ala, Phe or Gly; X$_2$ is Val, Leu, Ile or Gly; and X$_3$ is Leu, Val, Ile, Ala, Tyr or Gly; provided that where X$_1$ is Norleucine, Ile, Val, Met, Ala, Phe or Gly, X$_2$ can also be Ala, and X$_3$ can also be Phe;

where X$_2$ is Val, Leu or Ile or Gly, X$_1$ can also be Leu, and X$_3$ can also be Phe; and where X$_3$ is Leu, Val, Ile, Ala, Tyr or Gly, X$_1$ can also be Leu, and X$_2$ can also be Ala.

Compounds of the invention, which in a non-limiting preferred embodiment are isolated or substantially pure, also include peptides according to the following Formula VII:

LHX$_1$X$_2$ (SEQ ID NO: 16)

wherein X$_1$ is Norleucine, Ile, Val, Met, Ala, Phe or Gly; and X$_2$ is Val, Leu, Ile or Gly; provided that where $X_1$ is Norleucine, Ile, Val, Met, Ala, Phe or Gly, $X_2$ can also be Ala; and where $X_2$ is Val, Leu or Ile or Gly, $X_1$ can also be Leu.

Compounds of the invention, which in a non-limiting preferred embodiment are isolated or substantially pure, also include peptides according to the following Formula VIII:

LHX$_1$ (SEQ ID NO: 17)

wherein $X_1$ is Norleucine, Ile, Val, Met, Ala, Phe or Gly.

Included in the scope of the invention are active analogs and conservative variants of these compounds, including truncations thereof, preferably C-terminal truncations. Additionally, for example, in the peptides shown in Formulae I-VIII, any one or more of the Leucines (L) can be substituted with Isoleucine (I), with D-leucine or D-isoleucine, or with tert-leucine, norleucine, L-allo-isoleucine, D-allo-isoleucine, D-tert-leucine and D-norleucine, and/or the histidine can be substituted with any non-naturally occurring amino acid that has or is prepared to have a side chain terminating with an imidazole ring, all of which are further analogs thereof.

In one non-limiting embodiment, one or more of the amino acids of the peptides within the scope of the invention, including SEQ.ID.NOS:1-9 and sequences within Formulae I-VIII, may be in the L- or D-configuration. In other embodiments, one or more of the amino acids of the peptides within the scope of the invention are naturally-occurring non-genetically coded amino acids. In still other embodiments, one or more of the amino acids of the peptides within the scope of the invention are amino acid analogs or synthetic amino acids.

In another non-limiting embodiment, the N-terminal Leucine (or Isoleucine D-leucine, D-isoleucine, tert-leucine, norleucine, L-allo-isoleucine, D-allo-isoleucine, D-tert-leucine or D-norleucine) of the peptides within the scope of the invention, including SEQ.ID.NOS:1-9 and sequences within Formulae I-VIII, may be modified to contain a formyl group, a group comprising a formyl group, an ester of a carboxylic acid (preferably an aldehyde ester, e.g., a carboxyethyl group, a carboxymethyl group, etc.), or a group comprising a an ester of a carboxylic acid. Modifications with formyl, carboxyethyl, and carboxymethyl groups are presently preferred.

In another embodiment, one or more the amino acids in compounds within the scope of the invention, including SEQ.ID.NOS:1-9 and sequences within Formulae I-VIII, are substituted for another amino acid from a similar amino acid class or subclass, based primarily upon the chemical and physical properties of the amino acid side chain. For example, one or more hydrophilic or polar amino acids can be substituted for another hydrophilic or polar amino acid. Likewise, one or more hydrophobic or nonpolar amino acids can be substituted for another hydrophobic or nonpolar amino acid. In making such substitutions, polar amino acids can be further subdivided into amino acids having acidic, basic or hydrophilic side chains and nonpolar amino acids can be further subdivided amino acids having aromatic or hydrophobic side chains. Nonpolar amino acids may be further subdivided to include, among others, aliphatic amino acids.

Also within the scope of the invention are compounds of the invention that have been modified to improve their biopharmaceutical properties. In certain embodiments, the compounds of the invention are modified, for example, to provide increased stability, increased resistance to proteolytic inactivation, decreased to nonexistent immunogenicity, increased circulatory lives, including modified serum half-lives and modified therapeutic half-lives, and low toxicity. Modified forms of compounds of the invention include prodrug forms, representative examples of which are described elsewhere herein. Methods by which the compounds of the invention can be modified also include, for example, by PEGylation, by chemical derivitization, and by fusion or conjugation with peptides or lipids. Modified compounds include modified Type-B natriuretic signal peptide fragment agents, including, for example, modified BNPsp(17-26) (SEQ ID NO:1), and modified analogs, variants (e.g., conservative variants) and truncations thereof. Other embodiments include peptides selected from SEQ.ID.NOS:2 to 9 that have been modified, and peptides according to Formula I, Formula II, Formula III, Formula IV, Formula V, Formula VI, Formula VII and/or Formula VIII that has been modified, and active analogs, variants (e.g., conservative variants) and truncations thereof that have been modified.

Other embodiments include peptidiomimetics of compounds of the invention.

The present inventions also include pharmaceutical compositions comprising or consisting essentially of a Type-B natriuretic signal peptide fragment agent and a pharmaceutically acceptable carrier. In one embodiment, the pharmaceutical composition comprises or consists essentially of BNPsp(17-26) (SEQ ID NO:1). In another embodiment, the pharmaceutical composition comprises or consists essentially of a sequence selected from SEQ.ID.NOS:2 to 9. In another embodiment, the pharmaceutical composition comprises or consists essentially of a sequence selected from Formula I, Formula II, Formula III, Formula IV, Formula V, Formula VI, Formula VII and/or Formula VIII. Included in the scope of the invention are pharmaceutical compositions including one or more active analogs and conservative variants of these compounds, including truncations thereof, preferably C-terminal truncations. In one embodiment, the inventions include pharmaceutical compositions comprising or consisting essentially of a Type-B natriuretic signal peptide fragment or a therapeutically active analog or variant or truncation thereof.

In another embodiment, the inventions include pharmaceutical compositions comprising or consisting essentially of compounds of the invention, including analogs, variants, truncations, etc., that have been modified to improve their biopharmaceutical properties. In certain embodiments, the compounds of the invention are modified, for example, to provide increased stability, increased resistance to proteolytic inactivation, decreased to nonexistent immunogenicity, increased half-lives or circulatory lives, and low toxicity. Methods by which the compounds of the invention can be modified include, for example, by PEGylation, by chemical derivitization, and by fusion or conjugation with peptides or lipids.

The inventions include a pharmaceutical composition comprising one or more pharmaceutically acceptable Type-B natriuretic signal peptide agents for the treatment of a cardiovascular disorder, e.g., an acute coronary syndrome, heart failure, ischemic heart disease, etc., and related cardiovascular diseases, disorders and conditions characterized at least in party by ischemia and/or oxidative stress, and related disorders and conditions. Certain preferred Type-B natriuretic signal peptide agents are identified herein as SEQ.ID.NOS:1 to 9. BNPsp(17-26) (SEQ ID NO:1) is most preferred. Other Type-B natriuretic signal peptide agents are within Formula I, Formula II, Formula III, Formula IV, Formula V, Formula VI, Formula VII and Formula VIII.

Other embodiments include active analogs, variants (e.g., conservative variants) and truncations of the foregoing, and a pharmaceutically acceptable carrier. Thus, the inventions include pharmaceutical compositions in a form suitable for, or adapted to, treatment of a subject for a cardiovascular disease, disorder or condition. In one embodiment, the cardioiovascular disease, disorder or condition is associated with ischemia and/or oxidative stress. In certain embodiments, the cardiovascular disease, disorder or condition is an acute coronary syndrome. The acute coronary syndrome may, for example, be selected from the group consisting of ST-segment elevation myocardial infarction, non-ST-segment elevation myocardial infarction and unstable angina. In other embodiments, the cardiovascular disease, disorder or condition is ischemic heart disease. In other embodiments, the cardiovascular disease, disorder or condition is heart failure (any form). For example, the heart failure may be systolic or diastolic heart failure. The heart failure may result from left ventricular systolic dysfunction. The heart failure may also be a result of right ventricular infarction, pulmonary hypertension, chronic severe tricuspid regurgitation, or arrhythmogenic right ventricular dysplasia. The heart failure may also be a result of diastolic LV dysfunction. In another embodiment the cardioiovascular disease, disorder or condition is ischemic heart disease.

In one aspect, the invention includes pharmaceutical compositions useful for preventing and/or treating a cardiovascular disorder in a subject, e.g., an acute coronary syndrome, heart failure, ischemic heart disease, etc., and related cardiovascular diseases, disorders and conditions involving ischemia and/or oxidative stress, and related disorders and conditions, including parenteral delivery forms and formulations, as well as other forms of delivery including forms for delivery by infusion, injection and instillation, and delayed, slow, extended or controlled release compositions, devices and matrices, comprising or consisting essentially of therapeutically effective amounts of a Type-B natriuretic signal peptide fragment agent alone or in combination with another cardiovascular therapeutic agent(s), and a pharmaceutically acceptable carrier. In certain preferred embodiments, the pharmaceutical compositions are formulated for intravenous administration, including by infusion or as a bolus. Other formulations for other routes of administration are also within the scope of the invention, including, for example, formulations for nasal, pulmonary, buccal, rectal, transdermal and oral delivery.

In another aspect, the compositions of the invention comprise about 0.01 to about 100 milligrams, about 100 to about 500 milligrams, or about 500 to about 1000 milligrams or more of a compound of the invention, for example, a Type-B natriuretic signal peptide fragment or Type-B natriuretic signal peptide fragment analog, including one or more of SEQ.ID.NOS:1-9 and peptides according to any of Formulae I to VIII. Other doses are described herein and include doses ranging from at least about 100 nanograms, including, for example at least about 200 nanograms, 600 nanograms, 2000 nanograms, 6000 nanograms and at least about 10,000 nanograms or more. Dose concentrations include concentrations of at least about 0.1 moles per liter, including, for example, at least about 0.3, 1.0, 3.0 and 10.0 nMoles/L. Dose concentrations also include concentrations of 0.1 nMoles/L, 0.3 nMoles/L, 1.0 nMoles/L, 3.0 nMoles/L and 10.0 nMoles/L. These dose concentrations are equivalent to 0.1, 0.3, 1, 3, 11 µg/L and administrable weight doses of 0.4, 1.0, 4.0, 10 and 39 micrograms/kg (µg/kg). Also within the invention are other doses ranging from 0.1 to 5.0 µg/kg and 0.1 to 10.0 µg/kg. Additionally, doses of about 0.4, 1.0, 4.0, 10 and 39 µg/kg are within the invention. Doses of at least about 0.4, 1.0, 4.0, 10 and 39 µg/kg are also within the invention. These compositions and amounts may be provided as single or multiple doses.

The inventions also include methods of treatment of a subject having or at risk for developing a cardiovascular disease, disorder or condition, comprising administering to the subject a therapeutically effective amount of one or more of the compounds or pharmaceutical compositions described herein. In one non-limiting embodiment, the cardiovascular disease, disorder or condition is associated with ischemia and/or oxidative stress. In one embodiment, the cardiovascular disease, disorder or condition is an acute coronary syndrome, e.g., ST-segment elevation myocardial infarction, non-ST-segment elevation myocardial infarction or unstable angina. In another embodiment, the cardiovascular disease, disorder or condition is heart failure. In other embodiments, the cardiovascular disease, disorder or condition is ischemic heart disease. In another embodiment, the cardiovascular disease, disorder or condition is stable angina.

The inventions include methods of treating a subject having or at risk for developing a cardiovascular disease, disorder or condition, comprising a therapeutically effective amount of a Type-B natriuretic signal peptide fragment agent and a pharmaceutically acceptable carrier. In one embodiment, the Type-B natriuretic signal peptide fragment agent in the pharmaceutical composition is BNPsp(17-26) (SEQ ID NO:1). In another embodiment, the Type-B natriuretic signal peptide fragment in the pharmaceutical composition comprises or consists essentially of a sequence selected from SEQ.ID.NOS:2 to 9. In another embodiment, the Type-B natriuretic signal peptide fragment agent in the pharmaceutical composition comprises or consists essentially of a sequence selected from Formula I, Formula II, Formula III, Formula IV, Formula V, Formula VI, Formula VII or Formula VIII. Type-B natriuretic signal peptide fragment agents also include active analogs, variants, truncations, and modified forms of the Type-B natriuretic signal peptide fragment agents described herein.

In another aspect, the inventions include methods of treating and/or preventing a cardiovascular disease, disorder or condition that is associated with ischemia and/or oxidative stress in a subject by increasing Type-B natriuretic signal peptide fragment activity in the subject. This may be accomplished, for example, by administering to the subject a composition comprising a therapeutically effective amount of a Type-B natriuretic signal peptide fragment agent, e.g., a Type-B natriuretic signal peptide fragment or a Type-B natriuretic signal peptide fragment, including a BNPsp fragment comprising or consisting essentially of a sequence selected from SEQ.ID.NOS:1-9, or a peptide comprising or consisting essentially of a peptide according to any of Formulae I to VIII, or an analog, variant, truncation or modification thereof. In certain embodiments, about 0.01 to about 100, 500 or 1000 nanograms or milligrams or more (e.g., at least about 100 nanograms or milligrams, at least about 500 nanograms or milligrams, or at least about 1000 nanograms or milligrams) of a BNPsp fragment or Type-B natriuretic signal peptide fragment analog, e.g., a BNPsp fragment comprising or consisting essentially of a sequence selected from SEQ.ID.NOS:1-9, or a peptide comprising or consisting essentially of a peptide according to any of Formulae I to VIII, is administered per day in single or divided doses or by continuous infusion, for example.

In another aspect, the inventions include methods of treating a patient suffering from chest pain of any cause, including acute coronary syndrome, comprising administering to the patient a therapeutically effective amount of a Type-B natriuretic signal peptide fragment agent, wherein the patient is not suffering from a Q-wave MI or STEMI. In a certain embodiment of this method, the patient is suffering from unstable angina. In another embodiment of this method, the patient is suffering from non-Q-wave cardiac necrosis. In still another embodiment of this method, the patient has a blood troponin I level of no more than 0.4 ng/ml. In yet another embodiment of this method, the patient has a blood troponin T level of no more than 0.1 ng/ml. In yet another embodiment of this method, the patient does not have elevated blood creatine kinase. In still another embodiment of this method, the patient does not have ST-segment elevation. In yet another embodiment of this method, the patient does not exhibit a pathological Q-wave. In another embodiment of this method, the patient exhibits one or more of the following symptoms: chest pain greater than 15 minutes in duration, chest pain at rest, or chest pain following minimal exertion that is poorly responsive to sublingual nitrates.

In one embodiment, the Type-B natriuretic signal peptide fragment agent is administered in a single dose. In another embodiment, the Type-B natriuretic signal peptide fragment agent is administered in more than one dose. In yet another embodiment, the Type-B natriuretic signal peptide fragment agent is administered continuously over a period of time, for example a predetermined period of time. In still another embodiment, glucose or a potassium salt, or a combination thereof, is co-administered with the Type-B natriuretic signal peptide fragment agent.

In another aspect, the inventions include methods for treatment of a patient, comprising administering to the individual a therapeutically effective amount of a Type-B natriuretic signal peptide fragment agent, wherein the administration is after the onset of one or more of the following symptoms: chest pain lasting longer than 15 minutes, chest pain at rest, chest pain following minimal exertion, nausea, shortness of breath, palpitations, or dizziness. In other embodiments, the patient has not suffered a Q-wave MI or STEMI prior to the onset of the symptom or symptoms; patient is suffering from unstable angina; the patient is suffering from non-Q-wave cardiac necrosis; the patient has a blood troponin I level of no more than 0.4 ng/ml; the patient has a blood troponin T level of no more than 0.1 ng/ml; the patient does not have elevated blood creatine kinase myocardial isoenzyme; the patient does not have ST-segment elevation; the patient does not exhibit a pathological Q-wave; the administration occurs between the time of onset of the one or more symptoms, and the time the patient suffers a Q-wave MI or STEMI. In another embodiment, the method further comprises the step of continuing the administration of a Type-B natriuretic signal peptide fragment agent during the time that the patient suffers a Q-wave MI or STEMI. In yet another embodiment, the method further comprises the step of continuing the administration of a Type-B natriuretic signal peptide fragment agent after the time the patient suffers a Q-wave MI or STEMI. In other embodiments of this method, the patient has ischemic heart disease, or is at risk for developing ischemic heart disease. In still another embodiment of the method, the patient has one or more of the following cardiac abnormalities: congestive heart failure, worsening heart murmur due to mitral regurgitation, or evidence of cardiac conduction disturbances. In other embodiments, the patient has a normal ECG. In another embodiment of this method, the patient has stable angina. In other embodiments of the method, the Type-B natriuretic signal peptide fragment agent is administered in a single dose, or is administered in more than one dose, or is administered continuously. In an additional embodiment of this method, glucose or a potassium salt, or a combination thereof, is co-administered with the Type-B natriuretic signal peptide fragment agent.

The inventions also include methods for treating a patient suffering from stable angina, comprising administration of a Type-B natriuretic signal peptide fragment agent. In a further embodiment, the administration is continuous over a period of time, including a predetermined period of time.

The inventions also provide a method for performing angioplasty on a patient in need thereof, comprising administering a Type-B natriuretic signal peptide fragment agent to the patient during the angioplasty procedure. In a further embodiment, the method comprises or further comprises administering a Type-B natriuretic signal peptide fragment agent to the patient prior to the angioplasty procedure. In a further embodiment, the method comprises or further comprises administering a Type-B natriuretic signal peptide fragment agent to the patient following the angioplasty procedure. In other embodiments, a Type-B natriuretic signal peptide fragment agent is administered to the patient before, during, and/or after the angioplasty procedure, in any combination.

The inventions also include methods for treatment of a patient with ischemic heart disease, or is at risk for developing ischemic heart disease, including patients who exhibit one or more of the following symptoms: nausea, shortness of breath, palpitations, or dizziness, and further wherein the patient does not exhibit chest pain, comprising administering to the patient a therapeutically effective amount of a Type-B natriuretic signal peptide fragment agent, wherein the patient is not suffering a Q-wave MI or STEMI. In another embodiment of this method, the patient has a normal ECG.

Also provided are methods for increasing the time during which thrombolytic therapy will be effective following the first symptom of cardiac distress, comprising administering a therapeutically effective amount of a Type-B natriuretic signal peptide fragment agent after the onset of one or more of the following symptoms: chest pain lasting longer than 15 minutes, chest pain at rest, chest pain following minimal exertion, nausea, shortness of breath, palpitations, or dizziness.

In another aspect, the treated subject is a mammal, preferably a human. Other mammals include domestic and farm animals, and zoo, sports, or pet animals, such as dogs, horses, and cats.

The inventions also include articles of manufacture comprising package material containing one or more of the compounds or pharmaceutical compositions described herein. Then inventions also include articles of manufacture comprising package material containing one or more of the compounds or pharmaceutical compositions described herein, together with instructions for use in or on a subject in order to prevent and/or treat a cardioiovascular disease, disorder or condition. In one embodiment, the cardioiovascular disease, disorder or condition referred to in the instructions is associated with ischemia and/or oxidative stress. In another embodiment the cardioiovascular disease, disorder or condition referred to in the instructions is ischemic heart disease. In one embodiment, the cardioiovascular disease, disorder or condition referred to in the instructions is an acute coronary syndrome, e.g., unstable angina, STEMI, and/or NSTEMI. In another embodiment the cardioiovascular disease, disorder or condition referred to in the instructions is heart failure (any form). The instructions may be electronic and/or associated with a website.

The inventions also include methods of preparing a medicament for preventing or treating one or more of the cardioiovascular disease, disorder or conditions referenced herein, including, e.g., an acute coronary syndrome, heart failure, etc., comprising bringing together a therapeutically effective amount of a compound referenced herein, e.g., a Type-B natriuretic signal peptide fragment or a Type-B natriuretic signal peptide fragment analog or variant, and a pharmaceutically acceptable carrier. In one embodiment the Type-B natriuretic signal peptide fragment comprises a sequence selected from SEQ.ID.NOS:1 to 9. In another embodiment the Type-B natriuretic signal peptide fragment analog is a compound selected from one or more of Formulae I-VIII. In one embodiment the medicament is formulated for parenteral administration.

Compositions and methods of the invention for the prevention and/or treatment of a cardiovascular disorder, e.g., an acute coronary syndrome, heart failure, ischemic heart disease, etc., and related cardiovascular diseases, disorders and conditions involving ischemia and/or oxidative stress, also comprise administration of a Type-B natriuretic signal peptide fragment agent in series or in combination with (e.g., in physical combination, provided as a combined preparation) one or more other cardiovascular treatment agents. Such other cardiovascular treatment agents include nitrates, β-blockers, calcium channel blockers (particularly for stable or unstable angina, but also for heart failure in the case of β-blockers), diuretic agents, vasodilator agents, positive inotropes, ACE inhibitors and aldosterone antagonists, e.g. spironolactone (particularly for heart failure), blood thinning therapeutics (e.g., aspirin, heparins, warfarins) and nitroglycerin (particularly for MI).

Compositions and methods of the invention for the prevention and/or treatment of a cardiovascular disorder, e.g., an acute coronary syndrome, heart failure, ischemic heart disease, etc., and related cardiovascular diseases, disorders and conditions involving ischemia and/or oxidative stress, may also comprise administration of a Type-B natriuretic signal peptide fragment agent in series or in combination with (e.g., in physical combination, provided as a combined preparation) one or more anti-thrombolytic therapies (e.g., streptokinase inhibitors, anti-platelet thereapetuics, such as, for example, clopidogrel).

Compositions and methods of the invention for the prevention and/or treatment of a cardiovascular disorder, e.g., an acute coronary syndrome, heart failure, ischemic heart disease, etc., and related cardiovascular diseases, disorders and conditions involving ischemia and/or oxidative stress, may also comprise administration of a Type-B natriuretic signal peptide fragment agent in series or in combination with (e.g., in physical combination, provided as a combined preparation) a Type-B natriuretic peptide, including for example nesiritide, a recombinant form of Type-B natriuretic peptide.

In certain methods and compositions (including pharmaceutical compositions, formulations, articles of manufacture and kits) of the invention for the prevention and/or treatment of a cardiovascular disorder, e.g., an acute coronary syndrome, heart failure, ischemic heart disease, etc., and related cardiovascular diseases, disorders and conditions involving ischemia and/or oxidative stress, sub-therapeutically effective amounts of a Type-B natriuretic signal peptide fragment agent, and one or more other cardiovascular treatment agents are used or provided for combined administration (separately or jointly as a combined preparation) to provide a combined action that is therapeutically effective.

Thus, it will be understood that compositions and methods of the invention for the treatment of a cardiovascular disorder, e.g., an acute coronary syndrome, heart failure, ischemic heart disease, etc., and related cardiovascular diseases, disorders and conditions involving ischemia and/or oxidative stress, that employ a Type-B natriuretic signal peptide fragment agent, including active analogs thereof, and another cardiovascular therapeutic agent are disclosed. A Type-B natriuretic signal peptide fragment agent may be selected, for example, from the group consisting of BNPsp (17-26) (SEQ ID NO:1), BNPsp(17-25) (SEQ ID NO:2), BNPsp(17-24) (SEQ ID NO:3), BNPsp(17-23) (SEQ ID NO:4), BNPsp(17-22) (SEQ ID NO:5), BNPsp(17-21) (SEQ ID NO:6), BNPsp(17-20) (SEQ.ID.NO:7), BNPsp(17-19) (SEQ.ID.NO:8), and BNPsp(17-18) (SEQ.ID.NO:9), and active analogs thereof. In another embodiment, a Type-B natriuretic signal peptide agent may be selected from the group consisting of a sequence according any one of Formula I, Formula II, Formula III, Formula IV, Formula V, Formula VI, Formula VII and Formula VIII, and active analogs thereof. Optionally, a cardiovascular agent is selected, for example, from the group comprising or consisting essentially of nitrates, β-blockers, calcium channel blockers, diuretic agents, vasodilator agents, positive inotropes, ACE inhibitors, aldosterone antagonists, nitroglycerin, blood thinning agents, anti-thrombolytic agents, and Type-B natriuretic peptides.

Treatment of a subject as provided herein with one or more compounds or pharmaceutical compositions as described herein may comprise their simultaneous, separate, sequential or sustained administration.

Pharmaceutical compositions useful for preventing and/or treating a cardiovascular disorder, e.g., an acute coronary syndrome, heart failure, ischemic heart disease, etc., and related cardiovascular diseases, disorders and conditions involving ischemia and/or oxidative stress, are also provided in the form of a combined preparation, for example, as an admixture of two or more Type-B natriuretic signal peptide fragment agents.

The term "a combined preparation" includes not only physical combinations of compounds, but compounds provided as a "kit of parts" in the sense that the combination partners as defined above can be dosed independently or by use of different fixed combinations with distinguished amounts of the combination partners (a) and (b), i.e. simultaneously, separately or sequentially. The parts of the kit can then, for example, be administered simultaneously or chronologically staggered, that is at different time points and with equal or different time intervals for any part of the kit of parts.

In one embodiment, the inventions include a kit comprising one or more doses of a Type-B natriuretic signal peptide fragment agent, the kit comprising one or more of a syringe, a "pen" injector that delivers a metered dose, a needle-less injector, a liquid formulation, a lyophilized powder and a sterile liquid for reconstitution, a dry-powder inhaler, a buccal tablet, and a sublingual tablet.

In one embodiment a combined preparation is administered, wherein two or more separate compositions are administered to a subject, wherein the first composition comprises a therapeutically effective amount of a Type-B natriuretic signal peptide fragment agent and the second composition comprises a therapeutically effective amount of another cardiovascular therapeutic agent. In another embodiment a third composition is administered comprising a Type-B natriuretic signal peptide fragment agent or another cardiovascular therapeutic agent.

Thus, pharmaceutical compositions useful for preventing and/or treating a cardiovascular disorder, e.g., an acute coronary syndrome, heart failure, ischemic heart disease, etc., and related cardiovascular diseases, disorders and conditions involving ischemia and/or oxidative stress, are provided for combined, simultaneous, separate sequential or sustained administration. In one embodiment, a composition comprising or consisting essentially of a Type-B natriuretic signal peptide fragment agent is administered at or about the same time as another cardiovascular therapeutic agent(s). In one embodiment, a composition comprising a Type-B natriuretic signal peptide fragment agent is administered within at least about thirty minutes of another cardiovascular therapeutic agent(s). In one embodiment, a composition comprising a Type-B natriuretic signal peptide fragment agent is administered within at least about one hour of another cardiovascular therapeutic agent(s). In one embodiment, a composition comprising a Type-B natriuretic signal peptide fragment agent is administered within at least about 2-12 or 12 to 24 hours of another cardiovascular therapeutic agent (s). In one embodiment, a composition comprising a Type-B natriuretic signal peptide fragment agent is administered within at least about 24-48 hours of another cardiovascular therapeutic agent(s). In another embodiment the Type-B natriuretic signal peptide fragment agent and another cardiovascular therapeutic agent(s) are administered within about 1-8 hours of each other, within about one day of each other, or within about one week of each other.

In another aspect, the invention includes methods for administering a therapeutically effective amount of a Type-B natriuretic signal peptide fragment agent, alone or in combination with another cardiovascular therapeutic agent, formulated in a delayed release preparation, a slow release preparation, an extended release preparation, a controlled release preparation, and/or in a repeat action preparation to a subject having or at risk for developing a cardiovascular disorder, e.g., an acute coronary syndrome, heart failure, ischemic heart disease, etc., and related cardiovascular diseases, disorders and conditions involving ischemia and/or oxidative stress, or a related disorder or condition.

In certain other aspects, the invention also relates to methods of using such compositions to treat subjects suffering from or at risk for a cardiovascular disorder, e.g., an acute coronary syndrome, heart failure, ischemic heart disease, etc., and related cardiovascular diseases, disorders and conditions involving ischemia and/or oxidative stress, and related disorders and conditions.

In other aspects, the inventions include methods and compositions for preventing and/or treating a subject having or suspected of having or predisposed to, or at risk for, any diseases, disorders and/or conditions characterized in whole or in part by angina.

According to one aspect, the present invention is directed to methods of halting or decreasing or providing relief from the symptoms of a cardiovascular disorder, e.g., an acute coronary syndrome, heart failure, ischemic heart disease, etc., and related cardiovascular diseases, disorders and conditions involving ischemia and/or oxidative stress.

In another aspect, the invention provides a method of preventing and/or treating a cardiovascular disorder, e.g., an acute coronary syndrome, heart failure, ischemic heart disease, etc., and related cardiovascular diseases, disorders and conditions involving ischemia and/or oxidative stress, comprising administering to a subject in need thereof a composition comprising therapeutically effective amounts of a Type-B natriuretic signal peptide fragment agent agent, alone or together or in combination with another cardiovascular therapeutic agent, wherein said first agent is selected from the group consisting of BNPsp(17-26) (SEQ ID NO:1), BNPsp(17-25) (SEQ ID NO:2), BNPsp(17-24) (SEQ ID NO:3), BNPsp(17-23) (SEQ ID NO:4), BNPsp(17-22) (SEQ ID NO:5), BNPsp(17-21) (SEQ ID NO:6), BNPsp(17-20) (SEQ.ID.NO:7), BNPsp(17-19) (SEQ.ID.NO:8), and BNPsp(17-18) (SEQ.ID.NO:9) and sequences according any one of Formula I, Formula II, Formula III, Formula IV, Formula V, Formula VI, Formula VII and Formula VIII, and active analogs thereof, wherein the second cardiovascular agent is selected from the group comprising or consisting essentially of nitrates, β-blockers, calcium channel blockers, diuretic agents, vasodilator agents, positive inotropes, ACE inhibitors, aldosterone antagonists, nitroglycerin, blood thinning agents, anti-thrombolytic agents, and Type-B natriuretic peptides.

Methods of the invention include the sequential or simultaneous administration a first and second agents as described herein, either or both of which are provided in amounts or doses that are less that those used when the agent or agents are administered alone, i.e., when they are not administered in combination. Such lesser amounts of agents administered are typically from about one-twentieth to about one-tenth the amount or amounts of the agent when administered alone, and may be about one-eighth the amount, about one-sixth the amount, about one-fifth the amount, about one-fourth the amount, about one-third the amount, and about one-half the amount when administered alone.

In another aspect, the invention includes an article of manufacture comprising a vessel containing a therapeutically effective amount of a Type-B natriuretic signal peptide fragment agent(s), such as, for example, BNPsp(17-26) (SEQ ID NO:1), BNPsp(17-25) (SEQ ID NO:2), BNPsp (17-24) (SEQ ID NO:3), BNPsp(17-23) (SEQ ID NO:4), BNPsp(17-22) (SEQ ID NO:5), BNPsp(17-21) (SEQ ID NO:6), BNPsp(17-20) (SEQ.ID.NO:7), BNPsp(17-19) (SEQ.ID.NO:8), and BNPsp(17-18) (SEQ.ID.NO:9) and compounds selected from any one of Formula I, Formula II, Formula III, Formula IV, Formula V, Formula VI, Formula VII, and Formula VIII, and active analogs thereof, together or in physical combination with a second cardiovascular agent, such as one or more nitrates, β-blockers, calcium channel blockers, diuretic agents, vasodilator agents, positive inotropes, ACE inhibitors, aldosterone antagonists, nitroglycerin, blood thinning agents, anti-thrombolytic agents, and/or Type-B natriuretic peptides, and instructions for use, including use for the treatment of a subject as described herein.

The invention includes an article of manufacture comprising packaging material containing one or more dosage forms as described herein, wherein the packaging material has a label that indicates that the dosage form can be used for a subject having or suspected of having or predisposed to any of the diseases, disorders and/or conditions described or referenced herein, including acute coronary sydromes, ischemic heart disease, angina and heart failure.

The invention includes method of preparing a medicament for preventing and/or treating a cardiovascular disorder, e.g., an acute coronary syndrome, heart failure, ischemic heart disease, etc., and related cardiovascular diseases, disorders and conditions involving ischemia and/or oxidative stress, comprising bringing together and an amount of a Type-B natriuretic signal peptide fragment agent and a pharmaceutically acceptable carrier together with one or more other cardiovascular agents useful for preventing and/ or treating a cardiovascular disorder, e.g., an acute coronary syndrome, heart failure, ischemic heart disease, etc., and related cardiovascular diseases, disorders and conditions involving ischemia and/or oxidative stress.

The invention includes methods for the use of a therapeutically effective amount of a Type-B natriuretic signal peptide fragment agent(s) in the manufacture of a dosage form useful for preventing and/or treating a cardiovascular disorder, e.g., an acute coronary syndrome, heart failure, ischemic heart disease, etc., and related cardiovascular diseases, disorders and conditions involving ischemia and/or oxidative stress, and related disorders and conditions. Such dosage forms include, for example, oral delivery forms and formulations, well as other forms of delivery including forms for delivery by infusion, injection and instillation, and compositions and devices including slow-release, extended release, and delayed release compositions, depots and matrices, for example. Such dosage forms include those for the treatment of a subject as disclosed herein.

In certain other aspect, the invention provides a package comprising a Type-B natriuretic signal peptide fragment agent(s) together with instructions for use, alone or in combination with one or more other cardiovascular therapeutic agents for preventing and/or treating a cardiovascular disorder, e.g., an acute coronary syndrome, heart failure, ischemic heart disease, etc., and related cardiovascular diseases, disorders and conditions involving ischemia and/or oxidative stress, and related disorders and conditions.

In other aspects, the inventions provide for use of one or more of the compounds and compositions described herein in the manufacture of a medicament. In other aspects, the inventions provide for use of one or more of the compounds and compositions described herein in the manufacture of a medicament for use in the treatment of one or more of the diseases, disorders and conditions described herein. In other aspects, the inventions provide for use of one or more of the compounds, compositions and medicaments described and claimed herein in the treatment of a subject for one or more of the diseases, disorders and conditions described herein.

These and other aspects of the present inventions, which are not limited to or by the information in this Brief Summary, are provided below.

BRIEF DESCRIPTION OF FIGURES

This application contains at least one figure executed in color. Copies of this application with color drawing(s) will be provided upon request and payment of the necessary fee. A brief summary of each of the figures is provided below.

FIG. 1(A) shows that administration of 0.3 nMol and 1 nMol human BNPsp(17-26) either before (pre) or after (IDR) a 40 minute period of ischemia improves the contractile function of the left ventricle as assessed by developed pressure. These effects were most pronounced at 0.3 nMol pre and 1 nMol. IDR. FIG. 1(B) documents vascular reactivity, as assessed by perfusion pressure in the same hearts as in FIG. 1A. Perfusion pressures during the reperfusion phase after ischemia are beneficially reduced by pre or IDR treatment with BNPsp(17-26). FIG. 1(C) shows significant reductions in troponin I release (a biomarker of cardiac cell necrosis) during reperfusion resulting from IDR administration of human BNPsp (17-26). FIG. 1(D) shows concomitant improvements in reperfusion myoglobin levels in the same samples described in FIG. 1C.

FIG. 2 demonstrates in vivo tolerance and lack of haemodynamic effects to human BNPsp(17-26) administration in normal, healthy sheep. FIG. 2(A) shows the lack of response in cardiac output in sheep 1 when given constant infusion of human BNPsp(17-26) at 10 ng/kg/min and 100 kg/ng/min, compared with control infusion (saline). Such a response is indicative of a well tolerated agent. FIG. 2(B) shows the same lack of response of cardiac output in sheep 2, when the same doses of BNPsp(17-26) as in FIG. 2A were administered.

FIG. 7A (upper panel) shows the perfusion pressure and cumulative troponin release in isolated hearts given BNPsp (17-26) during reperfusion after ischemia.

DETAILED DESCRIPTION

Figure 1:
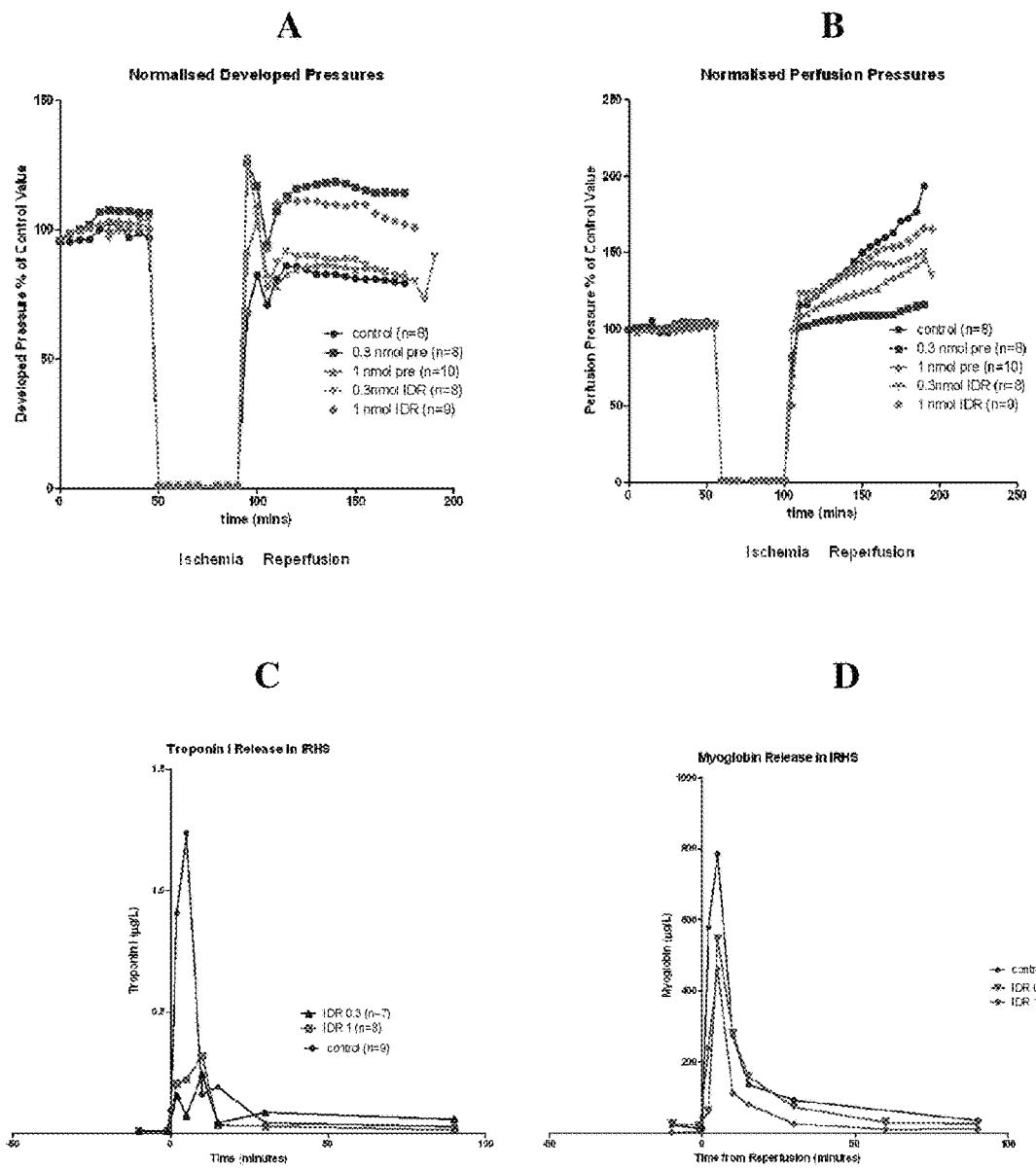
FIG. 1 demonstrates the beneficial effects of human BNPsp(17-26) administration in an isolated rat heart model of ischemia reperfusion injury.

Practice of the present inventions may include or employ various conventional techniques of molecular biology (including recombinant techniques), microbiology, cell biology, biochemistry, nucleic acid chemistry, and immunology, which are within the skill of the art. Such techniques are explained fully in the literature, and include but are not limited to, by way of example only, Molecular Cloning: A Laboratory Manual, second edition (Sambrook et al., 1989) and Molecular Cloning: A Laboratory Manual, third edition (Sambrook and Russel, 2001), jointly and individually referred to herein as "Sambrook"; Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987, including supplements through 2001); PCR: The Polymerase Chain Reaction, (Mullis et al., eds., 1994); Current Protocols in Immunology (J. E. Coligan et al., eds., 1991); The Immunoassay Handbook (D. Wild, ed., Stockton Press NY, 1994); Bioconjugate Techniques (Greg T. Hermanson, ed., Academic Press, 1996); Methods of Immunological Analysis (R. Masseyeff, W. H. Albert, and N. A. Staines, eds., Weinheim: VCH Verlags gesellschaft mbH, 1993), Harlow and Lane (1988) Antibodies, A Laboratory Manual, Cold Spring Harbor Publications, New York, and Harlow and Lane (1999) Using Antibodies: A Laboratory Manual Cold Spring Harbor Laboratory Press, Cold Spring Harbor, N.Y. (jointly and individually referred to herein as Harlow and Lane), Beaucage et al. eds., Current Protocols in Nucleic Acid Chemistry John Wiley & Sons, Inc., New York, 2000); and Agrawal, ed., Protocols for Oligonucleotides and Analogs, Synthesis and Properties Humana Press Inc., New Jersey, 1993)

It is to be understood that the inventions are not limited to the particular methodology, protocols, constructs, and reagents described herein and as such may vary. It is also to be understood that the terminology used herein is for the purpose of describing particular embodiments only, and is not intended to limit the scope of the present invention, which will be limited only by the appended claims. As used herein and in the appended claims, the singular forms "a," "an," and "the" include plural reference unless the context clearly indicates otherwise. Thus, for example, reference to a "Type-B natriuretic signal peptide fragment" is a reference to one or more such peptides and includes equivalents thereof now known or later developed. Unless defined otherwise, all technical and scientific terms used herein have the same meaning as commonly understood to one of ordinary skill in the art to which the inventions belong. Although any methods, devices, and materials similar or equivalent to those described herein can be used in the practice or testing of the invention, the preferred methods, devices and materials are now described. It is intended that reference to a range of numbers disclosed herein (for example 1 to 12) also incorporates reference to all related numbers within that range (for example, 1, 1.1, 2, 3, 3.9, 4, 5, 6, 6.5, 7, 8, 9.5, 10, 11 and 12) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner. The following terms have the following meanings when used herein.

Amino acids used in compounds provided herein (e.g. peptides and proteins) can be genetically encoded amino acids, naturally occurring non-genetically encoded amino acids, or synthetic amino acids. Both L- and D-enantiomers of any of the above can be utilized in the compounds. The following abbreviations may be used herein for the following genetically encoded amino acids (and residues thereof): alanine (Ala, A); arginine (Arg, R); asparagine (Asn, N); aspartic acid (Asp, D); cyteine (Cys, C); glycine (Gly, G); glutamic acid (Glu, E); glutamine (Gln, Q); histidine (His, H); isoleucine (Ile, I); leucine (Leu, L); lysine (Lys, K); methionine (Met, M); phenylalanine (Phe, F); proline (Pro, P); serine (Ser, S); threonine (Thr, T); tryptophan (Trp, W); tyrosine (Tyr, Y); and valine (Val, V).

Certain commonly encountered amino acids that are not genetically encoded and that can be present in active compounds of the invention include, but are not limited to, β-alanine (b-Ala) and other omega-amino acids such as 3-aminopropionic acid (Dap), 2,3-diaminopropionic acid (Dpr, Z), 4-aminobutyric acid and so forth; α-aminoisobutyric acid (Aib); ε-aminohexanoic acid (Aha); δ-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle, J); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (Me-Val); homocysteine (hCys); 3-benzothiazol-2-yl-alanine (BztAla, B); and homoserine (hSer). Additional amino acid analogs contemplated include phosphoserine, phosphothreonine, phosphotyrosine, hydroxyproline, gamma-carboxyglutamate, hippuric acid, octahydroindole-2-carboxylic acid, statine, α-methyl-alanine, para-benzoyl-phenylalanine, propargylglycine, and sarcosine. Peptides that are encompassed within the scope of the invention can have any of the foregoing amino acids in the L- or D-configuration, or any other amino acid described herein or known in the art, whether currently or in the future, whilst retaining a biological activity.

Amino acids that are substitutable for each other generally reside within similar classes or subclasses. As known to one of skill in the art, amino acids can be placed into different classes depending primarily upon the chemical and physical properties of the amino acid side chain. For example, some amino acids are generally considered to be hydrophilic or polar amino acids and others are considered to be hydrophobic or nonpolar amino acids. Polar amino acids include amino acids having acidic, basic or hydrophilic side chains and nonpolar amino acids include amino acids having aromatic or hydrophobic side chains. Nonpolar amino acids may be further subdivided to include, among others, aliphatic amino acids. The definitions of the classes of amino acids as used herein are as follows:

"Nonpolar Amino Acid" refers to an amino acid having a side chain that is uncharged at physiological pH, that is not polar and that is generally repelled by aqueous solution. Examples of genetically encoded hydrophobic amino acids include Ala, Ile, Leu, Met, Trp, Tyr and Val. Examples of non-genetically encoded nonpolar amino acids include t-BuA, Cha and Nle.

"Aromatic Amino Acid" refers to a nonpolar amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 3-benzothiazol-2-yl-alanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Aliphatic Amino Acid" refers to a nonpolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Polar Amino Acid" refers to a hydrophilic amino acid having a side chain that is charged or uncharged at physiological pH and that has a bond in which the pair of electrons shared in common by two atoms is held more closely by one of the atoms. Polar amino acids are generally hydrophilic, meaning that they have an amino acid having a side chain that is attracted by aqueous solution. Examples of genetically encoded polar amino acids include asparagine, cysteine, glutamine, lysine and serine. Examples of non-genetically encoded polar amino acids include citrulline, homocysteine, N-acetyl lysine and methionine sulfoxide.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include ornithine, 2,3-diaminopropionic acid, 2,4-diaminobutyric acid and homoarginine.

"Ionizable Amino Acid" refers to an amino acid that can be charged at a physiological pH. Such ionizable amino acids include acidic and basic amino acids, for example, D-aspartic acid, D-glutamic acid, D-histidine, D-arginine, D-lysine, D-hydroxylysine, D-ornithine, L-aspartic acid, L-glutamic acid, L-histidine, L-arginine, L-lysine, L-hydroxylysine or L-ornithine.

As will be appreciated by those having skill in the art, the above classifications are not absolute. Several amino acids exhibit more than one characteristic property, and can therefore be included in more than one category. For example, tyrosine has both a nonpolar aromatic ring and a polar hydroxyl group. Thus, tyrosine has several characteristics that could be described as nonpolar, aromatic and polar. However, the nonpolar ring is dominant and so tyrosine is generally considered to be nonpolar. Similarly, in addition to being able to form disulfide linkages, cysteine also has nonpolar character. Thus, while not strictly classified as a hydrophobic or nonpolar amino acid, in many instances cysteine can be used to confer hydrophobicity or nonpolarity to a peptide.

In some embodiments, polar amino acids contemplated by the present invention include, for example, arginine, asparagine, aspartic acid, cysteine, glutamic acid, glutamine, histidine, homocysteine, lysine, hydroxylysine, ornithine, serine, threonine, and structurally related amino acids. In one embodiment the polar amino is an ionizable amino acid such as arginine, aspartic acid, glutamic acid, histidine, hydroxylysine, lysine, or ornithine.

Examples of polar or nonpolar amino acid residues that can be utilized include, for example, alanine, valine, leucine, methionine, isoleucine, phenylalanine, tryptophan, tyrosine and the like.

As used herein, a "cardiovascular disorder" is any cardiovascular disease, disorder or condition that involves or may be characterized at least in part by oxidative stress and/or ischemia.

During physiological processes molecules undergo chemical changes involving reducing and oxidizing reactions. A molecule with an unpaired electron can combine with a molecule capable of donating an electron. The donation of an electron is termed as oxidation whereas the gaining of an electron is called reduction. Reduction and oxidation can render the reduced molecule unstable and make it free to react with other molecules to cause damage to cellular and sub-cellular components such as membranes, proteins and DNA. As used herein, "oxidative stress" refers to excessive production of reactive oxidant species (ROS) resulting in oxidative stress/nitrosative stress, a process that is an important mediator of cell damage. Important aspects of redox imbalance that triggers the activity of a number of signaling pathways including transcription factors activity, a process that is ubiquitous in cardiovascular disease related to ischemia/reperfusion injury, for example. Reactive oxidant species can originate from a variety of sources such as nitric oxide (NO) synthase (NOS), xanthine oxidases (XO), the cyclooxygenases, nicotinamide adenine dinucleotide phosphate (NAD(P)H) oxidase isoforms and metal-catalyzed reactions. These include free radicals such as superoxide anion ($O_2.^-$), hydroxyl radical (HO.), lipid radicals ($ROO^-$) and nitric oxide (NO). Other reactive oxygen species, for example, hydrogen peroxide ($H_2O_2$), peroxynitrite ($ONOO^-$) and hypochlorous acid (HOCl), although are not free radicals but have oxidizing effects that contribute to oxidative stress.

"Ischemia" is a condition that occurs when blood flow and oxygen are diminished in a particular part of the body. Cardiac ischemia is the name for this condition when the heart is the body part targeted. Ischemic heart disease is a term that covers heart issues caused by narrowing of the arteries. With arteries narrowed, less blood and oxygen are able to reach the heart muscle. This is also referred to as coronary artery disease and coronary heart disease and may ultimately lead to heart attack. Ischemia often causes chest pain or discomfort known as angina pectoris. People with angina also may have undiagnosed episodes of silent ischemia.

Cardiovascular disorders include, for example, heart failure (including congestive heart failures and other forms of heart failure noted anywhere herein) and acute coronary syndromes (including Q-wave MI, STEMI, non-Q-wave MI, NSTEMI and unstable angina) and ischemic heart disease. Cardiovascular disorders also include diseases, disorders and conditions involving the heart or blood vessels in which Type-B natriuretic peptide is elevated within a clinically relevant timeframe. Cardiovascular disorders also include diseases, disorders and conditions involving the heart or blood vessels in which one or more of cardiac troponin I, cardiac troponin T, creatine kinase-MB, Type-A and/or Type-B natriuretic peptide signal peptides or signal peptide fragments, uric acid, C-reactive protein and/or osteoprotegerin is/are present in increased levels in clinically relevant timeframes. Other cardiovascular disorders include non-Q-wave cardiac necrosis.

As used herein, a patient suffering from "unstable angina" denotes a patient who has one or more of the following symptoms and signs: (1) ST segment depression, as measured by ECG; (2) slightly elevated troponin T levels, of no more than 0.1 ng/ml; or (3) slightly elevated troponin I levels, of no more than 0.4 ng/ml. In contrast to Q-wave MI, CK-MB and LDH levels are typically not elevated during unstable angina. Also in contrast to Q-wave MI, a patient with unstable angina typically has no ST segment elevation nor any pathological Q-wave. Finally, unstable angina can be diagnosed solely on the basis of chest pain, typically chest pain lasting longer than 15 minutes, chest pain at rest, or chest pain following minimal exertion and that is poorly responsive to sublingual nitrates. Alternatively, even in the absence of chest pain, a patient can be diagnosed with unstable angina if previously diagnosed with ischemic heart disease or is considered to be at strong risk for developing ischemic heart disease, and who presents with nausea, shortness of breath, palpitations, or dizziness. Furthermore, the skilled artisan will understand that the diagnosis of unstable angina is one of medical judgment.

As used herein, "ischemic heart disease" denotes disease of cardiac tissue that results from a decreased oxygen supply to the cardiac tissue that is due to reduced coronary artery blood flow. Typically, this reduced blood flow results from the partial or complete obstruction of blood vessels that service the heart. A diagnosis of ischemic heart disease can be based on the presence of chronic, stable angina, elicited by exercise (also known as "exertional angina") that is relieved by sublingual nitrates. A diagnosis of ischemic heart disease also can be based on an ECG reading that is consistent with ischemic heart disease, such as one exhibiting ST segment deviations and/or T wave inversions.

As used herein, "Type-B natriuretic signal peptide fragment agent" in one aspect refers to a fragment of a Type-B natriuretic signal peptide from any species, including murine, bovine, ovine, porcine, equine, avian, and preferably human, in native sequence or in a genetically engineered form, and from any source, whether natural, synthetic, or recombinantly produced, having one or more of the biologic or therapeutic activities described herein. The term "Type-B natriuretic signal peptide fragment agent" also includes pharmaceutically acceptable salts and prodrugs, and prodrugs of the salts, polymorphs, hydrates, solvates, biologically-active fragments, biologically active variants and stereoisomers of the naturally-occurring any Type-B natriuretic signal peptide fragment, as well as agonist and mimetic variants of any naturally-occurring Type-B natriuretic signal peptide fragment and active analogs (e.g., peptides containing, for example, specific deletions or other modifications that maintain biological activity) and polypeptide fusions thereof. Fusions comprising additional amino acids at the amino terminus, carboxyl terminus, or both, are encompassed by the term "Type-B natriuretic signal peptide fragment agent." Fusions comprising additional amino acids at the carboxyl terminus of a Type-B natriuretic signal peptide fragment, or other Type-B natriuretic signal peptide fragment agent (including, for example, variants and analogs of a Type-B natriuretic signal peptide fragment), are preferred. Exemplary Type-B natriuretic signal peptide fragment agents include BNPsp(17-26) (SEQ ID NO:1), BNPsp(17-25) (SEQ ID NO:2), BNPsp(17-24) (SEQ ID NO:3), BNPsp(17-23) (SEQ ID NO:4), BNPsp(17-22) (SEQ ID NO:5), BNPsp(17-21) (SEQ ID NO:6), BNPsp(17-20) (SEQ.ID.NO:7), BNPsp(17-19) (SEQ.ID.NO:8), and BNPsp(17-18) (SEQ.ID.NO:9). Other Type-B natriuretic signal peptide fragment agents include peptides according any of Formula I, Formula II, Formula III, Formula IV, Formula V, Formula VI, Formula VII and Formula VIII.

The art is familiar with modification of peptides, for example, by polymer conjugation or glycosylation. The term "Type-B natriuretic signal peptide fragment agent" includes modified peptides including peptides conjugated to a polymer such as PEG, and may be comprised of one or more additional derivitizations of cysteine, lysine, or other residues. In addition, the Type-B natriuretic signal peptide fragment agent may comprise a linker or polymer, wherein the amino acid to which the linker or polymer is conjugated may be a non-natural amino acid according to the present invention, or may be conjugated to a naturally encoded amino acid utilizing techniques known in the art such as coupling to lysine or cysteine.

Substitutions, deletions, modifications or additions of amino acids described herein in reference to compounds of the invention, for example, SEQ ID NO: 1, 2, 3, 4, 5, 6, 7, 8, 9 or other peptides as defined, for example, in Formula I, Formula II, Formula III, Formula IV, Formula V, Formula VI, Formula VII and Formula VIII, are intended to also refer to substitutions, deletions, modifications or additions in corresponding positions in fusions, variants, fragments, conjugations, etc.

The term "Type-B natriuretic signal peptide fragment agent" also encompasses homodimers, heterodimers, homomultimers, and heteromultimers that are linked, including but not limited to those linked directly via non-naturally encoded amino acid side chains, either to the same or different non-naturally encoded amino acid side chains, to naturally-encoded amino acid side chains, or indirectly via a linker. Exemplary linkers include small organic compounds, water soluble polymers of a variety of lengths such as poly(ethylene glycol) or polydextran or polypeptides of various lengths.

The term "linker" is used herein to refer to groups or bonds that normally are formed as the result of a chemical reaction and typically are covalent linkages. Hydrolytically stable linkages means that the linkages are substantially stable in water and do not react with water at useful Ph values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrozone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "active," "biologically active" or "biologically active agent" when used herein means any substance which can affect any physical or biochemical properties of a biological system, pathway, molecule, or interaction relating to an organism, including but not limited to, viruses, bacteria, bacteriophage, transposons, prions, insects, fungi, plants, animals, and humans. In particular, as used herein, biologically active molecules include, but are not limited to, any substance intended for cure, mitigation, treatment, or prevention of cardiovascular disorder in humans or other animals, or to otherwise enhance physical or mental well-being of humans or animals.

As used herein, the term "water soluble polymer" refers to any polymer that is soluble in aqueous solvents. Linkage of water soluble polymers to a Type-B natriuretic signal peptide fragment agent, e.g., Type-B natriuretic signal peptide fragments, can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding, and altered receptor dimerization or multimerization. The water soluble polymer may or may not have its own biological activity, and may be utilized as a linker for attaching Type-B natriuretic signal peptide fragment agents, e.g., Type-B natriuretic signal peptide fragments, to other substances, including but not limited to one or more Type-B natriuretic signal peptide fragment agents, e.g., Type-B natriuretic signal peptide fragments, or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and al pha-beta-poly[(2-hydroxyethyl)-DL-aspartamide, and the like, or mixtures thereof. Examples of such water soluble polymers include, but are not limited to, polyethylene glycol and serum albumin.

As used herein, the term "polyalkylene glycol" or "poly (alkene glycol)" refers to polyethylene glycol (poly(ethylene glycol)), polypropylene glycol, polybutylene glycol, and derivatives thereof. The term "polyalkylene glycol" and/or "polyethylene glycol" encompasses both linear and branched polymers and average molecular weights of between 0.1 kDa and 100 kDa or more. Other exemplary embodiments are listed, for example, in commercial supplier catalogs, such as Shearwater Corporation's catalog "Polyethylene Glycol and Derivatives for Biomedical Applications" (2001).

As used herein, the term "modified serum half-life" means an increased circulating half-life of a modified Type-B natriuretic signal peptide fragment agents, e.g., a Type-B natriuretic signal peptide fragment, relative to its non-modified form. Serum half-life is measured by taking blood samples at various time points after administration of a Type-B natriuretic signal peptide fragment agent, e.g., a Type-B natriuretic signal peptide fragment, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold or more.

The term "modified therapeutic half-life" as used herein means an increase in the half-life of the therapeutically effective amount of a modified Type-B natriuretic signal peptide fragment agent, e.g., a Type-B natriuretic signal peptide fragment, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule.

The term "isolated," when applied to a peptide, denotes that the peptide is free of at least some of the cellular or other biological components with which it is associated in the natural state, or that the peptide has been concentrated to a level greater than the concentration of its in vivo or in vitro production. It can be in a homogeneous or substantially homogenous state. Isolated substances can be in either a dry or semi-dry state, or in solution, including but not limited to, an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography, for example.

By "substantially pure" is meant a degree of purity of total Type-B natriuretic signal peptide agent, e.g., BNPsp(17-26) (SEQ ID NO:1), to total protein where there is at least 70% Type-B natriuretic signal peptide agent, more preferably at least 80%, and even more preferably increasing to at least 90%, 95% or 99%. A particularly preferred purity is at least 95%. By "essentially pure" is meant that the composition is at least 90% or more pure for the desired Type-B natriuretic signal peptide agent. A peptide which is the predominant species present in a preparation is also substantially purified.

The term "effective amount" as used herein refers to that amount of the Type-B natriuretic signal peptide fragment agent being administered that will relieve to some extent one or more of the symptoms of the disease, condition or disorder being treated. Compositions containing the Type-B natriuretic signal peptide fragment agents described herein can be administered for prophylactic, enhancing, and/or therapeutic treatments.

As used herein, "subject" refers to any mammal, including humans, domestic and farm animals, and zoo, sports, or pet animals, such as dogs, horses, cats, sheep, pigs, cows, etc. The preferred mammal herein is a human, including adults, children, and the elderly. Preferred sports animals are horses and dogs. Preferred pet animals are dogs and cats.

As used herein, "preventing" means preventing in whole or in part, ameliorating or controlling, reducing, lessening, or decreasing, or retarding or halting.

As used herein, a "therapeutically effective amount" in reference to the compounds or compositions of the instant invention refers to the amount sufficient to induce a desired biological, pharmaceutical, or therapeutic result. That result can be alleviation of one or more of the signs, symptoms, or causes of a disease or disorder or condition, or any other desired alteration of a biological system. In the present invention, the result will involve the treatment, prevention and/or reduction of one or more of symptoms of a cardiovascular disorder, including, for example, an acute coronary syndrome, a heart failure, an ischemic heart disease, and angina and any cardiovascular disorder, disease, or condition that involves ischemia and/or oxidative stress.

As used herein, the terms "treating" and "treatment" refer to both therapeutic treatment and prophylactic or preventative measures.

"Analogs" or "peptide analogs" refer to the compounds with properties analogous to those of the template peptide and may be non-peptide drugs. "Peptidomimetics" (also known as "mimetic peptides"), which include peptide-based compounds, also include such non-peptide based compounds such as peptide analogs. Peptidomimetics that are structurally similar to therapeutically useful peptides may be used to produce an equivalent or enhanced therapeutic or prophylactic effect. Generally, peptidomimetics are structurally identical or similar to a paradigm polypeptide (i.e., a polypeptide that has a biological or pharmacological function or activity), but can also have one or more peptide linkages optionally replaced by a linkage selected from the group consisting of, for example, —CH2NH—, —CH2S—, —CH2-CH2-, —CH═CH— (cis and trans), —COCH2-, —CH(OH)CH2-, and —CH2SO—. The mimetic can be either entirely composed of natural amino acids, or non-natural analogues of amino acids, or, is a chimeric molecule of partly natural peptide amino acids and partly non-natural analogs of amino acids. The mimetic can also comprise any amount of natural amino acid conservative substitutions as long as such substitutions also do not substantially alter mimetic activity.

In general, the term "peptide" refers to any polymer of two or more individual amino acids (whether or not naturally occurring) linked via peptide bonds, as occur when the carboxyl carbon atom of the carboxylic acid group bonded to the alpha-carbon of one amino acid (or amino acid residue) becomes covalently bound to the amino nitrogen atom of the amino group bonded to the alpha-carbon of an adjacent amino acid. These peptide bond linkages, and the atoms comprising them (i.e., alpha-carbon atoms, carboxyl carbon atoms (and their substituent oxygen atoms), and amino nitrogen atoms (and their substituent hydrogen atoms)) form the "polypeptide backbone" of the protein. In addition, as used herein, the terms "polypeptide" and "peptide" may be used interchangeably. Similarly, protein fragments, analogs, derivatives, and variants are may be referred to herein as "peptides" or "peptide agents.". The term "fragment" of a peptide refers to a polypeptide comprising fewer than all of the amino acid residues of the peptide.

As used herein, "simultaneously" is used to mean that the one or more agents of the invention are administered concurrently, whereas the term "in combination" is used to mean they are administered, if not simultaneously or in physical combination, then "sequentially" within a timeframe that they both are available to act therapeutically.

Thus, administration "sequentially" may permit one agent to be administered within minutes (for example, 1, 2, 3, 4, 5, 10, 15, 20, 25, 30) minutes or a matter of hours, days, weeks or months after the other provided that both the Type-B natriuretic signal peptide fragment agent and another cardiovascular therapeutic agent, for example, are concurrently present in effective amounts. The time delay between administration or administrations of the components will vary depending on the exact nature of the components, the interaction therebetween, and their respective half-lives.

Type-B Natriuretic Signal Peptide Fragment Agents

Type-B natriuretic signal peptide fragment agents of the invention described herein are capable of modulating one or more of the symtoms of a cardiovascular disorder. Preferably, the cardiovascular disorder is an acute coronary syndrome, but others are intended as described herein.

Compounds of the invention, which in a non-limiting preferred embodiment are isolated or substantially pure, include the following peptides:

| | |
|---|---|
| LHLAFLGGRS | (SEQ.ID.NO: 1) |
| LHLAFLGGR | (SEQ.ID.NO: 2) |
| LHLAFLGG | (SEQ.ID.NO: 3) |
| LHLAFLG | (SEQ.ID.NO: 4) |
| LHLAFL | (SEQ.ID.NO: 5) |
| LHLAF | (SEQ.ID.NO: 6) |
| LHLA | (SEQ.ID.NO: 7) |
| LHL | (SEQ.ID.NO: 8) |
| LH | (SEQ.ID.NO: 9) |

Compounds of the invention, which in a non-limiting preferred embodiment are isolated or substantially pure, also include peptides according to the following Formula I:

$$\text{LHX}_1\text{X}_2\text{X}_3\text{X}_4\text{X}_5\text{X}_6\text{X}_7\text{X}_8 \qquad \text{(SEQ ID NO: 10)}$$

wherein $X_1$ is Norleucine, Ile, Val, Met, Ala, Phe or Gly; $X_2$ is Val, Leu, Ile or Gly; $X_3$ is Leu, Val, Ile, Ala, Tyr or Gly; $X_4$ is Norleucine, Ile, Val, Met, Ala, Phe or Gly; $X_5$ is Pro, Ala, Arg or Ser; $X_6$ is Pro, Ala, Arg or Ser; $X_7$ is Arg, Gln, Asn or Gly; and $X_8$ is Thr or Gly.

Compounds of the invention, which in a non-limiting preferred embodiment are isolated or substantially pure, also include peptides according to the following Formula II:

$$\text{LHX}_1\text{X}_2\text{X}_3\text{X}_4\text{X}_5\text{X}_6\text{X}_7 \qquad \text{(SEQ ID NO: 11)}$$

wherein $X_1$ is Norleucine, Ile, Val, Met, Ala, Phe or Gly; $X_2$ is Val, Leu, Ile or Gly; $X_3$ is Leu, Val, Ile, Ala, Tyr or Gly; $X_4$ is Norleucine, Ile, Val, Met, Ala, Phe or Gly; $X_5$ is Pro, Ala, Arg or Ser; $X_6$ is Pro, Ala, Arg or Ser; and $X_7$ is Arg, Gln, Asn or Gly; provided that where $X_1$ is Norleucine, Ile, Val, Met, Ala, Phe or Gly, $X_2$ can also be Ala, $X_3$ can also be Phe, $X_4$ can also be Leu, $X_5$ can also be Gly, $X_6$ can also be Gly, and $X_7$ can also be Arg;

where $X_2$ is Val, Leu or Ile or Gly, $X_1$ can also be Leu, $X_3$ can also be Phe, $X_4$ can also be Leu, $X_5$ can also be Gly, $X_6$ can also be Gly, and $X_7$ can also be Arg;

where $X_3$ is Leu, Val, Ile, Ala, Tyr or Gly, $X_1$ can also be Leu, $X_2$ can also be Ala, $X_4$ can also be Leu, $X_5$ can also be Gly, $X_6$ can also be Gly, and $X_7$ can also be Arg;

where $X_4$ is Norleucine, Ile, Val, Met, Ala, Phe or Gly, $X_1$ can also be Leu, $X_2$ can also be Ala, $X_3$ can also be Phe, $X_5$ can also be Gly, $X_6$ can also be Gly, and $X_7$ can also be Arg;

where $X_5$ is Pro, Ala, Arg or Ser, $X_1$ can also be Leu, $X_2$ can also be Ala, $X_3$ can also be Phe, $X_4$ can also be Leu, $X_6$ can also be Gly, and $X_7$ can also be Arg;

where $X_6$ is Pro, Ala, Arg or Ser, $X_1$ can also be Leu, $X_2$ can also be Ala, $X_3$ can also be Phe, $X_4$ can also be Leu, $X_5$ can also be Gly, and $X_7$ can also be Arg;

where $X_7$ is Lys, Gln, Asn or Gly, $X_1$ can also be Leu, $X_2$ can also be Ala, $X_3$ can also be Phe, $X_4$ can also be Leu, $X_5$ can also be Gly, and $X_6$ can also be Gly.

Compounds of the invention, which in a non-limiting preferred embodiment are isolated or substantially pure, also include peptides according to the following Formula III:

$$\text{LHX}_1\text{X}_2\text{X}_3\text{X}_4\text{X}_5\text{X}_6 \quad \text{(SEQ ID NO: 12)}$$

wherein $X_1$ is Norleucine, Ile, Val, Met, Ala, Phe or Gly; $X_2$ is Val, Leu, Ile or Gly; $X_3$ is Leu, Val, Ile, Ala, Tyr or Gly; $X_4$ is Norleucine, Ile, Val, Met, Ala, Phe or Gly; $X_5$ is Pro, Ala, Arg or Ser; and $X_6$ is Pro, Ala, Arg or Ser; provided that where $X_1$ is Norleucine, Ile, Val, Met, Ala, Phe or Gly, $X_2$ can also be Ala, $X_3$ can also be Phe, $X_4$ can also be Leu, $X_5$ can also be Gly, $X_6$ can also be Gly, and $X_7$ can also be Arg;

where $X_2$ is Val, Leu or Ile or Gly, $X_1$ can also be Leu, $X_3$ can also be Phe, $X_4$ can also be Leu, $X_5$ can also be Gly, $X_6$ can also be Gly, and $X_7$ can also be Arg;

where $X_3$ is Leu, Val, Ile, Ala, Tyr or Gly, $X_1$ can also be Leu, $X_2$ can also be Ala, $X_4$ can also be Leu, $X_5$ can also be Gly, $X_6$ can also be Gly, and $X_7$ can also be Arg;

where $X_4$ is Norleucine, Ile, Val, Met, Ala, Phe or Gly, $X_1$ can also be Leu, $X_2$ can also be Ala, $X_3$ can also be Phe, $X_5$ can also be Gly, $X_6$ can also be Gly, and $X_7$ can also be Arg;

where $X_5$ is Pro, Ala, Arg or Ser, $X_1$ can also be Leu, $X_2$ can also be Ala, $X_3$ can also be Phe, $X_4$ can also be Leu, $X_6$ can also be Gly, and $X_7$ can also be Arg;

where $X_6$ is Pro, Ala, Arg or Ser, $X_1$ can also be Leu, $X_2$ can also be Ala, $X_3$ can also be Phe, $X_4$ can also be Leu, $X_5$ can also be Gly, and $X_7$ can also be Arg.

Compounds of the invention, which in a non-limiting preferred embodiment are isolated or substantially pure, also include peptides according to the following Formula IV:

$$\text{LHX}_1\text{X}_2\text{X}_3\text{X}_4\text{X}_5 \quad \text{(SEQ ID NO: 13)}$$

wherein $X_1$ is Norleucine, Ile, Val, Met, Ala, Phe or Gly; $X_2$ is Val, Leu, Ile or Gly; $X_3$ is Leu, Val, Ile, Ala, Tyr or Gly; $X_4$ is Norleucine, Ile, Val, Met, Ala, Phe or Gly; and $X_5$ is Pro, Ala, Arg or Ser; provided that where $X_1$ is Norleucine, Ile, Val, Met, Ala, Phe or Gly, $X_2$ can also be Ala, $X_3$ can also be Phe, $X_4$ can also be Leu, $X_5$ can also be Gly, $X_6$ can also be Gly, and $X_7$ can also be Arg;

where $X_2$ is Val, Leu or Ile or Gly, $X_1$ can also be Leu, $X_3$ can also be Phe, $X_4$ can also be Leu, $X_5$ can also be Gly, $X_6$ can also be Gly, and $X_7$ can also be Arg;

where $X_3$ is Leu, Val, Ile, Ala, Tyr or Gly, $X_1$ can also be Leu, $X_2$ can also be Ala, $X_4$ can also be Leu, $X_5$ can also be Gly, $X_6$ can also be Gly, and $X_7$ can also be Arg;

where $X_4$ is Norleucine, Ile, Val, Met, Ala, Phe or Gly, $X_1$ can also be Leu, $X_2$ can also be Ala, $X_3$ can also be Phe, $X_5$ can also be Gly, $X_6$ can also be Gly, and $X_7$ can also be Arg;

where $X_5$ is Pro, Ala, Arg or Ser, $X_1$ can also be Leu, $X_2$ can also be Ala, $X_3$ can also be Phe, $X_4$ can also be Leu, $X_6$ can also be Gly, and $X_7$ can also be Arg.

Compounds of the invention, which in a non-limiting preferred embodiment are isolated or substantially pure, also include peptides according to the following Formula V:

$$\text{LHX}_1\text{X}_2\text{X}_3\text{X}_4 \quad \text{(SEQ ID NO: 14)}$$

wherein $X_1$ is Norleucine, Ile, Val, Met, Ala, Phe or Gly; $X_2$ is Val, Leu, Ile or Gly; $X_3$ is Leu, Val, Ile, Ala, Tyr or Gly; and $X_4$ is Norleucine, Ile, Val, Met, Ala, Phe or Gly; provided that where $X_1$ is Norleucine, Ile, Val, Met, Ala, Phe or Gly, $X_2$ can also be Ala, $X_3$ can also be Phe, $X_4$ can also be Leu, $X_5$ can also be Gly, $X_6$ can also be Gly, and $X_7$ can also be Arg;

where $X_2$ is Val, Leu or Ile or Gly, $X_1$ can also be Leu, $X_3$ can also be Phe, $X_4$ can also be Leu, $X_5$ can also be Gly, $X_6$ can also be Gly, and $X_7$ can also be Arg;

where $X_3$ is Leu, Val, Ile, Ala, Tyr or Gly, $X_1$ can also be Leu, $X_2$ can also be Ala, $X_4$ can also be Leu, $X_5$ can also be Gly, $X_6$ can also be Gly, and $X_7$ can also be Arg;

where $X_4$ is Norleucine, Ile, Val, Met, Ala, Phe or Gly, $X_1$ can also be Leu, $X_2$ can also be Ala, $X_3$ can also be Phe, $X_5$ can also be Gly, $X_6$ can also be Gly, and $X_7$ can also be Arg.

Compounds of the invention, which in a non-limiting preferred embodiment are isolated or substantially pure, also include peptides according to the following Formula VI:

$$\text{LHX}_1\text{X}_2\text{X}_3 \quad \text{(SEQ ID NO: 15)}$$

wherein $X_1$ is Norleucine, Ile, Val, Met, Ala, Phe or Gly; $X_2$ is Val, Leu, Ile or Gly; and $X_3$ is Leu, Val, Ile, Ala, Tyr or Gly; provided that where $X_1$ is Norleucine, Ile, Val, Met, Ala, Phe or Gly, $X_2$ can also be Ala, and $X_3$ can also be Phe;

where $X_2$ is Val, Leu or Ile or Gly, $X_1$ can also be Leu, and $X_3$ can also be Phe; and where $X_3$ is Leu, Val, Ile, Ala, Tyr or Gly, $X_1$ can also be Leu, and $X_2$ can also be Ala.

Compounds of the invention, which in a non-limiting preferred embodiment are isolated or substantially pure, also include peptides according to the following Formula VII:

$$\text{LHX}_1\text{X}_2 \quad \text{(SEQ ID NO: 16)}$$

wherein $X_1$ is Norleucine, Ile, Val, Met, Ala, Phe or Gly; and $X_2$ is Val, Leu, Ile or Gly; provided that where $X_1$ is Norleucine, Ile, Val, Met, Ala, Phe or Gly, $X_2$ can also be Ala; and where $X_2$ is Val, Leu or Ile or Gly, $X_1$ can also be Leu.

Compounds of the invention, which in a non-limiting preferred embodiment are isolated or substantially pure, also include peptides according to the following Formula VIII:

$$\text{LHX}_1 \quad \text{(SEQ ID NO: 17)}$$

wherein $X_1$ is Norleucine, Ile, Val, Met, Ala, Phe or Gly.

Included in the scope of the invention are biologically and/or therapeutically active analogs and conservative variants of these compounds, including truncations thereof, preferably C-terminal truncations. For example, in the above peptides shown as SEQ.ID.NO:1-9 and in Formulae I-VIII, any one or more of the Leucines (L) can be substituted with Isoleucine (I), with D-leucine or D-isoleucine, or with tert-leucine, norleucine, L-allo-isoleucine, D-allo-isoleucine, D-tert-leucine and D-norleucine, and/or the histidine can be substituted with any non-naturally occurring amino acid that has or is prepared to have a side chain terminating with an imidazole ring.

In one non-limiting embodiment, one or more of the amino acids of the peptides within the scope of the invention, including SEQ.ID.NOS:1-9 and sequences within Formulae I-VIII, may be in the L- or D-configuration. In other embodiments, one or more of the amino acids of the peptides within the scope of the invention are naturally-occurring non-genetically coded amino acids. In still other embodiments, one or more of the amino acids of the peptides within the scope of the invention are amino acid analogs or synthetic amino acids.

In another non-limiting embodiment, the N-terminal Leucine (or Isoleucine D-leucine, D-isoleucine, tert-leucine, norleucine, L-allo-isoleucine, D-allo-isoleucine, D-tert-leucine or D-norleucine) of the peptides within the scope of the invention, including SEQ.ID.NOS:1-9 and sequences within Formulae I-VIII, may be may be modified to contain a formyl group, a group comprising a formyl group, an ester of a carboxylic acid (preferably an aldehyde ester, e.g., a carboxyethyl group, a carboxymethyl group, etc.), or a group comprising a an ester of a carboxylic acid. Modifications with formyl, carboxyethyl, and carboxymethyl groups are presently preferred.

In another embodiment, one or more the amino acids in compounds within the scope of the invention, including SEQ.ID.NOS:1-9 and sequences within Formulae I-VIII, are substituted for another amino acid from a similar amino acid class or subclass, based primarily upon the chemical and physical properties of the amino acid side chain. For example, one or more hydrophilic or polar amino acids can be substituted for another hydrophilic or polar amino acid. Likewise, one or more hydrophobic or nonpolar amino acids can be substituted for another hydrophobic or nonpolar amino acid. In making such substitutions, polar amino acids can be further subdivided into amino acids having acidic, basic or hydrophilic side chains and nonpolar amino acids can be further subdivided amino acids having aromatic or hydrophobic side chains. Nonpolar amino acids may be further subdivided to include, among others, aliphatic amino acids.

Also within the scope of the invention are compounds of the invention that have been modified to improve their biopharmaceutical properties. In certain embodiments, the compounds of the invention are modified, for example, to provide increased stability, increased resistance to proteolytic inactivation, decreased to nonexistent immunogenicity, increased circulatory lives, including modified serum half-lives and modified therapeutic half-lives, and low toxicity. Methods by which the compounds of the invention can be modified include, for example, by PEGylation, by chemical derivitization, and by fusion or conjugation with peptides or lipids. Modified compounds include modified Type-B natriuretic signal peptide fragment agents, including, for example, modified BNPsp(17-26) (SEQ ID NO:1), and modified analogs, variants (e.g., conservative variants) and truncations thereof. Other embodiments include peptides selected from SEQ.ID.NOS:2 to 9 that have been modified, and peptides according to Formula I, Formula II, Formula III, Formula IV, Formula V, Formula VI, Formula VII and/or Formula VIII that has been modified, and active analogs, variants (e.g., conservative variants) and truncations thereof that have been modified.

This invention envisions prodrug forms of the therapeutic peptides of the invention. A "prodrug" is a modified form of a therapeutic peptide that includes a reversible chemical modification that can reliably removed to convert the prodrug to the parent peptide through either an enzymatic or nonenzymatic catalytic reaction under physiological conditions following delivery to a patient. Such modifications can enhance chemical stability, alter aqueous solubility, extend biological half-life, broaden therapeutic indices, improve pharmacodynamics, and/or improve bioavailability, for example, while preserving the pharmacological properties of the parent therapeutic peptide. Such modifications can also allow the parent peptide to be released after it reaches the biological compartment where it can exert the desired effect. A "prodrug" is a compound that may include one or more specialized non-toxic protective groups used in a transient manner to alter or to eliminate certain limiting properties in the parent peptide, which protective group(s) can be removed by enzymatic or chemical cleavage. Any suitable protective group(s) can be employed to generate a peptide prodrug of the invention. Such specialized modifications include inclusion of one or more amino acid residues at either or both the amino- and/or carboxy-terminus of the parent peptide. Cleavage sites that allow for the efficient in vivo removal of additional N- or C-terminal amino acids or amino acid sequences are preferably included in such prodrug molecules. Modifications other than the addition of one or more N- and/or C-terminal amino acid residues are also envisioned. For example, diketopiperazine and diketomorpholine (DKP and DMP) strategies for prodrug conversion may be used (see, e.g., Application of Peptide-Badsed Prodrug Chemistry in Drug Development, Springer, Ed. De, Arnab (2012)), where prodrugs slowly convert to the parent drug at physiological conditions driven by the compounds' inherent chemical instability, without the need of any enzymatic cleavage. To improve stability, parent peptides of the invention can be protected against exopeptidase-mediated hydrolysis by bioreversibly masking N- and/or C-terminal amino acids.

Examples of prodrugs of the invention are those wherein the parent peptide includes one or more additional amino acid residues appended to the N- and/or C-terminus of the parent peptide. The compounds of the invention also include prodrug forms of the agents of the invention. For example, prodrug forms include those having one to 16 amino acid residues appended to the N-terminus of, for example, the peptide BNPsp(17-26) (SEQ ID NO:1). Examples of such prodrug forms include those that have one or more of the amino acids listed in Table 1 linked to the parent peptide via a suitable bond. Representative prodrug embodiments include residues 1-16, 2-16, 3-16, 4-16, 5-16, 6-16, 7-16, 8-16, 9-16, 10-16, 11-16, 12-16, 13-16, 14-16, and 15-16 linked to the N-terminus of, for example, BNPsp(17-26), or any of the other peptides from SEQ.ID.NOS:2 to 9, and peptides according to Formula I, Formula II, Formula III, Formula IV, Formula V, Formula VI, Formula VII and/or Formula VIII, and active analogs and variants (e.g., conservative variants) of the foregoing. The table below discloses SEQ ID NO: 18.

| BNPsp Amino Acid Residue Position | Amino Acid at Residue Position |
|---|---|
| 1 | M |
| 2 | D (or G or E) |
| 3 | P (or L) |
| 4 | Q (or K or R or C or L) |
| 5 | T (or K or M or A) |
| 6 | A (or V) |
| 7 | P (or L |
| 8 | S (or L or P) |
| 9 | R (or Q) |
| 10 | A (or T or M) |
| 11 | L (or I or V) |
| 12 | L |
| 13 | L (or F) |
| 14 | L |
| 15 | L |
| 16 | F |
| 17 | L |
| 18 | H (or N or Y) |
| 19 | L |
| 20 | A (or S) |
| 21 | F (or P or L) |

| BNPsp Amino Acid Residue Position | Amino Acid at Residue Position |
| --- | --- |
| 22 | L |
| 23 | G |
| 24 | G (or C) |
| 25 | R (or H) |
| 26 | S (or P) |

Further examples of a prodrug according to the invention include those wherein an amino group of parent peptide is acylated, alkylated, phosphorylated, eicosanoylated, alanylated, pentylaminocarbonylated, (5-methyl-2-oxo-1,3-dioxolen-4-yl)methoxycarbonylated, tetrahydrofuranylated, pyrrolidyl methylated, pivaloyloxymethylated or tert-butylated, and the like; a compound wherein a hydroxy group of the parent peptide is acylated, alkylated, phosphorylated, acetylated, palmitoylated, propanoylated, pivaloylated, succinylated, fumarylated, alanylated or dimethylaminomethylcarbonylated, and the like; and a compound wherein a carboxy group of the parent peptide is esterified or amidated (e.g., ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-exo-1,3-dioxolen-4-yl)methyl esterified, cyclohexyloxycarbonylethyl esterified or methylamidated, and the like) and the like.

Other prodrugs forms are also envisioned, including those containing chemical modifications to one or more amino acids residues that are not positioned at the N- or C-terminus of the parent peptide. As those in the art will appreciate, any suitable chemical modification that can be removed under physiological conditions to yield a pharmaceutically active form of a compound of the invention can be utilized.

Other embodiments include peptidiomimetics of compounds of the invention.

A presently preferred Type-B natriuretic signal peptide fragment agent is BNPsp(17-26) (SEQ ID NO:1).

Illustrations of cardioprotective activities of Type-B natriuretic signal peptide fragment agents are provided in the below Examples. Example 1 shows the ability of Type-B natriuretic signal peptide fragment agents to improve cardiac contractility by administration of BNPsp(17-26) (SEQ ID NO:1) before and after 45 minutes of global ischemia in isolated rat heart preparations. In the in vivo sheep experiments of Example 2, it is shown that cardiac contractile function and troponin release, diagnostic markers of myocardial damage, are improved by administration of a Type-B natriuretic signal peptide fragment agent, BNPsp(17-26) (SEQ ID NO:1). Example 3 describes experiments to assess BNPsp fragment peptides of various lengths and their bioactivity as observed in Example 1 and referred to in Example 2.

Synthesis of Type-B natriuretic signal peptide fragment agents, as well as modified Type-B natriuretic signal peptide fragment agents, is carried out using methods known in the art. Compounds of the inventions that are peptides, such as SEQ.ID.NOS:1-9, can be made by solid-state chemical peptide synthesis. Other compounds, such as fusion peptides, can also be made by conventional recombinant techniques using standard procedures described in, for example, Sambrook & Maniaitis. The peptides and other compounds of the invention may be chemically modified. This may enhance their resistance to peptidases and other enzymes, restrict clearance by the kidney, etc. Methods of preparing such modified compounds are known in the art.

The precise sequence of the Type-B natriuretic signal peptide fragment agent used will depend upon its ability to ameliorate on or more of the symtoms or effects of a cardiovascular disorder. Means for determining such effects are provided in Examples 1 and 2. Other means for assessing the utility of a Type-B natriuretic signal peptide fragment agent for treatment or prevention of a cardiovascular disorder include in vitro cell culture experiments using cardiac myocyte and non-myocyte cell lines, as well as in vivo and ex vivo experiments with models of cardiac congenital disease and toxicity.

Suitable Type-B natriuretic signal peptide fragment agents for the preparation of the pharmaceutical compositions of the invention include LHLAFLGGRS (SEQ.ID.NO: 1), LHLAFLGGR (SEQ.ID.NO:2), LHLAFLGG (SEQ.ID.NO:3), LHLAFLG (SEQ.ID.NO:4), LHLAFL (SEQ.ID.NO:5), LHLAF (SEQ.ID.NO:6), LHLA (SEQ.ID.NO:7), LHL (SEQ.ID.NO:8), and LH (SEQ.ID.NO:9). Other suitable Type-B natriuretic signal peptide fragment agents for the preparation of the pharmaceutical compositions of the invention include peptides within Formulae I-VIII. Other suitable Type-B natriuretic signal peptide fragment agents for the preparation of the pharmaceutical compositions are described herein, and include, for example, analogs, variation, truncations and modifications (including fusions) of the foregoing compounds.

Type-B natriuretic signal peptide fragment agent activity can be selected in terms of their sequence and desired activity by any convenient, and conventional, approach including, for example, as described in the Examples below.

Homology and homologues of Type-B natriuretic signal peptide fragment agents, for example, Type-B natriuretic signal peptide fragments, are discussed herein. Such a Type-B natriuretic signal peptide fragment typically has at least about 70% homology, preferably at least about 80%, at least about 90%, at least about 95%, at least about 97% or at least about 99% homology with the relevant sequence.

Homology may be calculated based on any method in the art. For example the UWGCG Package provides the BEST-FIT program which can be used to calculate homology (for example used on its default settings). The PILEUP and BLAST algorithms can be used to calculate homology or line up sequences (typically on their default settings), for example as described in Altschul S. F. (1993) J Mol Evol 36: 290-300; Altschul, S, F et al (1990) Mol Biol 215: 403-10.

Software for performing BLAST analyses is publicly available through the National Center for Biotechnology Information.

The BLAST algorithm parameters W, T and X determine the sensitivity and speed of the alignment. The BLAST program uses as defaults a word length (W), the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to a second sequence is less than about 1, preferably less than about 0.1, more preferably less than about 0.01, and most preferably less than about 0.001.

The homologous sequence typically differs from the relevant sequence by at least about (or by no more than about) 2, 5, 10, 15, 20 more mutations (which may be substitutions, deletions or insertions). These mutations may be measured across any of the regions mentioned above in relation to calculating homology.

Cardiovascular Therapeutic Agents

Compositions and methods of the invention for the prevention and/or treatment of a cardiovascular disorder, e.g., an acute coronary syndrome, heart failure, ischemic heart disease, etc., and related cardiovascular diseases, disorders and conditions involving ischemia and/or oxidative stress, also comprise administration of a Type-B natriuretic signal peptide fragment agent in series or in combination with (e.g., in physical combination, provided as a combined preparation) one or more other cardiovascular treatment agents. Cardiovascular therapeutic agents include nitrates, β-blockers, calcium channel blockers (particularly for stable or unstable angina, but also for heart failure in the case of β-blockers), diuretic agents, vasodilator agents, positive inotropes, ACE inhibitors and aldosterone antagonists, e.g. spironolactone (particularly for heart failure), blood thinning therapeutics (e.g., aspirin, heparins, warfarins) and nitroglycerin (particularly for MI).

Compositions and methods of the invention for the prevention and/or treatment of a cardiovascular disorder, e.g., an acute coronary syndrome, heart failure, ischemic heart disease, etc., and related cardiovascular diseases, disorders and conditions involving ischemia and/or oxidative stress, may also comprise administration of a Type-B natriuretic signal peptide fragment agent in series or in combination with (e.g., in physical combination, provided as a combined preparation) one or more anti-thrombolytic therapies (e.g., streptokinase inhibitors, anti-platelet thereapetuics, such as, for example, clopidogrel).

Compositions and methods of the invention for the prevention and/or treatment of a cardiovascular disorder, e.g., an acute coronary syndrome, heart failure, ischemic heart disease, etc., and related cardiovascular diseases, disorders and conditions involving ischemia and/or oxidative stress, may also comprise administration of a Type-B natriuretic signal peptide fragment agent in series or in combination with (e.g., in physical combination, provided as a combined preparation) a Type-B natriuretic peptide, including for example nesiritide, a recombinant form of Type-B natriuretic peptide.

In certain methods and compositions (including pharmaceutical compositions, formulations, articles of manufacture and kits) of the invention for the prevention and/or treatment of a cardiovascular disorder, e.g., an acute coronary syndrome, heart failure, ischemic heart disease, etc., and related cardiovascular diseases, disorders and conditions involving ischemia and/or oxidative stress, sub-therapeutically effective amounts of a Type-B natriuretic signal peptide fragment agent, and one or more other cardiovascular treatment agents are used or provided for combined administration (separately or jointly as a combined preparation) to provide a combined action that is therapeutically effective.

Thus, it will be understood that compositions and methods of the invention for the treatment of a cardiovascular disorder, e.g., an acute coronary syndrome, heart failure, ischemic heart disease, etc., and related cardiovascular diseases, disorders and conditions involving ischemia and/or oxidative stress, that employ a Type-B natriuretic signal peptide fragment agent and another cardiovascular therapeutic agent are disclosed. A Type-B natriuretic signal peptide fragment agent may be selected, for example, from the group consisting of BNPsp(17-26) (SEQ ID NO:1), BNPsp(17-25) (SEQ ID NO:2), BNPsp(17-24) (SEQ ID NO:3), BNPsp(17-23) (SEQ ID NO:4), BNPsp(17-22) (SEQ ID NO:5), BNPsp(17-21) (SEQ ID NO:6), BNPsp(17-20) (SEQ.ID.NO:7), BNPsp(17-19) (SEQ.ID.NO:8), and BNPsp(17-18) (SEQ.ID.NO:9). In another embodiment, a Type-B natriuretic signal peptide fragment agent may be selected from the group consisting of a sequence according any one of Formula I, Formula II, Formula III, Formula IV, Formula V, Formula VI, Formula VII and Formula VIII. Optionally, a cardiovascular agent is selected, for example, from the group comprising or consisting essentially of nitrates, β-blockers, calcium channel blockers, diuretic agents, vasodilator agents, positive inotropes, ACE inhibitors, aldosterone antagonists, nitroglycerin, blood thinning agents, anti-thrombolytic agents, and Type-B natriuretic peptides.

Treatment of a subject as provided herein with one or more compounds or pharmaceutical compositions as described herein may comprise their acute or sustained administration and, in the case of combinations, their simultaneous, separate, or sequential administration, as further described herein.

The agents of the invention of the may be administered to a subject in need of treatment, such as a subject with any of the diseases, disorders or conditions mentioned herein. The condition of the subject can thus be improved. The agents may be used in the manufacture of a medicament to treat any of the diseases, disorders or condtions mentioned herein. Thus, in accordance with the invention, there are provided formulations by which cardiovascular disorders can be treated.

A therapeutically effective amount of each of the combination partners (e.g., a Type-B natriuretic signal peptide fragment agent and another cardiovascular therapeutic agent) may be administered simultaneously, separately or sequentially and in any order. The agents may be administered separately or as a fixed combination. When not administered as a fixed combination, preferred methods include the sequential administration of a Type-B natriuretic signal peptide fragment agent and another cardiovascular therapeutic agent, either or both of which are provided in amounts or doses that are less that those used when the agent or agents are administered alone, i.e., when they are not administered in combination, either physically or in the course of treatment. Such lesser amounts of agents administered are typically from about one-twentieth to about one-tenth the amount or amounts of the agent when administered alone, and may be about one-eighth the amount, about one-sixth the amount, about one-fifth the amount, about one-fourth the amount, about one-third the amount, and about one-half the amount when administered alone. Preferably, the agents are administered sequentially within at least about one-half hour of each other. The agents may also be administered within about one hour of each other, within about one day to about one week of each other, or as otherwise deemed appropriate.

The agents of the invention of the may be administered to a subject in need of treatment, such as a subject with an acute coronary syndrome or any of the diseases or conditions mentioned herein. The condition of the subject can thus be improved. The compounds may thus be used in the treatment of the subject's body by therapy. They may be used in the manufacture of a medicament to treat any of the conditions mentioned herein. Thus, in accordance with the invention, there are provided formulations by which cardiotherapy and cardioprotection can be specifically evoked.

Dosage Forms and Formulations and Administration

The compounds of the invention may be present in an isolated or substantially or essentially pure form. It will be understood that the product may be mixed with carriers or diluents which will not interfere with the intended purpose of the product and still be regarded as isolated or substantially pure. A product of the invention may also be in a substantially or essentialy purified form, preferably comprising or consisting essentially of about 80%, 85%, or 90%, e.g. at least about 95%, at least about 98% or at least about 99% of the compound or dry mass of the preparation.

Depending on the intended route of administration, the pharmaceutical products, pharmaceutical compositions, combined preparations and medicaments of the invention may, for example, take the form of solutions, suspensions, instillations, sustained release formulations, or powders, and typically contain about 0.1%-95% of active ingredient(s), preferably about 0.2%-70%. Other suitable formulations include injection- and infusion-based formulations. Other useful formulations include sustained release preparations, including, for example, controlled, slow or delayed release preparations.

Aspects of the invention include controlled or other doses, dosage forms, formulations, compositions and/or devices containing one or more Type-B natriuretic signal peptide fragment agents, wherein the Type-B natriuretic signal peptide fragment agents are, for example, one or more Type-B natriuretic signal peptide fragments. The present invention includes, for example, doses and dosage forms for at least oral administration, transdermal delivery, topical application, suppository delivery, transmucosal delivery, injection (including subcutaneous administration, subdermal administration, intramuscular administration, depot administration, and intravenous administration, including delivery via bolus, slow intravenous injection, and intravenous drip), infusion devices (including implantable infusion devices, both active and passive), administration by inhalation or insufflation, buccal administration and sublingual administration. It will be appreciated that any of the dosage forms, compositions, formulations or devices described herein particularly for intravenous administration may be utilized, where applicable or desirable, in a dosage form, composition, formulation or device for administration by any of the other routes herein contemplated or commonly employed. For example, a dose or doses could be given parenterally using a dosage form suitable for parenteral administration which may incorporate features or compositions described in respect of dosage forms suitable for oral administration, or be delivered in an sustained dosage form, such as a modified release, extended release, delayed release, slow release or repeat action dosage form.

Preferably the Type-B natriuretic signal peptide fragment agents of the invention are combined with a pharmaceutically acceptable carrier or diluent to produce a pharmaceutical composition. Suitable carriers and diluents include isotonic saline solutions, for example phosphate-buffered saline. Suitable diluents and excipients also include, for example, water, saline, dextrose, glycerol, or the like, and combinations thereof. In addition, if desired substances such as wetting or emulsifying agents, stabilizing or pH buffering agents may also be present.

The term "pharmaceutically acceptable carrier" refers to any useful carriers, excipients, or stabilizers which are nontoxic to the cell or mammal being exposed thereto at the dosages and concentrations employed, and include pharmaceutical carriers that do not induce the production of antibodies harmful to the individual receiving the composition. Suitable carriers can be large, slowly metabolized macromolecules such as proteins, polysaccharides, polylactic acids, polyglycolic acids, polymeric amino acids, and amino acid copolymers. Often the physiologically acceptable carrier is an aqueous pH buffered solution. Other examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

Pharmaceutically acceptable salts can also be present, e.g., mineral acid salts such as hydrochlorides, hydrobromides, phosphates, sulfates, and the like; and the salts of organic acids such as acetates, propionates, malonates, benzoates, and the like.

Suitable carrier materials include any carrier or vehicle commonly used as a base for creams, lotions, gels, emulsions, or paints for topical administration. Examples include emulsifying agents, inert carriers including hydrocarbon bases, emulsifying bases, non-toxic solvents or water-soluble bases. Particularly suitable examples include PLURONICS®, HPMC, CMC and other cellulose-based ingredients, lanolin, hard paraffin, liquid paraffin, soft yellow paraffin or soft white paraffin, white beeswax, yellow beeswax, cetostearyl alcohol, cetyl alcohol, dimethicones, emulsifying waxes, isopropyl myristate, microcrystalline wax, oleyl alcohol and stearyl alcohol.

An auxiliary agent such as casein, gelatin, albumin, glue, sodium alginate, carboxymethylcellulose, methylcellulose, hydroxyethylcellulose or polyvinyl alcohol may also be included in the formulation of the invention.

The dosage forms, formulations, devices and/or compositions of the invention may be formulated to optimize bioavailability and to maintain plasma concentrations within the therapeutic range, including for extended periods. Sustained delivery preparations, e.g., controlled delivery preparations, also optimize the drug concentration at the site of action and minimize periods of under and over medication, for example.

The dosage forms, devices and/or compositions useful in the invention may be provided for periodic administration, including once daily administration, for low dose controlled and/or low dose long-lasting in vivo release of a Type-B natriuretic signal peptide fragment agent.

Examples of dosage forms suitable for oral administration include, but are not limited to tablets, capsules, lozenges, or like forms, or any liquid forms such as syrups, aqueous solutions, emulsions and the like, capable of providing a therapeutically effective amount of a Type-B natriuretic signal peptide fragment agent.

Examples of dosage forms suitable for transdermal administration include, but are not limited to, transdermal patches, transdermal bandages, and the like. Examples of dosage forms suitable for topical administration of the compounds and formulations useful in the invention are any lotion, stick, spray, ointment, paste, cream, gel, etc., whether applied directly to the skin or via an intermed.

Examples of dosage forms suitable for suppository administration of the compounds and formulations useful in the invention include any solid dosage form inserted into a bodily orifice particularly those inserted rectally, vaginally and urethrally.

Examples of dosage forms suitable for transmucosal delivery of the compounds and formulations useful in the invention include depositories solutions for enemas, pessaries, tampons, creams, gels, pastes, foams, nebulised solutions, powders and similar formulations containing in addition to the active ingredients such carriers as are known in the art to be appropriate.

Examples of dosage of forms suitable for injection of the compounds and formulations useful in the invention include delivery via bolus such as single or multiple administrations by intravenous injection, subcutaneous, subdermal, and intramuscular administration or oral administration.

Examples of dosage forms suitable for depot administration of the compounds and formulations useful in the invention include pellets or small cylinders of active agent or solid forms wherein the active agent is entrapped in a matrix of biodegradable polymers, microemulsions, liposomes or is microencapsulated.

Examples of infusion devices for compounds and formulations useful in the invention include infusion pumps containing one or more Type-B natriuretic signal peptide fragment agents and/or pre-complexed Type-B natriuretic signal peptide fragment agents, at a desired amount for a desired number of doses or steady state administration, and include implantable drug pumps.

Examples of implantable infusion devices for compounds and formulations useful in the invention include any solid form in which the active agent is encapsulated within or dispersed throughout a biodegradable polymer or synthetic, polymer such as silicone, silicone rubber, silastic or similar polymer.

Examples of dosage forms suitable for inhalation or insufflation of compounds and formulations useful in the invention include compositions comprising solutions and/or suspensions in pharmaceutically acceptable, aqueous, or organic solvents, or mixture thereof and/or powders.

Examples of dosage forms suitable for buccal administration of the compounds and formulations useful in the invention include lozenges, tablets and the like, compositions comprising solutions and/or suspensions in pharmaceutically acceptable, aqueous, or organic solvents, or mixtures thereof and/or powders.

Examples of dosage forms suitable for sublingual administration of the compounds and formulations useful in the invention include lozenges, tablets and the like, compositions comprising solutions and/or suspensions in pharmaceutically acceptable, aqueous, or organic solvents, or mixtures thereof and/or powders.

Examples of controlled drug formulations for delivery of the compounds and formulations useful in the invention are found in, for example, Sweetman, S. C. (Ed.). Martindale. The Complete Drug Reference, 33rd Edition, Pharmaceutical Press, Chicago, 2002, 2483 pp.; Aulton, M. E. (Ed.) Pharmaceutics. The Science of Dosage Form Design. Churchill Livingstone, Edinburgh, 2000, 734 pp.; and, Ansel, H. C., Allen, L. V. and Popovich, N. G. Pharmaceutical Dosage Forms and Drug Delivery Systems, 7th Ed., Lippincott 1999, 676 pp. Excipients employed in the manufacture of drug delivery systems are described in various publications known to those skilled in the art including, for example, Kibbe, E. H. Handbook of Pharmaceutical Excipients, 3rd Ed., American Pharmaceutical Association, Washington, 2000, 665 pp. The USP also provides examples of modified-release oral dosage forms, including those formulated as tablets or capsules. See, for example, The United States Pharmacopeia 23/National Formulary 18, The United States Pharmacopeial Convention, Inc., Rockville Md., 1995 (hereinafter "the USP"), which also describes specific tests to determine the drug release capabilities of extended-release and delayed-release tablets and capsules. Further guidance concerning the analysis of extended release dosage forms has been provided by the FDA. See Guidance for Industry. Extended release oral dosage forms: development, evaluation, and application of in vitro/in vivo correlations. Rockville, Md.: Center for Drug Evaluation and Research, Food and Drug Administration (1997).

Further examples of dosage forms useful in the methods of the invention include, but are not limited to, modified-release (MR) dosage forms including delayed-release (DR) forms; prolonged-action (PA) forms; controlled-release (CR) forms; extended-release (ER) forms; timed-release (TR) forms; and long-acting (LA) forms. For the most part, these terms are used to describe orally administered dosage forms, however these terms may be applicable to any of the dosage forms, formulations, compositions and/or devices described herein. These formulations effect delayed total drug release for some time after drug administration, and/or drug release in small aliquots intermittently after administration, and/or drug release slowly at a controlled rate governed by the delivery system, and/or drug release at a constant rate that does not vary, and/or drug release for a significantly longer period than usual formulations.

Modified-release dosage forms of the invention include dosage forms having drug release features based on time, course, and/or location which are designed to accomplish therapeutic or convenience objectives not offered by conventional or immediate-release forms. See, for example, Bogner, R. H. *U.S. Pharmacist* 22 (Suppl.):3-12 (1997); Scale-up of oral extended-release drug delivery systems: part I, an overview, *Pharmaceutical Manufacturing* 2:23-27 (1985). Extended-release dosage forms of the invention include, for example, as defined by The United States Food and Drug Administration (FDA), a dosage form that allows a reduction in dosing frequency to that presented by a conventional dosage form, e.g., a solution or an immediate-release dosage form. See, for example, Bogner, R. H. (1997) supra. Repeat action dosage forms of the invention include, for example, forms that contain two single doses of medication, one for immediate release and the second for delayed release. Bi-layered tablets, for example, may be prepared with one layer of drug for immediate release with the second layer designed to release drug later as either a second dose or in an extended-release manner. Targeted-release dosage forms of the invention include, for example, formulations that facilitate drug release and which are directed towards isolating or concentrating a drug in a body region, tissue, or site for absorption or for drug action.

Also useful in the invention are coated beads, granules or microspheres containing one or more Type-B natriuretic signal peptide fragment agents and/or pre-complexed Type-B natriuretic signal peptide fragment agents, which may be used to achieve modified release of one or more Type-B natriuretic signal peptide fragment agents and/or pre-complexed Type-B natriuretic signal peptide fragment agents by incorporation of the drug into coated beads, granules, or microspheres. In such systems, the Type-B natriuretic signal peptide fragment agent and/or pre-complexed Type-B natriuretic signal peptide fragment agent is distributed onto beads, pellets, granules or other particulate systems. See Ansel, H. C., Allen, L. V. and Popovich, N. G., Pharmaceutical Dosage Forms and Drug Delivery Systems, 7th Ed., Lippincott 1999, p. 232.

Methods for manufacture of microspheres suitable for drug delivery have been described. See, for example, Arshady, R. Polymer Eng Sci 30:1746-1758 (1989); see also, Arshady, R., Polymer Eng Sci 30:905-914 (1990); see also: Arshady R., Polymer Eng Sci 30:915-924 (1990). Various coating systems are commercially available. E.g., AQUACOAT® [FMC Corporation, Philadelphia] and SURERELEASE™ [Colorcon]; AQUACOAT® aqueous polymeric dispersion. Philadelphia: FMC Corporation, 1991; Surerelease SURERELEASE™ aqueous controlled release coating system. West Point, Pa.: Colorcon, 1990; Butler, J., et al., Pharm Tech 22:122-138 (1998); Yazici, E., et al., Pharmaceut Dev Technol 1:175-183 (1996).

Variation in the thickness of the coats and in the type of coating materials used affects the rate at which the body fluids are capable of penetrating the coating to dissolve the Type-B natriuretic signal peptide fragment agent. Generally, the thicker the coat, the more resistant to penetration and the more delayed will be Type-B natriuretic signal peptide fragment agent release and dissolution. See Madan, P. L. *U.S. Pharmacist* 15:39-50 (1990). This provides the different desired sustained or extended release rates and the targeting of the coated beads to the desired segments of the gastrointestinal tract. Examples of film-forming polymers which can be used in water-insoluble release-slowing intermediate layer(s) (to be applied to a pellet, spheroid or tablet core) include ethylcellulose, polyvinyl acetate, Eudragit® RS, Eudragit® RL, etc. (Each of Eudragit® RS and Eudragit® RL is an ammonio methacrylate copolymer. The release rate can be controlled not only by incorporating therein suitable water-soluble pore formers, such as lactose, mannitol, sorbitol, etc., but also by the thickness of the coating layer applied. Multi-tablets may be formulated which include small spheroid-shaped compressed mini-tablets that may have a diameter of between 3 to 4 mm and can be placed in a gelatin capsule shell to provide the desired pattern of Type-B natriuretic signal peptide fragment agent release. Each capsule may contain 8-10 minitablets, some uncoated for immediate release and others coated for extended release of the Type-B natriuretic signal peptide fragment agent.

A number of methods may be employed to generate modified-release dosage forms of one or more Type-B natriuretic signal peptide fragment agents suitable for oral administration to humans and other mammals. Two basic mechanisms available to achieve modified release drug delivery include altered dissolution or diffusion of drugs and excipients. Within this context, for example, four processes may be employed, either simultaneously or consecutively. These are as follows: (i) hydration of the device (e.g., swelling of the matrix); (ii) diffusion of water into the device; (iii) controlled or delayed dissolution of the drug; and (iv) controlled or delayed diffusion of dissolved or solubilized drug out of the device.

In order to formulate a range of dosage values, cell culture assays and animal studies can be used. The dosage of such compounds preferably lies within the dose that is therapeutically effective for at least 50% of the population, and that exhibits little or no toxicity at this level.

The effective dosage of each of the Type-B natriuretic signal peptide fragment agents employed in the methods and compositions of the invention may vary depending on a number of factors including the particular Type-B natriuretic signal peptide fragment agent or agents employed, the cardiovascular therapeutic combinational partner if present, the mode of administration, the frequency of administration, the condition being treated, the severity of the condition being treated, the route of administration, the needs of a patient sub-population to be treated or the needs of the individual patient which different needs can be due to age, sex, body weight, relevant medical condition specific to the patient.

A suitable dose may be from about 0.001 to about 1 or to about 10 mg/kg body weight such as about 0.01 to about 0.5 mg/kg body weight. A suitable dose may however be from about 0.001 to about 0.1 mg/kg body weight such as about 0.01 to about 0.05 mg/kg body weight. Doses from about 1 to 100, 100-200, 200-300, 300-400, and 400-500 miligrams are appropriate, as are doses of about 500-750 micrograms and about 750-1000 micrograms. Other useful doses include from about 300 to about 1000 picomoles per dose, and about 0.05 to about 0.2 nanomoles per dose. Still other doses are within the following claims.

For example, in certain embodiments, the Type-B natriuretic signal peptide fragment agent composition may be administered at about 0.01 nanomolar (mM) or 0.05 nM to about 200 nM final concentration. Preferably, the Type-B natriuretic signal peptide fragment agent composition is administered at about 0.1 nM to about 150 nM final concentration, more preferably, the Type-B natriuretic signal peptide fragment agent composition is applied at about 1 nM to about 100 nM final concentration, and more preferably, the Type-B natriuretic signal peptide fragment agent composition is administered at about 10-20 nM to about 100-150 nM final concentration. Additionally, Type-B natriuretic signal peptide fragment agent dose amounts include, for example, about 0.1-1, 1-2, 2-3, 3-4, or 4-5 milligrams (mg), from about 5 to about 10 mg, from about 10 to about 15 mg, from about 15 to about 20 mg, from about 20 to about 30 mg, from about 30 to about 40 mg, from about 40 to about 50 mg, from about 50 to about 75 mg, from about 75 to about 100 mg, from about 100 mg to about 250 mg, and from 250 mg to about 500 mg. Dose amounts from 500 to about 1000 milligrams or more or also provided, as noted above. Other doses include doses ranging from at least about 100 nanograms, including, for example at least about 200 nanograms, 600 nanograms, 2000 nanograms, 6000 nanograms and at least about 10,000 nanograms or more. Dose concentrations include concentrations of at least about 0.1 moles per liter, including, for example, at least about 0.3, 1.0, 3.0 and 10.0 nMoles/L. Dose concentrations also include concentrations of 0.1 nMoles/L, 0.3 nMoles/L, 1.0 nMoles/L, 3.0 nMoles/L and 10.0 nMoles/L. These dose concentrations are equivalent to 0.1, 0.3, 1, 3, 11 µg/L and administrable weight doses of 0.4, 1.0, 4.0, 10 and 39 micrograms/kg (µg/kg). Also within the invention are other doses ranging from 0.1 to 5.0 µg/kg and 0.1 to 10.0 µg/kg. Additionally, doses of about 0.4, 1.0, 4.0, 10 and 39 µg/kg are within the invention. Doses of at least about 0.4, 1.0, 4.0, 10 and 39 µg/kg are also within the invention.

Still other dosage levels between about 1 nanogram (ng)/kg and about 1 mg/kg body weight per day of each of the agents described herein. In certain embodiments, the dosage of each of the subject compounds will generally be in the range of about 1 ng to about 1 microgram per kg body weight, about 1 ng to about 0.1 microgram per kg body weight, about 1 ng to about 10 ng per kg body weight, about 10 ng to about 0.1 microgram per kg body weight, about 0.1 microgram to about 1 microgram per kg body weight, about 20 ng to about 100 ng per kg body weight, about 0.001 mg to about 0.01 mg per kg body weight, about 0.01 mg to about 0.1 mg per kg body weight, or about 0.1 mg to about 1 mg per kg body weight. In certain embodiments, the dosage of each of the subject compounds will generally be in the range of about 0.001 mg to about 0.01 mg/kg body weight, about 0.01 mg to about 0.1 mg/kg body weight, about 0.1 mg to about 1 mg/kg body weight. If more than one Type-B natriuretic signal peptide fragment agent is used, the dosage of each Type-B natriuretic signal peptide fragment agent need not be in the same range as the other.

Conveniently, if infused, the Type-B natriuretic signal peptide fragment agent is administered for at least about 0.5 to 1 hour, at least about 1-2 hours, at least about 2-4 hours, at least about 4-6 hours, at least about 6-8 hours, at least about 8-10 hours, at least about 12 hours, or at least about 24 hours.

As noted herein, the doses of a Type-B natriuretic signal peptide fragment, peptide or peptidomimetic, for example, administered in combination, or other cardiovascular therapeutic agents administered in combination with either or both, can be adjusted down from the doses administered when given alone.

The combined use of several agents may reduce the required dosage for any individual agent because the onset and duration of effect of the different agents may be complementary. In a preferred embodiment, the combined use of two or more Type-B natriuretic signal peptide fragment and/or cardiovascular therapeutic agents has an additive, synergistic or super-additive effect.

In some cases, the combination of a Type-B natriuretic signal peptide fragment agent and a cardiovascular therapeutic agent, or other agents administered in combination with either or both, have an additive effect. In other cases, the combination can have greater-than-additive effect. Such an effect is referred to herein as a "supra-additive" effect, and may be due to synergistic or potentiated interaction.

In another preferred embodiment, the combined use of a Type-B natriuretic signal peptide fragment agent and another cardiovascular therapeutic agent, reduces the frequency in which said agent is administered compared to the frequency when said agent is administered alone. Thus, these combinations allow the use of lower and/or fewer doses of each agent than previously required to achieve desired therapeutic goals.

Doses may be administered in single or divided applications. The doses may be administered once, or application may be repeated. Typically, administration can be by infusion in addition to or instead of multiple single administrations.

One or more Type-B natriuretic signal peptide fragment agents and another cardiovascular therapeutic agent, if desired, may be administered by the same or different routes. The various agents of the invention can be administered separately at different times during the course of therapy, or concurrently in divided or single combination forms.

In one aspect of the invention a Type-B natriuretic signal peptide fragment agent is administered in one composition and another cardiovascular therapeutic agent is administered in a second composition. In one embodiment the first composition comprising a Type-B natriuretic signal peptide fragment peptide agent is administered before the second composition comprising another cardiovascular therapeutic agent. In one embodiment the first composition comprising a Type-B natriuretic signal peptide fragment peptide agent is administered after the second composition comprising another cardiovascular therapeutic agent. In one preferred embodiment the first composition comprising a Type-B natriuretic signal peptide fragment peptide agent is administered before and after the second composition comprising another cardiovascular therapeutic agent. In one embodiment the second composition comprising another cardiovascular therapeutic agent is administered before and after the first composition comprising a Type-B natriuretic signal peptide fragment peptides agent. In one embodiment the first composition comprising a Type-B natriuretic signal peptide fragment peptide agent is administered about the same time as the second composition comprising another cardiovascular therapeutic agent.

The delivery of a formulation comprising a Type-B natriuretic signal peptide fragment agent, alone or together with another cardiovascular therapeutic agent, over a period of time, in some instances for about 1-2 hours, about 2-4 hours, about 4-6 hours, about 6-8, or about 24 hours or longer, may also be accomplished using slow release or depot formulations, for example, as well as transdermal formulations and devices.

Strategies to improve the oral bioavailability of proteins have ranged from changing their physicochemical properties by modification of their lipophilicity and enzyme susceptibility, to adding novel functionality using transport-carrier molecules that are recognized by endogenous transport-carrier systems in the gastrointestinal tract and/or to their inclusion in specially adapted drug carrier systems. Marketed polymeric-based systems have attracted considerable attention in the controlled release in targeting particular organs/tissues, and in their ability to deliver proteins and peptides. They can effectively deliver the proteins to a target site and thus increase the therapeutic benefit, while minimizing side effects. Protein association with polymer-based carriers, such as polymeric microparticles, nanoparticles, hydrogels or patches is a useful approach to improve oral protein bioavailability. Polymer-based carriers can protect proteins from the gastrointestinal environment and allow the modulation of physicochemical and protein release properties and consequently the biological behavior. Also, from the perspective of improving oral absorption, the major effect of carriers is to increase epithelial membrane permeability, thereby leading to higher bioavailability.

Dosage forms of the compounds and formulations of the invention, extended Type-B natriuretic signal peptide fragment agent action may be achieved by affecting the rate at which the Type-B natriuretic signal peptide fragment agent is released from the dosage form and/or by slowing the transit time of the dosage form through the gastrointestinal tract (see Bogner, R. H., *US Pharmacist* 22 (Suppl.):3-12 (1997)). The rate of drug release from solid dosage forms may be modified by the technologies described below which, in general, are based on the following: 1) modifying drug dissolution by controlling access of biologic fluids to the drug through the use of barrier coatings; 2) controlling drug diffusion rates from dosage forms; and 3) chemically reacting or interacting between the drug substance or its pharmaceutical barrier and site-specific biological fluids. Systems by which these objectives are achieved are also provided herein. In one approach, employing digestion as the release mechanism, the Type-B natriuretic signal peptide fragment agent is either coated or entrapped in a substance that is slowly digested or dispersed into the intestinal tract. The rate of availability of the Type-B natriuretic signal peptide fragment agent is a function of the rate of digestion of the dispersible material. Therefore, the release rate, and thus the effectiveness of the Type-B natriuretic signal peptide fragment agent varies from subject to subject depending upon the ability of the subject to digest the material.

A further form of slow release dosage form of the compounds and formulations of the invention is any suitable osmotic system where semi-permeable membranes of for example cellulose acetate, cellulose acetate butyrate, cellulose acetate propionate, is used to control the release of Type-B natriuretic signal peptide fragment agent. These can be coated with aqueous dispersions of enteric lacquers without changing release rate. An example of such an osmotic system is an osmotic pump device, such as the OROS™ device developed by Alza Inc. (U.S.A.).

Other devices useful in the methods of the invention utilize monolithic matrices including, for example, slowly eroding or hydrophilic polymer matrices, in which one or more Type-B natriuretic signal peptide fragment agents are compressed or embedded.

Monolithic matrix devices comprising compounds and formulations useful in the invention include those formed using, for example, Type-B natriuretic signal peptide fragment agents dispersed in a soluble matrix, which become increasingly available as the matrix dissolves or swells; examples include hydrophilic colloid matrices, such as hydroxypropylcellulose (BP) or hydroxypropyl cellulose (USP); hydroxypropyl methylcellulose (HPMC; BP, USP); methylcellulose (MC; BP, USP); calcium carboxymethylcellulose (Calcium CMC; BP, USP); acrylic acid polymer or carboxy polymethylene (Carbopol) or Carbomer (BP, USP); or linear glycuronan polymers such as alginic acid (BP, USP), for example those formulated into microparticles from alginic acid (alginate)-gelatin hydrocolloid coacervate systems, or those in which liposomes have been encapsulated by coatings of alginic acid with poly-L-lysine membranes. Type-B natriuretic signal peptide fragment agent release occurs as the polymer swells, forming a matrix layer that controls the diffusion of aqueous fluid into the core and thus the rate of diffusion of Type-B natriuretic signal peptide fragment agent from the system.

In such systems, the rate of Type-B natriuretic signal peptide fragment agent release depends upon the tortuous nature of the channels within the gel, and the viscosity of the entrapped fluid, such that different release kinetics can be achieved, for example, zero-order, or first-order combined with pulsatile release. Where such gels are not cross-linked, there is a weaker, non-permanent association between the polymer chains, which relies on secondary bonding. With such devices, high loading of the Type-B natriuretic signal peptide fragment agent is achievable, and effective blending is frequent. Devices may contain 20-80% of Type-B natriuretic signal peptide fragment agent (w/w), along with gel modifiers that can enhance Type-B natriuretic signal peptide fragment agent diffusion; examples of such modifiers include sugars that can enhance the rate of hydration, ions that can influence the content of cross-links, and pH buffers that affect the level of polymer ionization. Hydrophilic matrix devices may also contain one or more pH buffers, surfactants, counter-ions, lubricants such as magnesium stearate (BP, USP) and a glidant such as colloidal silicon dioxide (USP; colloidal anhydrous silica, BP) in addition to Type-B natriuretic signal peptide fragment agent and hydrophilic matrix.

Monolithic matrix devices comprising compounds and formulations useful in the invention also include those formed using, for example, Type-B natriuretic signal peptide fragment agent particles are dissolved in an insoluble matrix, from which Type-B natriuretic signal peptide fragment agent becomes available as solvent enters the matrix, often through channels, and dissolves the Type-B natriuretic signal peptide fragment agent particles. Examples include systems formed with a lipid matrix, or insoluble polymer matrix, including preparations formed from Carnauba wax (BP; USP); medium-chain triglyceride such as fractionated coconut oil (BP) or triglycerida saturata media (PhEur); or cellulose ethyl ether or ethylcellulose (BP, USP). Lipid matrices are simple and easy to manufacture, and incorporate the following blend of powdered components: lipids (20-40% hydrophobic solids w/w) which remain intact during the release process; Type-B natriuretic signal peptide fragment agent, e.g., channeling agent, such as sodium chloride or sugars, which leaches from the formulation, forming aqueous micro-channels (capillaries) through which solvent enters, and through which Type-B natriuretic signal peptide fragment agent is released. In this system, the Type-B natriuretic signal peptide fragment agent is embedded in an inert insoluble polymer and is released by leaching of aqueous fluid, which diffuses into the core of the device through capillaries formed between particles, and from which the Type-B natriuretic signal peptide fragment agent diffuses out of the device. The rate of release is controlled by the degree of compression, particle size, and the nature and relative content (w/w) of excipients. An example of such a device is that of Ferrous Gradumet (Martindale 33rd Ed., 1360.3). A further example of a suitable insoluble matrix is an inert plastic matrix. By this method, Type-B natriuretic signal peptide fragment agents are granulated with an inert plastic material such as polyethylene, polyvinyl acetate, or polymethacrylate, and the granulated mixture is then compressed into tablets. Once ingested, the Type-B natriuretic signal peptide fragment agent is slowly released from the inert plastic matrix by diffusion. See, for example, Bodmeier, R. & Paeratakul, O., *J Pharm Sci* 79:32-26 (1990); Laghoueg, N., et al., *Int J Pharm* 50:133-139 (1989); Buckton, G., et al., *Int J Pharm* 74:153-158 (1991). The compression of the tablet creates the matrix or plastic form that retains its shape during the leaching of the Type-B natriuretic signal peptide fragment agent and through its passage through the gastrointestinal tract. An immediate-release portion of Type-B natriuretic signal peptide fragment agent may be compressed onto the surface of the tablet. The inert tablet matrix, expended of Type-B natriuretic signal peptide fragment agent, is excreted with the feces. An example of a successful dosage form of this type is Gradumet (Abbott; see, for example, Ferro-Gradumet, Martindale 33rd Ed., p. 1860.4).

Further examples of monolithic matrix devices useful in the methods of the invention include compositions and formulations of the invention incorporated in pendent attachments to a polymer matrix. See, for example, Scholsky, K. M. and Fitch, R. M., *J Controlled Release* 3:87-108 (1986). In these devices, Type-B natriuretic signal peptide fragment agents may be attached by means of an ester linkage to poly(acrylate) ester latex particles prepared by aqueous emulsion polymerization. Still further examples of monolithic matrix devices of the invention incorporate dosage forms in which the Type-B natriuretic signal peptide fragment agent is bound to a biocompatible polymer by a labile chemical bond, e.g., polyanhydrides prepared from a substituted anhydride (itself prepared by reacting an acid chloride with the drug: methacryloyl chloride and the sodium salt of methoxy benzoic acid) have been used to form a matrix with a second polymer (Eudragit RL) which releases drug on hydrolysis in gastric fluid. See Chafi, N., et al., *Int J Pharm* 67:265-274 (1992).

Modified release forms of one or more Type-B natriuretic signal peptide fragment agents may also be prepared by microencapsulation. Microencapsulation is a process by which solids, liquids, or even gasses may be encapsulated into microscopic size particles through the formation of thin coatings of "wall" material around the substance being encapsulated such as disclosed in U.S. Pat. Nos. 3,488,418; 3,391,416 and 3,155,590. Gelatin (BP, USP) is commonly employed as a wall-forming material in microencapsulated preparations, but synthetic polymers such as polyvinyl alcohol (USP), ethylcellulose (BP, USP), polyvinyl chloride, and other materials may also be used. See, for example, Zentner, G. M., et al., *J Controlled Release* 2:217-229 (1985); Fites, A. L., et al., *J Pharm Sci* 59:610-613 (1970); Samuelov, Y., et al., *J Pharm Sci* 68:325-329 (1979). Different rates of Type-B natriuretic signal peptide fragment agent release may be obtained by changing the core-to-wall ratio, the polymer used for the coating, or the method of microencapsulation. See, for example: Yazici, E., Oner, et al., *Pharmaceut Dev Technol;* 1:175-183 (1996).

Other useful approaches include those in which the Type-B natriuretic signal peptide fragment agent is incorporated into polymeric colloidal particles or microencapsulates (microparticles, microspheres or nanoparticles) in the form or reservoir and matrix devices. See: Douglas, S. J., et al., *C.R.C. Crit. Rev Therap Drug Carrier Syst* 3:233-261 (1987); Oppenheim, R. C., *Int J Pharm* 8:217-234 (1981); Higuchi, T., *J Pharm Sci* 52:1145-1149 (1963).

Formulations of drugs suitable for transdermal delivery are known to those skilled in the art, and are described in references such as Ansel et al., (supra). Methods known to enhance the delivery of drugs by the percutaneous route include chemical skin penetration enhancers, which increase skin permeability by reversibly damaging or otherwise altering the physicochemical nature of the stratum corneum to decrease its resistance to drug diffusion. See Shah, V., Peck, C. C., and Williams, R. L., Skin penetration enhancement: clinical pharmacological and regulatory considerations, In: Walters, K. A. and Hadgraft, J. (Eds.) Pharmaceutical skin penetration enhancement. New York: Dekker, (1993). Skin penetration enhancers suitable for formulation with Type-B natriuretic signal peptide fragment agents in transdermal drug delivery systems may be chosen from the following list: acetone, laurocapram, dimethylacetamide, dimethylformamide, dimethylsulphoxide, ethanol, oleic acid, polyethylene glycol, propylene glycol and sodium lauryl sulphate. Further skin penetration enhancers may be found in publications known to those skilled in the art. See, for example, Osborne, D. W., & Henke, J. J., *Pharm Tech* 21:50-66 (1997); Rolf, D., "*Pharm Tech* 12:130-139 (1988). In addition to chemical means, there are physical methods that enhance transdermal drug delivery and penetration of the compounds and formulations of the invention. These include iontophoresis and sonophoresis. Formulations suitable for administration by iontophoresis or sonophoresis may be in the form of gels, creams, or lotions.

Transdermal delivery, methods or formulations of the invention, may utilize, among others, monolithic delivery systems, drug-impregnated adhesive delivery systems (e.g., the LATITUDE® drug-in-adhesive system from 3M), active transport devices and membrane-controlled systems. Transdermal delivery dosage forms of the invention include those which substitute the Type-B natriuretic signal peptide fragment agent, for the diclofenic or other pharmaceutically acceptable salt thereof referred to in the transdermal delivery systems disclosed in, by way of example, U.S. Pat. Nos. 6,193,996, and 6,262,121.

Other dosage forms include variants of the oral dosage forms adapted for suppository or other parenteral use. When rectally administered in the form of suppositories, for example, these compositions may be prepared by mixing one or more compounds and formulations of the invention with a suitable non-irritating excipient, such as cocoa butter, synthetic glyceride esters or polyethylene glycols, which are solid at ordinary temperatures, but liquify and/or dissolve in the rectal cavity to release the Type-B natriuretic signal peptide fragment agent. Suppositories are generally solid dosage forms intended for insertion into body orifices including rectal, vaginal and occasionally urethrally and can be long acting or slow release. Suppositories include a base that can include, but is not limited to, materials such as alginic acid, which will prolong the release of the pharmaceutically acceptable active ingredient over several hours (5-7).

Transmucosal administration of the compounds and formulations useful in the invention may utilize any mucosal membrane but commonly utilizes the nasal, buccal, vaginal and rectal tissues. Formulations suitable for nasal administration of the compounds and formulations of the invention may be administered in a liquid form, for example, nasal spray, nasal drops, or by aerosol administration by nebulizer, including aqueous or oily solutions of the Type-B signal peptide fragment agent. Formulations for nasal administration, wherein the carrier is a solid, include a coarse powder having a particle size, for example, of less than about 100 microns, preferably less, most preferably one or two times per day than about 50 microns, which is administered in the manner in which snuff is taken, i.e., by rapid inhalation through the nasal passage from a container of the powder held close up to the nose. Compositions in solution may be nebulized by the use of inert gases and such nebulized solutions may be breathed directly from the nebulizing device or the nebulizing device may be attached to a facemask, tent or intermittent Type-B natriuretic signal peptide fragment agents may be administered orally or nasally from devices that deliver the formulation in an appropriate manner. Formulations may be prepared as aqueous solutions for example in saline, solutions employing benzyl alcohol or other suitable preservatives, absorption promoters to enhance bio-availability, fluorocarbons, and/or other solubilising or dispersing agents known in the art.

Compositions may be prepared according to conventional methods by dissolving or suspending an amount of a Type-B natriuretic signal peptide fragment agent(s) (s) ingredient in a diluent. The amount of Type-B natriuretic signal peptide fragment agent is from between 0.1 mg to 1000 mg per ml of diluent. In some embodiments, dosage forms of 100 mg and 200 mg of a Type-B natriuretic signal peptide fragment agent are provided. By way of example only, the amount of Type-B natriuretic signal peptide fragment agent may range from about 1 mg to about 750 mg or more (for example, about 1 mg, about 10 mg, about 25 mg, about 50 mg, about 100 mg, about 150 mg, about 200 mg, about 250 mg, about 400 mg, about 500 mg, about 600 mg, about 750 mg, about 800 mg, about 1000 mg, and about 1200 mg). Other doses include doses ranging from at least about 100 nanograms, including, for example at least about 200 nanograms, 600 nanograms, 2000 nanograms, 6000 nanograms and at least about 10,000 nanograms or more. Dose concentrations include concentrations of at least about 0.1 moles per liter, including, for example, at least about 0.3, 1.0, 3.0 and 10.0 nMoles/L. Dose concentrations also include concentrations of 0.1 nMoles/L, 0.3 nMoles/L, 1.0 nMoles/L, 3.0 nMoles/L and 10.0 nMoles/L. These dose concentrations are equivalent to 0.1, 0.3, 1, 3, 11 µg/L and administrable weight doses of 0.4, 1.0, 4.0, 10 and 39 micrograms/kg (µg/kg). Also within the invention are other doses ranging from 0.1 to 5.0 µg/kg and 0.1 to 10.0 µg/kg. Additionally, doses of about 0.4, 1.0, 4.0, 10 and 39 µg/kg are within the invention. Doses of at least about 0.4, 1.0, 4.0, 10 and 39 µg/kg are also within the invention. Other amounts within these ranges may also be used and are specifically contemplated though each number in between is not expressly set out.

Type-B natriuretic signal peptide fragment agents can be provided and administered in forms suitable for once-a-day dosing. An acetate, phosphate, citrate or glutamate buffer may be added allowing a pH of the final composition to be from about 5.0 to about 9.5; optionally a carbohydrate or polyhydric alcohol tonicifier and, a preservative selected from the group consisting of m-cresol, benzyl alcohol, methyl, ethyl, propyl and butyl parabens and phenol may also be added. Water for injection, tonicifying agents such as sodium chloride, as well as other excipients, may also be present, if desired. For parenteral administration, formulations are isotonic or substantially isotonic to avoid irritation and pain at the site of administration.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydroxyl ion added does not exceed the capacity of the buffer system to neutralize it.

Maintaining the pH of the formulation in the range of approximately 5.0 to about 9.5 can enhance the stability of the parenteral formulation of the present invention. Other pH ranges, for example, include, about 5.5 to about 9.0, or about 6.0 to about 8.5, or about 6.5 to about 8.0, or, preferably, about 7.0 to about 7.5.

The buffer used may be selected from any of the following, for example, an acetate buffer, a phosphate buffer or glutamate buffer, the most preferred buffer being a phosphate buffer. Carriers or excipients can also be used to facilitate administration of the compositions and formulations of the invention. Examples of carriers and excipients include calcium carbonate, calcium phosphate, various sugars such as lactose, glucose, or sucrose, or types of starch, cellulose derivatives, gelatin, polyethylene glycols and physiologically compatible solvents. A stabilizer may be included, but will generally not be needed. If included, however, an example of a stabilizer useful in the practice of the invention is a carbohydrate or a polyhydric alcohol. The polyhydric alcohols include such compounds as sorbitol, mannitol, glycerol, xylitol, and polypropylene/ethylene glycol copolymer, as well as various polyethylene glycols (PEG) of molecular weight 200, 400, 1450, 3350, 4000, 6000, and 8000). The carbohydrates include, for example, mannose, ribose, trehalose, maltose, inositol, lactose, galactose, arabinose, or lactose.

Isotonicity agents, or agents to maintain isotonicity, may also be used or included.

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular agent will be effective in one formulation but not effective in another formulation. While the preservative for use in the practice of the invention can range from 0.005 to 1.0% (w/v), the preferred range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid. A detailed description of each preservative is set forth in "Remington's Pharmaceutical Sciences" as well as Pharmaceutical Dosage Forms: Parenteral Medications, Vol. 1, 1992, Avis et al. For these purposes, the Type-B natriuretic signal peptide fragment agent may be administered parenterally (including subcutaneous injections, intravenous, intramuscular, intradermal injection or infusion techniques) or by inhalation spray in dosage unit formulations containing conventional non-toxic pharmaceutically acceptable carriers, adjuvants and vehicles.

If desired, the parenteral formulation may be thickened with a thickening agent such as a methylcellulose. The formulation may be prepared in an emulsified form, either water in oil or oil in water. Any of a wide variety of pharmaceutically acceptable emulsifying agents may be employed including, for example, acacia powder, a non-ionic surfactant or an ionic surfactant. It may also be desirable to add suitable dispersing or suspending agents to the pharmaceutical formulation. These may include, for example, aqueous suspensions such as synthetic and natural gums, e.g., tragacanth, acacia, alginate, dextran, sodium carboxymethylcellulose, methylcellulose, polyvinyl-pyrrolidone or gelatin.

It is possible that other ingredients may be present in a parenteral pharmaceutical formulation useful the invention. Such additional ingredients may include wetting agents, oils (e.g., a vegetable oil such as sesame, peanut or olive), analgesic agents, emulsifiers, antioxidants, bulking agents, tonicity modifiers, metal ions, oleaginous vehicles, proteins (e.g., human serum albumin, gelatin or proteins) and a zwitterion (e.g., an amino acid such as betaine, taurine, arginine, glycine, lysine and histidine). Such additional ingredients, of course, should not adversely affect the overall stability of the pharmaceutical formulation of the present invention. Regarding pharmaceutical formulations, see also, Pharmaceutical Dosage Forms: Parenteral Medications, Vol. 1, 2nd ed., Avis et al., Eds., Mercel Dekker, New York, N.Y. 1992.

Suitable routes of parenteral administration include intramuscular, intravenous, subcutaneous, intraperitoneal, subdermal, intradermal, intraarticular, intrathecal and the like. Mucosal delivery is also permissible. The dose and dosage regimen will depend upon the weight and health of the subject.

In addition to the above means of achieving extended drug action, the rate and duration of Type-B natriuretic signal peptide fragment agent delivery may be controlled by, for example by using mechanically controlled drug infusion pumps.

The Type-B natriuretic signal peptide fragment agent(s) can be administered in the form of a depot injection that may be formulated in such a manner as to permit a sustained release of the Type-B natriuretic signal peptide fragment agent. The Type-B natriuretic signal peptide fragment agent can be compressed into pellets or small cylinders and implanted subcutaneously or intramuscularly. The pellets or cylinders may additionally be coated with a suitable biodegradable polymer chosen so as to provide a desired release profile. The Type-B natriuretic signal peptide fragment agent may alternatively be micropelleted. The Type-B natriuretic signal peptide fragment agent micropellets using bioacceptable polymers can be designed to allow release rates to be manipulated to provide a desired release profile. Alternatively, injectable depot forms can be made by forming microencapsulated matrices of the Type-B natriuretic signal peptide fragment agent in biodegradable polymers such as polylactide-polyglycolide. Depending on the ratio of Type-B natriuretic signal peptide fragment agent to polymer, and the nature of the particular polymer employed, the rate of Type-B natriuretic signal peptide fragment agent release can be controlled. Depot injectable formulations can also be prepared by entrapping the Type-B natriuretic signal peptide fragment agent in liposomes, examples of which include unilamellar vesicles, large unilamellar vesicles and multilamellar vesicles. Liposomes can be formed from a variety of phospholipids, such as cholesterol, stearyl amine or phosphatidylcholines. Depot injectable formulations can also be prepared by entrapping the Type-B natriuretic signal peptide fragment agent in microemulsions that are compatible with body tissue. By way of example, reference is made to U.S. Pat. Nos. 6,410,041 and 6,362,190.

Implantable infusion devices may employ inert material such as biodegradable polymers listed above or synthetic silicones, for example, cylastic, silicone rubber or other polymers manufactured by the Dow-Corning Corporation. The polymer may be loaded with Type-B natriuretic signal peptide fragment agent and any excipients. Implantable infusion devices may also comprise a coating of, or a portion of, a medical device wherein the coating comprises the polymer loaded with Type-B natriuretic signal peptide fragment agent and any excipient. Such an implantable infusion device may be prepared as disclosed in U.S. Pat. No. 6,309,380 by coating the device with an in vivo biocompatible and biodegradable or bioabsorbable or bioerodibleerodible liquid or gel solution containing a polymer with the solution comprising a desired dosage amount of Type-B natriuretic signal peptide fragment agent and any excipients. The solution is converted to a film adhering to the medical device thereby forming the implantable Type-B natriuretic signal peptide fragment agent-deliverable medical device. An implantable infusion device may also be prepared by the in situ formation of a Type-B natriuretic signal peptide fragment agent containing solid matrix as disclosed in U.S. Pat. No. 6,120,789. Implantable infusion devices may be passive or active, as known in the art.

Also useful in methods of the invention are microemulsions, i.e., such as fluid and stable homogeneous solutions composed of a hydrophilic phase, a lipophilic phase, at least one surfactant (SA) and at least one cosurfactant (CoSA). Examples of suitable surfactants include mono-, di- and triglycerides and polyethylene glycol (PEG) mono- and diesters. A cosurfactant, also sometimes known as "co-surface-active agentm," is a chemical compound having hydrophobic character, intended to cause the mutual solubilization of the aqueous and oily phases in a microemulsion. Examples of suitable co-surfactants include ethyl diglycol, lauric esters of propylene glycol, oleic esters of polyglycerol, and related compounds.

Type-B natriuretic signal peptide fragment agents may also be delivered using various polymers to enhance bioavailability by increasing adhesion to mucosal surfaces, by decreasing the rate of degradation by hydrolysis or enzymatic degradation of the Type-B natriuretic signal peptide fragment agent, and by increasing the surface area of the Type-B natriuretic signal peptide fragment agent relative to the size of the particle. Suitable polymers can be natural or synthetic, and can be biodegradable or non-biodegradable. Delivery of low molecular weight active agents, such as for example Type-B natriuretic signal peptide fragment agents, may occur by either diffusion or degradation of the polymeric system. Representative natural polymers include proteins such as zein, modified zein, casein, gelatin, gluten, serum albumin, and collagen, polysaccharides such as cellulose, dextrans, and polyhyaluronic acid. Synthetic polymers are generally preferred due to the better characterization of degradation and release profiles. Representative synthetic polymers include polyphosphazenes, poly(vinyl alcohols), polyamides, polycarbonates, polyacrylates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes and copolymers thereof. Examples of suitable polyacrylates include poly(methyl methacrylate), poly(ethyl methacrylate), poly (butyl methacrylate), poly(isobutyl methacrylate), poly (hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate). Synthetically modified natural polymers include cellulose derivatives such as alkyl celluloses, hydroxyalkyl celluloses, cellulose ethers, cellulose esters, and nitrocelluloses. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt. Each of the polymers described above can be obtained from commercial sources such as Sigma Chemical Co., St. Louis, Mo., Polysciences, Warrenton, Pa., Aldrich Chemical Co., Milwaukee, Wis., Fluka, Ronkonkoma, N.Y., and BioRad, Richmond, Calif. or can be synthesized from monomers obtained from these suppliers using standard techniques.

The polymers described above can be separately characterized as biodegradable, non-biodegradable, and bioadhesive polymers. Representative synthetic degradable polymers include polyhydroxy acids such as polylactides, polyglycolides and copolymers thereof, poly(ethylene terephthalate), poly(butic acid), poly(valeric acid), poly(lactide-co-caprolactone), polyanhydrides, polyorthoesters and blends and copolymers thereof. Representative natural biodegradable polymers include polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein and copolymers and blends thereof, alone or in combination with synthetic polymers. Examples of non-biodegradable polymers include ethylene vinyl acetate, poly(meth)acrylic acid, polyamides, polyethylene, polypropylene, polystyrene, polyvinyl chloride, polyvinylphenol, and copolymers and mixtures thereof. Hydrophilic polymers and hydrogels tend to have bioadhesive properties. Hydrophilic polymers that contain carboxylic groups (e.g., poly[acrylic acid]) tend to exhibit the best bioadhesive properties. Polymers with the highest concentrations of carboxylic groups are preferred when bioadhesiveness on soft tissues is desired. Various cellulose derivatives, such as sodium alginate, carboxymethylcellulose, hydroxymethylcellulose and methylcellulose also have bioadhesive properties. Some of these bioadhesive materials are water-soluble, while others are hydrogels. Polymers such as hydroxypropylmethylcellulose acetate succinate (HPMCAS), cellulose acetate trimellitate (CAT), cellulose acetate phthalate (CAP), hydroxypropylcellulose acetate phthalate (HPCAP), hydroxypropylmethylcellulose acetate phthalate (HPMCAP), and methylcellulose acetate phthalate (MCAP) may be utilized to enhance the bioavailability of Type-B natriuretic signal peptide fragment agents with which they are complexed. Rapidly bioerodible polymers such as poly (lactide-co-glycolide), polyanhydrides, and polyorthoesters, whose carboxylic groups are exposed on the external surface as their smooth surface erodes, can also be used for bioadhesive Type-B natriuretic signal peptide fragment agent delivery systems. In addition, polymers containing labile bonds, such as polyanhydrides and polyesters, are well known for their hydrolytic reactivity. Their hydrolytic degradation rates can generally be altered by simple changes in the polymer backbone. Upon degradation, these materials also expose carboxylic groups on their external surface, and can also be used as B natriuretic signal peptide fragment agent delivery systems.

Other agents that may enhance bioavailability or absorption of one or more Type-B natriuretic signal peptide fragment agents can act by facilitating or inhibiting transport across the intestinal mucosa. For example, agents that increase blood flow, such as vasodilators, may increase the rate of absorption of orally administered Type-B natriuretic signal peptide fragment agent by increasing the blood flow to the gastrointestinal tract. Vasodilators constitute another class of agents that may enhance the bioavailability of Type-B natriuretic signal peptide fragment agents.

Other mechanisms of enhancing bioavailability of the compositions and formulations useful in the invention include the inhibition of reverse active transport mechanisms. For example, it is now thought that one of the active transport mechanisms present in the intestinal epithelial cells is p-glycoprotein transport mechanism which facilitates the reverse transport of substances, which have diffused or have been transported inside the epithelial cell, back into the lumen of the intestine. Inhibition of this p-glycoprotein mediated active transport system will cause less drug to be transported back into the lumen and will thus increase the net drug transport across the gut epithelium and will increase the amount of drug ultimately available in the blood. Various p-glycoprotein inhibitors are well known and appreciated in the art. These include, water soluble vitamin E; polyethylene glycol; poloxamers including Pluronic F-68; Polyethylene oxide; polyoxyethylene castor oil derivatives including Cremophor EL and Cremophor RH 40; Chrysin, (+)-Taxifolin; Naringenin; Diosmin; Quercetin; and the like.

Thus, while the delivery period will be dependent upon both the condition and the agent and the therapeutic effect which is desired, continuous or slow-release delivery for about 0.5-1 hour, about 1-2 hours, about 2-4 hours, about 4-6 hours, about 6-8, or about 24 hours or longer is provided. In accordance with the present invention, this is achieved by inclusion of a Type-B natriuretic signal peptide fragment agent, alone or toether with another cardiovascular therapeutic agent, in a formulation together with a pharmaceutically acceptable carrier or vehicle, particularly in the form of a formulation for continuous or slow-release administration.

As noted, the one or more agents of the invention may be administered before, during, immediately following a procedure in or on a subject, for example an angioplasty procedure or other physical intervention, such as stenting. They are preferably administered, for example, before and/or during a procedure or within about 24, about 12, about 10, about 9, about 8, about 7, about 6, about 5, about 4, about 3, about 2 hours or within about 60, about 45, about 30, about 15, about 10, about 5, about 4, about 3, about 2, about 1 minute following a procedure, for example.

The routes of administration and dosages described herein are intended only as a guide since a skilled physician will consider the optimum route of administration and dosage for any particular patient and condition.

Any of the methods of treating a subject having or at risk for a cardiovascular disorder may utilize the administration of any of the doses, dosage forms, formulations, and/or compositions herein described.

Pharmaceutical Compositions

The present invention is directed to pharmaceutical compositions and their methods of use for preventing and/or treating a cardiovascular disorder wherein the composition comprises a therapeutically effective amount of a Type-B natriuretic signal peptide fragment agent, alone or together with another cardiovascular therapeutic agent.

Accordingly, in one aspect, the invention provides compositions for use in preventing and/or treating a cardiovascular disorder, which comprises or consists essentially of at least one Type-B natriuretic signal peptide fragment agent, alone or together with another cardiovascular therapeutic agent. In a preferred embodiment, the composition further comprises a pharmaceutically acceptable carrier or vehicle.

In one preferred form, the composition contains one or more Type-B natriuretic signal peptide fragment peptide agents. Most preferably, the agent is BNPsp(17-26) (SEQ.ID.NO:1).

Kits, Medicaments and Articles of Manufacture

A Type-B natriuretic signal peptide fragment agent may also be used in the manufacture of the medicament for preventing and/or treating a cardiovascular disorder and related disorders and conditions.

In one aspect, the invention provides a kit for preventing and/or treating a cardiovascular disorder comprising one or more compositions or formulations described. For example, the invention includes a kit comprising a composition comprising a therapeutically effective amount of a Type-B natriuretic signal peptide fragment agent, alone or in combination with one or more cardiovascular therapeutic agents. For example, the kit may include a composition comprising an effective amount of a Type-B natriuretic signal peptide fragment agent and or more of the following: nitrates, β-blockers, calcium channel blockers (particularly for stable or unstable angina, but also for heart failure in the case of β-blockers); diuretic agents, vasodilator agents, positive inotropes, ACE inhibitors and aldosterone antagonists, e.g. spironolactone (particularly for heart failure); blood thinning therapeutics (e.g., aspirin, heparins, warfarins) and nitroglycerin (particularly for MI). Kits may also include compositions comprising or consisting essentially of a Type-B natriuretic signal peptide fragment agent in alone or in combination with (e.g., in physical combination, provided as a combined preparation) one or more anti-thrombolytic therapies (e.g., streptokinase inhibitors, anti-platelet thereapetuics, such as, for example, clopidogrel). Kits may also include a Type-B natriuretic signal peptide fragment agent alone or in combination with (e.g., in physical combination, provided as a combined preparation) a Type-B natriuretic peptide, including for example nesiritide, and/or a recombinant form of Type-B natriuretic peptide.

Articles of manufacture are also provided comprising a vessel containing a composition or formulation of the invention (in any dose or dose form or device) as described herein and instructions for use for the treatment of a subject. For example, in another aspect, the invention includes an article of manufacture comprising a vessel containing a therapeutically effective amount of a Type-B natriuretic signal peptide fragment agent, alone or in combination with one or more other cardiovascular therapeutic agents.

Treatment

The compositions and formulations of the invention may be used for preventing and/or treating a cardiovascular disorder and related disorders and conditions.

The inventions also include methods of treatment of a subject having or at risk for developing a cardiovascular disease, disorder or condition, comprising administering to the subject a therapeutically effective amount of one or more of the compounds or pharmaceutical compositions described herein. In one non-limiting embodiment, the cardiovascular disease, disorder or condition is associated with ischemia and/or oxidative stress. In one embodiment, the cardiovascular disease, disorder or condition is an acute coronary syndrome, e.g., ST-segment elevation myocardial infarction, non-ST-segment elevation myocardial infarction or unstable angina. In another embodiment, the cardiovascular disease, disorder or condition is heart failure. In other embodiments, the cardiovascular disease, disorder or condition is ischemic heart disease. In another embodiment, the cardiovascular disease, disorder or condition is stable angina.

The inventions include methods of treating a subject having or at risk for developing a cardiovascular disease, disorder or condition, comprising a therapeutically effective amount of a Type-B natriuretic signal peptide fragment agent and a pharmaceutically acceptable carrier. In one embodiment, the Type-B natriuretic signal peptide fragment agent in the pharmaceutical composition is BNPsp(17-26) (SEQ ID NO:1). In another embodiment, the Type-B natriuretic signal peptide fragment in the pharmaceutical composition comprises or consists essentially of a sequence selected from SEQ.ID.NOS:2 to 9. In another embodiment, the Type-B natriuretic signal peptide fragment agent in the pharmaceutical composition comprises or consists essentially of a sequence selected from Formula I, Formula II, Formula III, Formula IV, Formula V, Formula VI, Formula VII and/or Formula VIII. Type-B natriuretic signal peptide fragment agents also include active analogs, variants, truncations, and modified forms of the Type-B natriuretic signal peptide fragment agents described herein.

In another aspect, the inventions include methods of treating and/or preventing a cardiovascular disease, disorder or condition that is associated with ischemia and/or oxidative stress in a subject by increasing Type-B natriuretic signal peptide fragment activity in the subject. This may be accomplished, for example, by administering to the subject a composition comprising a therapeutically effective amount of a Type-B natriuretic signal peptide fragment agent, e.g., a Type-B natriuretic signal peptide fragment or a Type-B natriuretic signal peptide fragment, including a BNPsp fragment comprising or consisting essentially of a sequence selected from SEQ.ID.NOS:1-9, or a peptide comprising or consisting essentially of a peptide according to any of Formulae I to VIII, or an analog, variant, truncation or modification thereof. In certain embodiments, doses described above are utilized. In other embodiments, about 0.01 to about 100, 500 or 1000 milligrams or more (e.g., at least about 100 milligrams, at least about 500 milligrams, or at least about 1000 miligrams) of a BNPsp fragment or Type-B natriuretic signal peptide fragment analog, e.g., a BNPsp fragment comprising or consisting essentially of a sequence selected from SEQ.ID.NOS:1-9, or a peptide comprising or consisting essentially of a peptide according to any of Formulae I to VIII, is administered per day in single or divided doses or by continuous infusion, for example.

In another aspect, the inventions include methods of treating a patient suffering from acute coronary syndrome, comprising administering to the patient a therapeutically effective amount of a Type-B natriuretic signal peptide fragment agent, wherein the patient is not suffering from a Q-wave MI or STEMI. In a certain embodiment of this method, the patient is suffering from unstable angina. In another embodiment of this method, the patient is suffering from non-Q-wave cardiac necrosis. In still another embodiment of this method, the patient has a blood troponin I level of no more than 0.4 ng/ml. In yet another embodiment of this method, the patient has a blood troponin T level of no more than 0.1 ng/ml. In yet another embodiment of this method, the patient does not have elevated blood creatine kinase. In still another embodiment of this method, the patient does not have ST-segment elevation. In yet another embodiment of this method, the patient does not exhibit a pathological Q-wave. In another embodiment of this method, the patient exhibits one or more of the following symptoms: chest rain greater than 15 minutes in duration, chest pain at rest, or chest pain following minimal exertion that is poorly responsive to sublingual nitrates.

In one embodiment, the Type-B natriuretic signal peptide fragment agent is administered in a single dose. In another embodiment, the Type-B natriuretic signal peptide fragment agent is administered in more than one dose. In yet another embodiment, the Type-B natriuretic signal peptide fragment agent is administered continuously over a period of time, for example a predetermined period of time. In still another embodiment, glucose or a potassium salt, or a combination thereof, is co-administered with the Type-B natriuretic signal peptide fragment agent.

In another aspect, the inventions include methods for treatment of a patient, comprising administering to the individual a therapeutically effective amount of a Type-B natriuretic signal peptide fragment agent, wherein the administration is after the onset of one or more of the following symptoms: chest pain lasting longer than 15 minutes, chest pain at rest, chest pain following minimal exertion, nausea, shortness of breath, palpitations, or dizziness. In other embodiments, the patient has not suffered a Q-wave MI or STEMI prior to the onset of the symptom or symptoms; patient is suffering from unstable angina; the patient is suffering from non-Q-wave cardiac necrosis; the patient has a blood troponin I level of no more than 0.4 ng/ml; the patient has a blood troponin T level of no more than 0.1 ng/ml; the patient does not have elevated blood creatine kinase myocardial isoenzyme; the patient does not have ST-segment elevation; the patient does not exhibit a pathological Q-wave; the administration occurs between the time of onset of the one or more symptoms, and the time the patient suffers a Q-wave MI or STEMI. In another embodiment, the method further comprises the step of continuing the administration of a Type-B natriuretic signal peptide fragment agent during the time that the patient suffers a Q-wave MI or STEMI. In yet another embodiment, the method further comprises the step of continuing the administration of a Type-B natriuretic signal peptide fragment agent after the time the patient suffers a Q-wave MI or STEMI. In other embodiments of this method, the patient has ischemic heart disease, or is at risk for developing ischemic heart disease. In still another embodiment of the method, the patient has one or more of the following cardiac abnormalities: congestive heart failure, worsening heart murmur due to mitral regurgitation, or evidence of cardiac conduction disturbances. In other embodiments, the patient has a normal ECG. In another embodiment of this method, the patient has stable angina. In other embodiments of the method, the Type-B natriuretic signal peptide fragment agent is administered in a single dose, or is administered in more than one dose, or is administered continuously. In an additional embodiment of this method, glucose or a potassium salt, or a combination thereof, is co-administered with the Type-B natriuretic signal peptide fragment agent.

The inventions also include methods for treating a patient suffering from stable angina, comprising administration of a Type-B natriuretic signal peptide fragment agent. In a further embodiment, the administration is continuous over a period of time, including a predetermined period of time.

The inventions also provide a method for performing angioplasty on a patient in need thereof, comprising administering a Type-B natriuretic signal peptide fragment agent to the patient during the angioplasty procedure. In a further embodiment, the method comprises or further comprises administering a Type-B natriuretic signal peptide fragment agent to the patient prior to the angioplasty procedure. In a further embodiment, the method comprises or further comprises administering a Type-B natriuretic signal peptide fragment agent to the patient following the angioplasty procedure. In other embodiments, a Type-B natriuretic signal peptide fragment agent is administered to the patient before, during, and/or after the angioplasty procedure, in any combination.

The inventions also include methods for treatment of a patient with ischemic heart disease, or is at risk for developing ischemic heart disease, including patients who exhibit one or more of the following symptoms: nausea, shortness of breath, palpitations, or dizziness, and further wherein the patient does not exhibit chest pain, comprising administering to the patient a therapeutically effective amount of a Type-B natriuretic signal peptide fragment agent, wherein the patient is not suffering a Q-wave MI or STEMI. In another embodiment of this method, the patient has a normal ECG.

Also provided are methods for increasing the time during which thrombolytic therapy will be effective following the first symptom of cardiac distress, comprising administering a therapeutically effective amount of a Type-B natriuretic signal peptide fragment agent after the onset of one or more of the following symptoms: chest pain lasting longer than 15 minutes, chest pain at rest, chest pain following minimal exertion, nausea, shortness of breath, palpitations, or dizziness.

In another aspect, the treated subject is a mammal, preferably a human. Other rmammals include domestic and farm animals, and zoo, sports, or pet animals, such as dogs, horses, and cats.

In one aspect the invention is directed to sustained administration of a Type-B natriuretic signal peptide fragment agent and, optionally, another cardiovascular therapeutic agent. In one embodiment, the agent(s) are administered for at least about 0.5 hours, about 1-24 hours, at least about 2, hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours or at least about 24 hours.

Any of the methods of treating a subject having or suspected of having or predisposed to a disease, disorder, and/or condition referenced or described herein may utilize the administration of any of the doses, dosage forms, formulations, compositions and/or devices herein described.

A better understanding of the invention will be gained by reference to the following non-limiting experimental section which is illustrative and is not intended to limit the invention or the claims in any way. The data support the use of the compounds and compositions described herein for treatment of cardiovascular diseases, disorders and conditions, as described.

EXAMPLES

Data show that BNPsp(17-26) is rapidly cleared from the circulation. However, it has been unexpectedly and surprisingly discovered that compounds, such as BNPsp(17-26) for example, can act as a protective/therapeutic agent in, by way of example, experimental cardiac ischemia and infarction.

Animal models may be used to test the efficacy of the administration of compounds of the invention to an individual with a cardiovascular disorder, such as unstable angina, for example, a disorder within the ACS spectrum, whether or not they have yet suffered an actual infarction. Rat models and sheep models have been found to be particularly well suited for this purpose. In rats, BNPsp(17-26) administered during the last 3 minutes of a 40 min ischemia period and then throughout a 2-hour reperfusion period significantly reduced infarct size (−30%), and the rats also had significantly improved hemodynamics. In sheep, administration of BNPsp(17-26) significantly reduced the stunning period, during reperfusion after a period of subcritical ischemia.

Methods showing cardioprotective properties of compounds of the invention, such as BNPsp(17-26) and other BNPsp fragments for example, are provided. The Examples include experiments showing cardioprotection in an in vitro isolated rat heart ischemia model, and in an in vivo sheep model of myocardial infarction.

Example 1

Rat Heart Ischemia Model

Isolated Rat Heart.

Male Sprague-Dawley rats weighing 250 g to 350 g were anesthetized by sodium pentobarbitone (50 mg/kg i.p.) and sacrificed by decapitation. The isolated, Langendorff perfused rat heart set up was prepared as previously described. Pemberton et al., Ghrelin induces vasoconstriction in the rat coronary vasculature without altering cardiac peptide production. *Am J. Physiol* (Heart and Circ. Physiology) 2004 287: H1522-H1529; Piuhola et al., Direct Cardiac actions of erythropoietin (EPO): effects on cardiac contractility, BNP secretion and ischemia-reperfusion injury. *Clinical Science* 2008 114: 293-304.

Left ventricular end diastolic pressure (LVEDP), developed pressure (DP) and the maximal and minimal derivatives of the left ventricular pressure ($+dP/dt_{max}$ and $-dP/dt_{min}$, respectively) were measured with a liquid-filled balloon in the left ventricle. Perfusion pressure was monitored with a side arm cannula above the aortic root. A constant flow rate of 12 mL/min was maintained with a peristaltic pump (Gilson Minipuls, model MP-2). The animal ethics committee of the Christchurch School of Medicine, University of Otago approved the study protocol. The investigation conforms to the *Guide for the Care and Use of Laboratory Animals* published by the US National Institutes of Health (NIH publication no. 85-23, revised 1996).

Ischemia-Reperfusion Protocol.

The preparations for ischemia-reperfusion experiments were paced with a stimulator (Digitimer Ltd., England) using a bipolar electrode placed on the right atrium (15 V, 1 ms, 300 bpm). The temperature in the moisturized chamber where the heart was positioned was monitored to remain between 35-37° C. throughout the experiments. In this set of experiments, the cardioprotective effects of increasing doses of BNPsp(17-26) were evaluated (0.1, 0.3, 1.0, 3.0 and 10.0 nMoles/L). These doses are equivalent to about 0.1, 0.3, 1.0, 3.0, and 10-11 µg/L and administrable weight doses of about 400, 1000, 4000, 10,000 and 39,000 ng/kg or about 0.4, 1.0, 4.0, 10 and 39 micrograms/kg. Doses were compared under two different strategies: (1) a preconditioning effect prior to 45 minutes of global ischemia ("PRE"), and (2) a direct, "real time" effect given at the initiation of 120 minutes reperfusion ("IDR"). The treatments were given, respectively, for 30 minutes either prior to ischemia or starting at the time of reperfusion. During the reperfusion, 35 minutes after reinitiating the coronary flow, the LVEDP was temporarily set to 5 mmHg by adjusting intraventricular balloon volume to obtain contractile parameters with comparable end-diastolic pressure.

Measurement of Perfusate cTnI and Myoglobin.

Cardiac troponin I ("cTnI") levels in isolated heart perfusate were measured on a hospital laboratory high throughput analyser (Abbott Architect, Canterbury Health Laboratories, Christchurch Hospital, New Zealand), using a late generation cTnI assay. Myoglobin was measured using a Chemiluminescent Microparticle Immunoassay (Canterbury Health Labs, Christchurch, New Zealand) on an Abbot Architect i2000 analyser.

Tissue is also analysed for markers of apoptosis, namely TUNEL staining and caspase 3 determination. Trypan blue exclusion (0.4% trypan in PBS) is performed to provide an estimate of necrotic cells. Three regions with in the infarct territory are analyzed. The number is expressed as a percentage of necrotic cells out of 250 cells.

TUNEL Staining.

DNA fragmentation [terminal deoxynucleotidyltransferase-mediated UTP end-labeling (TUNEL) assay] was detected from formalin fixed sections of LV free wall using a kit from Chemicon International according to the manufacturer's protocol, as previously reported. Piuhola et al., Direct Cardiac actions of erythropoietin (EPO): effects on cardiac contractility, BNP secretion and ischemia-reperfusion injury. *Clinical Science* 2008 114: 293-304. From each heart a cross section at mid ventricle level was used for staining and all the TUNEL positive cells were counted. Sections were counterstained with DAPI to determine the total number of cells.

Immunohistochemical Detection of Cleaved Caspase-3.

Caspase-3 is one of the terminal effectors of the apoptotic cascade. It exists in cells as an inactive 32 kDa protein, and in apoptotic cells it is cleaved to 20/17 kDa active form. An immunohistochemical technique for detection of cleaved caspase-3 was used. Briefly, formalin-fixed sections were deparaffinized, rehydrated and incubated in 1% $H_2O_2$ for 30 min to quench endogenous peroxidase. Following antigen retrieval with heat, the sections were incubated overnight at 4° C. with a polyclonal rabbit antibody recognizing the cleaved form of human caspase-3 (Cell Signaling Technology, Beverly, Mass.). Primary antibody binding was detected with peroxidase labelled polymer conjugated to goat anti-rabbit immunoglobulins (DAKO Corporation, Carpinteria, Calif.) and diaminobenzidine solution (DAKO) used as the substrate. The tissues were lightly counterstained with haematoxylin. PBS replaced the primary antibody as negative control for these experiments. The mean number of caspase-3 positive cells per 7 randomly selected 40× objective fields was counted in each sample.

Isolation of Mitochondrial and Cytosolic Proteins.

Cardiac LV free walls were homogenized in a buffer containing 250 mM sucrose, 10 mM Tris, 1 mM EDTA, protease inhibitors and phosphatase inhibitors. The lysate was centrifuged for 5 min at 1000 g to pellet the unbroken cells and the nuclei. The supernatant was further centrifuged 20 min at 13,000 g to pellet the mitochondria. The pellet was resuspended in homogenization buffer and further washed twice with the same buffer. Finally, the mitochondrial pellet was resuspended in solubilization buffer consisting of 150 mM NaCl, 20 mM Tris, 10 mM EDTA, 1% NP-40, protease inhibitors and phosphatase inhibitors. After 30-minute incubation on ice the lysate was centrifuged 10 min at 13,000 g to pellet the unsoluble material. The supernatant was further centrifuged 60 min at 100,000 g to separate the cytosolic fraction (the supernatant).

Assessment of BNPsp(17-26) Activity in Isolated Perfused Rat Heart.

Mass spectrometry was used to document oxidative stress reaction product addition to unmodified BNPsp(17-26) in isolated rat heart perfusate samples. Two samples were analysed: the first was 10 nmol/L unmodified BNPsp(17-26) in isolated heart perfusate that had not passed through an ischemic heart; the second was 10 nmol/L BNPsp(17-26) that had passed through a rat heart that had undergone no flow ischemia for 45 minutes. BNPsp(17-26) was added at the time of reperfusion and sample was collected for 3 minutes after flow initiation.

Perfusate sample were extracted on solid phase cartridges (Pemberton et al., Ghrelin induces vasoconstriction in the rat coronary vasculature without altering cardiac peptide production. *Am J. Physiol* (Heart and Circ. Physiology) 2004 287: H1522-H1529) and further purified by size-exclusion high performance liquid chromatography (SE-HPLC) using a isocratic gradient of 60% acetonitrile/0.1% trifluoroacetic acid (TFA). Immunoreactive BNPsp(17-26) was quantitated by immunoassay (Piuhola et al., Direct Cardiac actions of erythropoietin (EPO): Effects on cardiac contractility, BNP secretion and ischemia-reperfusion injury. *Clinical Science* 2008 114: 293-304) and then structurally assessed by matrix assisted laser desorption/ionization time of flight mass spectroscopy (MALDI-TOF MS). All MS spectra were acquired in positive-ion mode with 800-1000 laser pulses per sample spot. A maximum of six precursor ions of each sample spot were selected for MS/MS collision-induced fragmentation (CID) analysis. Structural modifications to BNPsp(17-26) were analysed by LC-$MS^3$ LTQ-OrbitrapXL mass spectrometry (Thermo Scientific, San Jose, Calif.). Eluting peptides were monitored by a full mass scan using the linear ion trap in a mass range from m/z 400-1400. The predicted m/z value of the doubly charged peptide was selected as the exclusive precursor mass triggering subsequent scan events.

Statistical Analysis.

Results are presented as mean±standard error of the mean (SEM). Multiple group comparisons were made by one-way or repeated-measures ANOVA as appropriate followed by the post hoc test for least significant differences. For the comparison between two groups, Student's t test was used. Significance was assumed at $P<0.05$. All the Statistical analyses were performed with SPSS (version 17).

Results

Isolated Rat Heart Preparations

Infusion of BNPsp(17-26) either for 30 minutes prior to (pre), or for 30 minutes immediately after (IDR), 45 minutes of ischemia resulted in significant improvements in cardiac contractility (developed pressure, FIG. 1, Panel A) and in vascular tone (perfusion pressure, FIG. 1, Panel B), compared with control infusion that utilised vehicle buffer alone. Thus, control developed pressures returned to only ~75% of pre-ischemic values, whereas pre-ischemia infusion with 0.3 nmol/L or post-ischemia infusion of 1 nmol/L BNPsp(17-26) returned developed pressures to between 110-120% pre-ischemia values (P<0.01). An element of dose response was observed and there was a trend for pre-infusion of 0.3 nmol/L BNPsp(17-26) to have positive inotropic effect prior to ischemia. Likewise, vascular tone during the post-ischemic reperfusion phase was well preserved with pre-ischemia infusion of 0.3 nmol/L BNPsp(17-26) (P<0.01) and with post-ischemia use of 0.3 and 1 nmol/L BNPsp(17-26) (P<0.05, FIG. 1, Panel B).

In agreement with the haemodynamic data, cardiac biomarker analysis revealed marked and significant reductions in both TnI and myoglobin release during the reperfusion phase after ischemia, when BNPsp(17-26) was given either pre- or post-ischemia. Exemplar results, from post-ischemia reperfusion (IDR), are shown in FIG. 1, panels C and D. Thus, both 0.3 and 1 nmol/L BNPsp(17-26) resulted in ~20% the TnI release of control infusion (Panel C, P<0.01) and ~60% the control myoglobin release (Panel D, P<0.05). Given that TnI and myoglobin release have both been correlated with size of cardiac infarct and subsequent prognosis (mortality, adverse events), these substantial BNPsp (17-26) inspired reductions have meaningful clinical utility.

Further analysis using reduced sequence variants of BNPsp reveals cardiotherapeutic and cardioprotective effects.

Taken together, these results support a favourable clinical utility for BNPsp signal peptide fragment agents in the areas of cardiotherapy and cardioprotection (before and after ischemic episodes of any cause).

These data support the concept that human BNPsp(17-26), and shorter carboxyl terminal truncated versions, as well as N-terminal addition peptides variants thereof, are powerful, clinically useful cardiotherapeutic and cardioprotective agents. Accordingly, the clinical potential for use of these peptide sequences is strong in acute cardiac coronary syndromes and other diseases, disorders and conditions noted herein. Other mammalian and lower vertebrate forms of BNPsp sequences, variants, derivatives, and analogs will also possess such therapeutic and protective properties.

Example 2

Sheep Model

Data show that BNPsp(17-26) is rapidly cleared from the circulation. However, it has been unexpectedly and surprisingly discovered that unmodified BNPsp(17-26) can act as novel protective/therapeutic agent in experimental cardiac ischemia and infarction, as indicated herein. This Example demonstrates that the compounds are safe.

Infusion of BNPsp(17-26) into two normal, healthy sheep (achieving circulating levels found to be favourably bioactive in isolated rat hearts) resulted in no detectable changes to haemodynamics, renal function or circulating biomarkers (cardiac output is an exemplar shown in FIG. 2). This is a favourable profile in normal health.

Example 3

Rat Heart Ischemia Model

Ex Vivo Isolated Perfused Rat Heart Model of Cardiac Ischemic Injury Heart.

In this Example, more than 100 male Sprague-Dawley rats were used, all male. The heart was removed the heart under global anaesthesia and placed in an it in our experimental rig setup as described in Example 1. The hearts were is perfused with a standard, well used buffer system containing glucose to provide energy and calcium to ensure the intrinsic beating activity of the heart is preserved. After equilibration, we perform two types of experiments were performed. First, we infuse the hearts were infused with either vehicle control (buffer itself) or human BNPsp(17-26) for 30 minutes prior to 40 minutes of global ischemia (referred to: this is known as pre-conditioning). Second, we infuse the hearts were infused with vehicle or human BNPsp (17-26) after ischemia (referred to: this is known as reperfusion treatment), which and more closely mimics the real clinical situation (ie. given that doctors can only invoke Tx AFTERtherapy after a heart attack has occurred). End points of interest are improvements in cardiac contractility after ischemia, reduction in cardiac troponin release, improvements in post-ischemia coronary blood pressure, reduction in infarct size. At the end of the experiment, left ventricular free wall regions were biopsied for subsequent determination of markers of apoptosis (TUNEL staining, caspase 3) and Western Blot of ERK1/2, PI3K, Akt and GSK-3β.4

TUNEL staining was done on samples of the left ventricular free wall that were fixed in 10% fomaldehyde overnight and then stored in paraffin. Prior to staining the sections were rehydrated with saline buffer and endogenous peroxidase activity blocked by incubation with 0.3% H2O2. TUNEL staining was performed as per the manufacturer's protocol (Chemicon International). The mean number of TUNEL positive cells were counted and reported as a ratio of the entire cell count per ten randomly selected 400× objective fields in each sample.

Caspase 3 staining was performed on separate slides prepared as for TUNEL staining. Prior to staining slides were rehydrated and incubated with 1% (v/v)H2O2. The hearts were incubated for hours at 4° C. with a polyclonal rabbit antibody directed towards the activated form of Caspase 3 (Cell Signalling Technology). Primary antibody binding was detected with perxidase labelled polymer conjugated with goat anti rabbit IgG (DAKO). The slides were then lightly counterstained with hematoxylin. The slides were photographed at ×400 magnification.

Isolated Rat Heart Data

Figure 3:
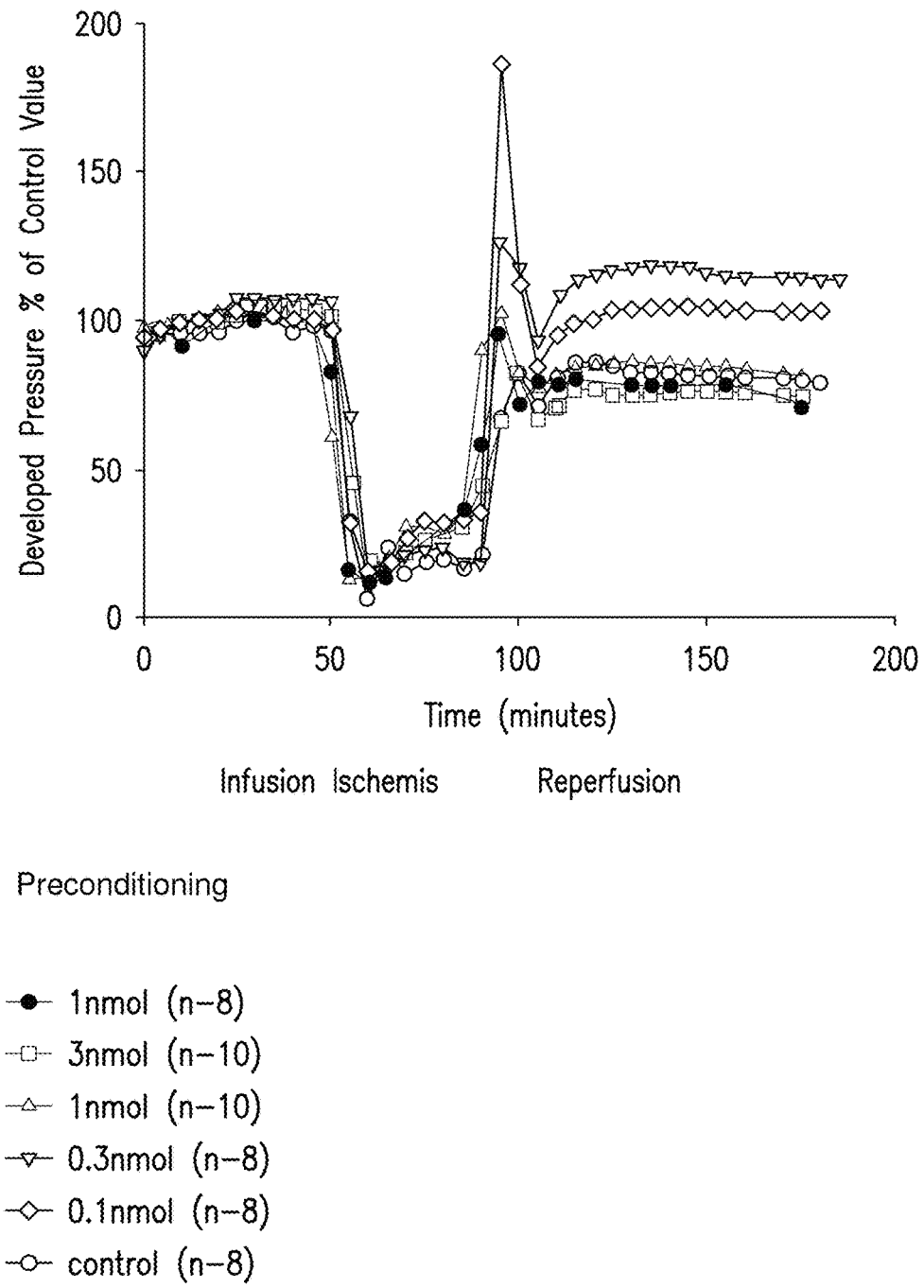
FIG. 3 shows normalized contractile function (developed pressure) in isolated hearts preconditioned with synthetic human BNPsp(17-26) and control buffer. Doses and group size are as shown.
Figure 4:
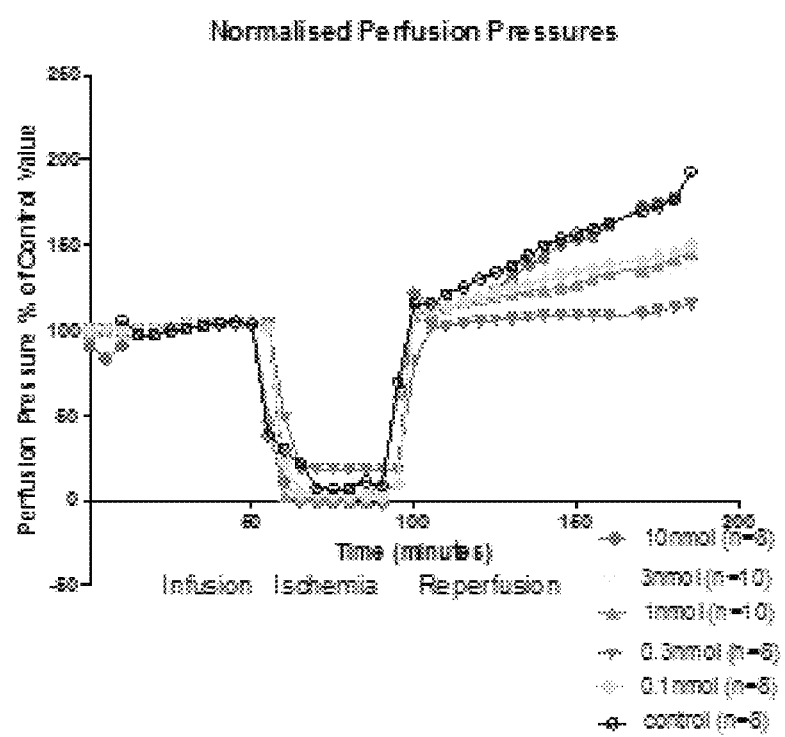
FIG. 4 shows normalized vascular function (perfusion pressure) in isolated hearts preconditioned with synthetic human BNPsp(17-26) and control buffer. Doses and group size are as shown.

Human BNPsp(17-26) reduced the damage caused to heart tissue by a period of ischemia. When hearts receiving vehicle undergo global ischemia for 40 minutes they recovered to about 70% of their pre-ischemia contractile function (developed pressure). This is true for pre-conditioned and reperfusion treatment hearts. In contrast, hearts pre-conditioned or treated at reperfusion with BNPsp(17-26) recover to slightly over 100% of their pre-ischemia contractile function (FIG. 3). Thus, when considering control versus 0.3 nmol/L BNPsp(17-26), there was a significant increase in contractility during infusion with 0.3 nmol/L concentration (+15.4% versus control, P=0.003). More importantly, during the reperfusion phase after ischemia, there were statistically significant improvements in developed pressure in the BNPsp(17-26) treated hearts (0.1-0.3 nmol/L+21% versus control, P=0.007). Analysis showed significant differences between control and 0.1 and 0.3 nmol/L with both these concentrations achieving improved contractility across all time points analyzed.

Figure 5:
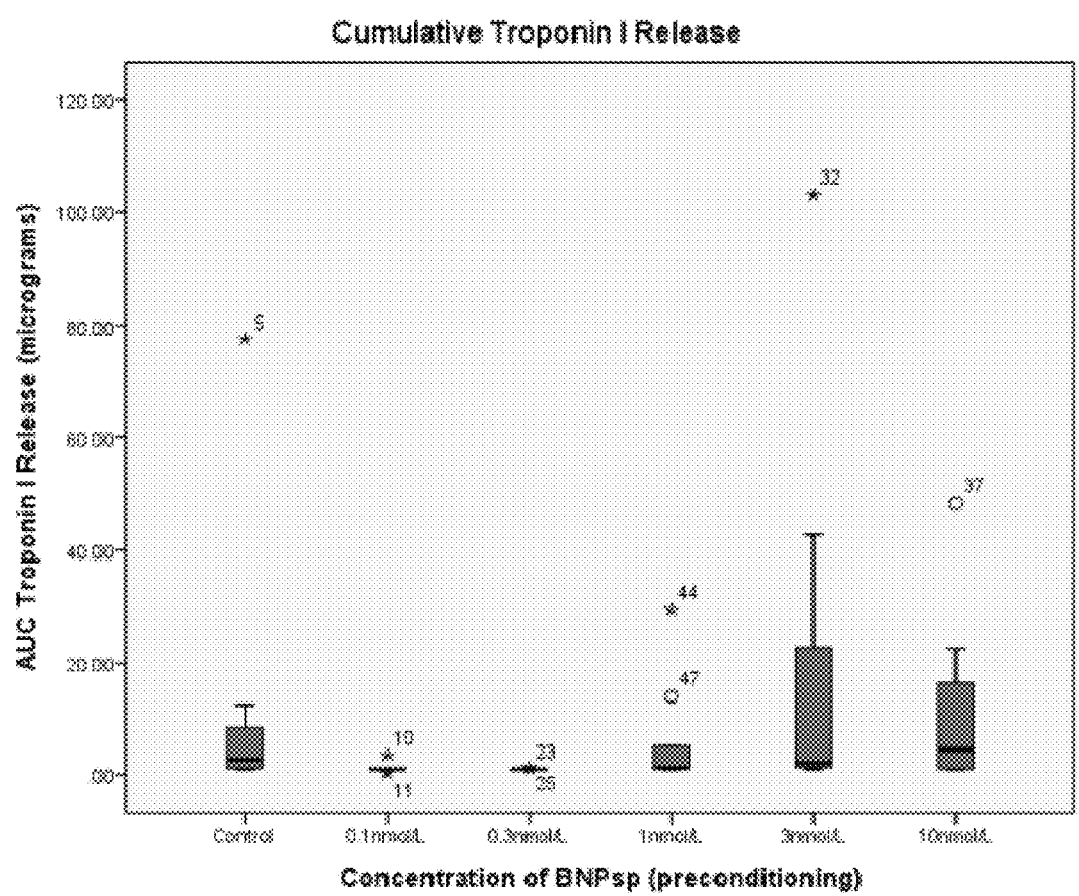
FIG. 5 shows the cumulative release of troponin I (AUC) in hearts preconditioned with synthetic human BNPsp(17-26) and control buffer. Doses and group size are as per FIGS. 3 and 4. *=P<0.01 vs. control.

Concomitant with the improvements in developed pressure, BNPsp(17-26) induces improvements in coronary vascular tone, such that there is reduced post-ischemia coronary vasoconstriction (FIG. 5). During the reperfusion stage, there were significant changes in perfusion pressures between groups. Compared with control values, repeated measures ANOVA with post-hoc analysis identified significant reductions (−25 to −50%, P=0.008) in reperfusion vascular pressures at the doses of 0.1-0.3 nmol/L BNPsp (17-26). These effects began immediately post reperfusion and continued until the end of the sampling period.

Figure 6:
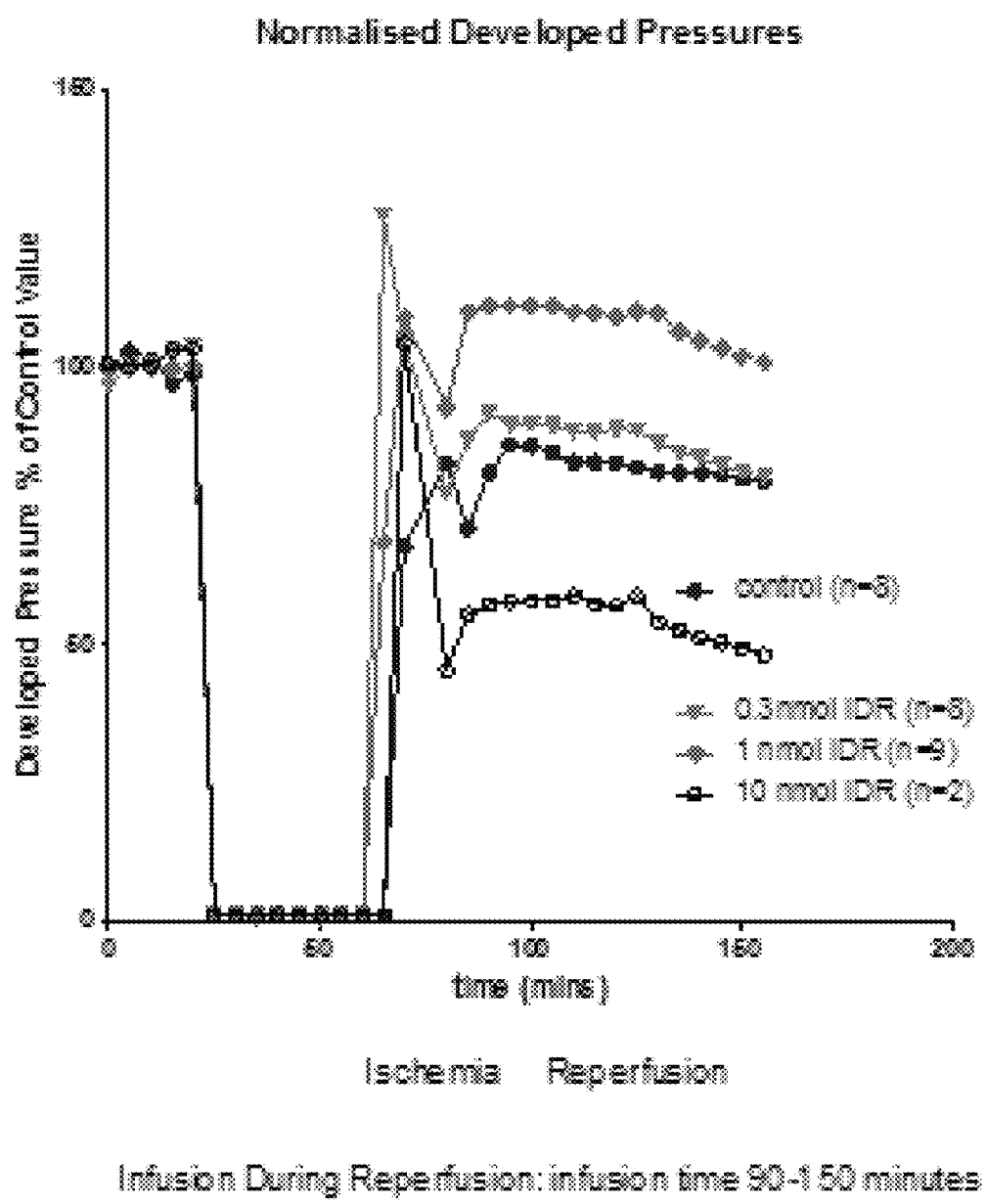
FIG. 6 shows the developed pressures in isolated hearts given BNPsp(17-26) during reperfusion after ischemia. Doses and sample size are as shown.

Following this, reperfusion-only were conducted experiments in isolated rat hearts. In rat hearts receiving 0.3-1.0 nmol/L BNPsp(17-26) at reperfusion, cardiac contractile function was significantly improved compared with control values (FIG. 6). During the reperfusion stage improved contractility was observed in the study hearts administered 0.3 and 1 nmol/L BNPsp(17-26) (+7% and +26% versus control, P=0.003, respectively).

Corresponding to this, reperfusion perfusion pressures and cardiac troponin release were also improved in hearts receiving BNPsp(17-26) (FIG. 5). During reperfusion, hearts administered 0.3 and 1 nmol/L BNPsp(17-26) had lower mean perfusion pressures (−10%, P<0.05) compared with control.

In accordance with this positive haemodynamic profile, the release of troponin I from the ischemic myocardium was significantly reduced in hearts receiving BNPsp(17-26). Thus, compared with control, there was a 50% reduction in cumulative Troponin I release in hearts administered 0.3 nmol/L (P<0.05) and a 66% reduction (P<0.01) in hearts receiving 1 nmol/L BNPsp(17-26).

Figure 8:
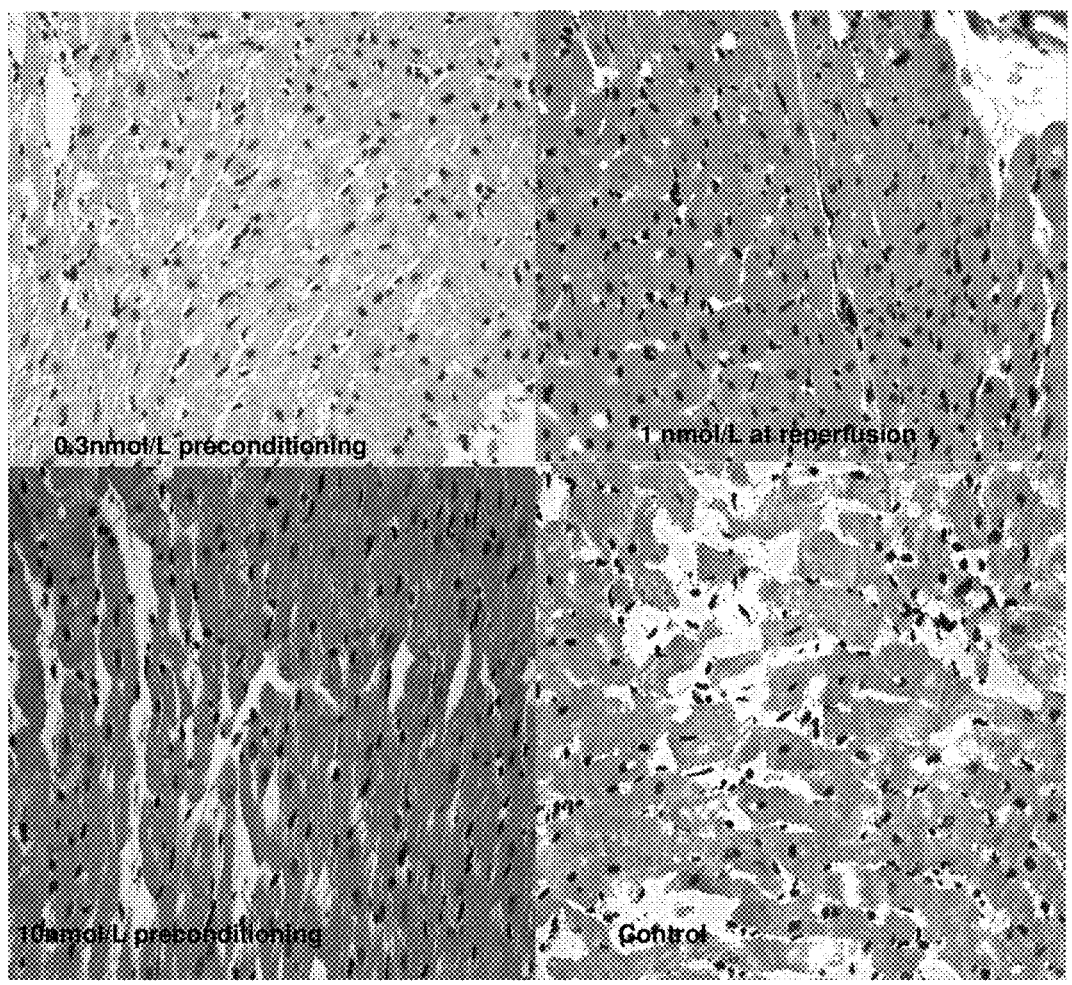
FIG. 8 shows Hematoxylin and Eosin (HE) staining demonstrating a greater degree of myocyte cell swelling and myofibrillar derangement in control hearts compared with BNPsp(17-26) treated hearts.

We also investigated the effect of BNPsp(17-26) upon markers of cellular apoptosis and necrosis. FIG. 8 displays the cellular preservation effects of BNPsp(17-26) as determined by HE staining, as indicated by improved integrity and less disruption in in form in BNPsp(17-26) treated hearts.

Figure 9:
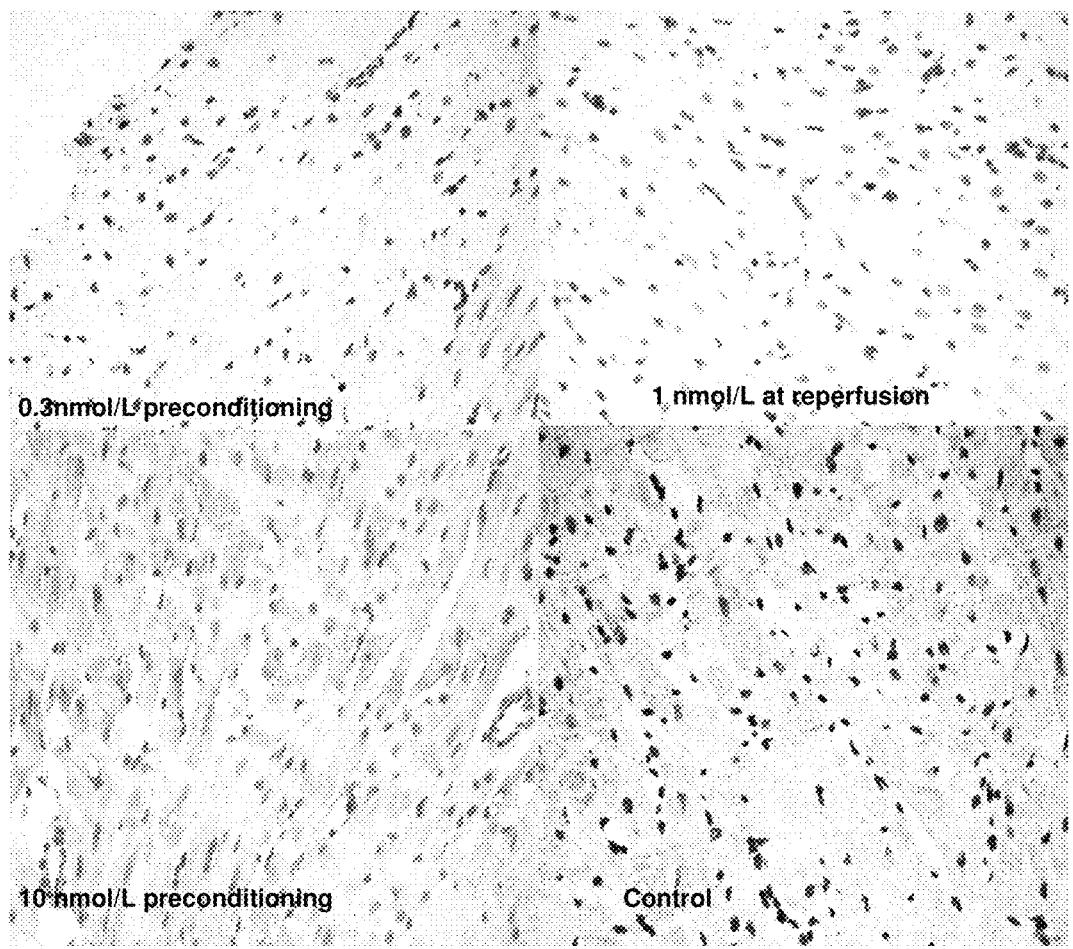
FIG. 9 shows capsase-3 staining of slides of left ventricular free wall cardiomyocytes. Caspase-3 activity is indicated by the brown colouration. Colouration was virtually absent from hearts infused with 1 nmol/L BNPsp(17-26) at reperfusion and markedly reduced in hearts preconditioned with 0.3 nmol/L BNPsp(17-26), compared with control.

Staining for caspase-3 activity is shown in FIG. 9. There was a significant reduction in caspase-3 positive cells (indicated by brown colouration) in hearts treated with BNPsp (17-26).

Figure 10:
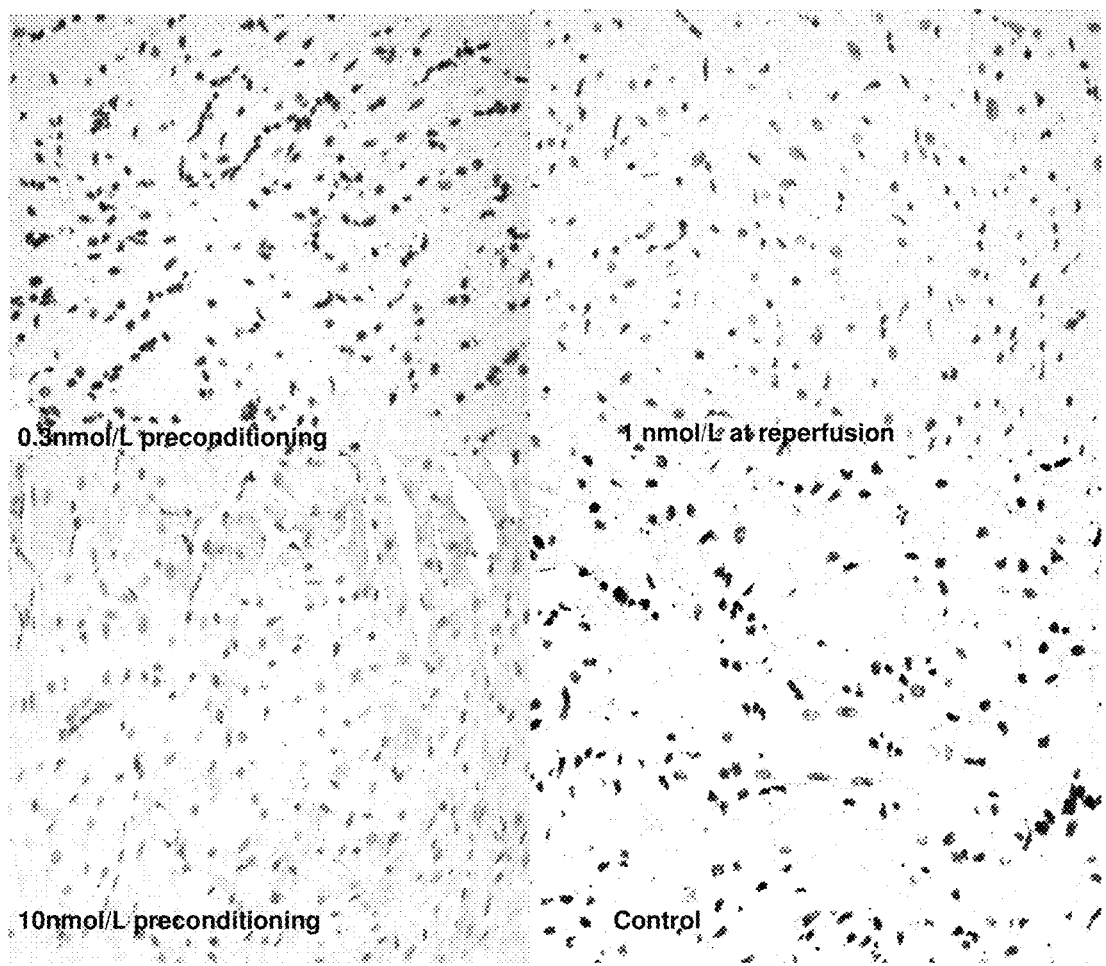
FIG. 10 shows marked reduction in TUNEL positive cells from hearts infused with BNPsp(17-26). TUNEL positive nuclei (red-brown colouration) was markedly reduced in all hearts infused with BNPsp(17-26).

Staining with TUNEL revealed less brown coloured nuclei in BNPsp(17-26) treated hearts, which indicates a greater degree of DNA integrity and less cellular fragmentation. See FIG. 10.

Example 4

In Vivo Myocardial Infarction Sheep Models (Healthy and)

Infusion of human BNPsp(17-26) during in vivo cardiac ischemia in sheep will also result in beneficial effects upon cardiac contractile function, significant reductions in release of biomarkers (troponin I, myoglobin) of necrosis and significant reductions in ventricular wall stress abnormalities that accompany remodelling after ischemia.

In this set of experiments, four normal healthy sheep were infused with human BNPsp(17-26) at 100-1000 ug/kg·min−1 to document any effects upon normal blood pressure, heart rate or renal function. This experiment was carried out to determine achieved circulating levels of BNPsp(17-26) in response to the dose given and to document any significant effects upon haemodynamic, renal or hormonal indices.

Experimental myocardial infarction was performed on 8 sham operated and 7 experimental sheep. Each sheep was surgically prepared under anaesthesia with jugular and carotid access catheters, ECG electrodes and a Swan Ganz catheter to measure cardiac output. All 15 sheep underwent 90 min ischaemia of the 2nd diagonal of the LAD coronary artery by means of a releasable snare. 30 min prior to the start of ischemia, each sheep received (depending on their group) either saline or 500 ng/kg/min BNPsp(17-26) for 120 min. Thus, this study was a pre-conditioning and during design. Serial haemodynamic recordings and venous blood sampling were taken pre-anaesthetic and then at −10, occlusion (O), O+30, O+60, O+90, and then at 120, 150, 240, and 360 min and 5, 24 and 48 hours. Serial echocardiography (basal, mid and apical regions in the short-axis plane) was performed pre, during and 30 min post occlusion.

Figure 11:
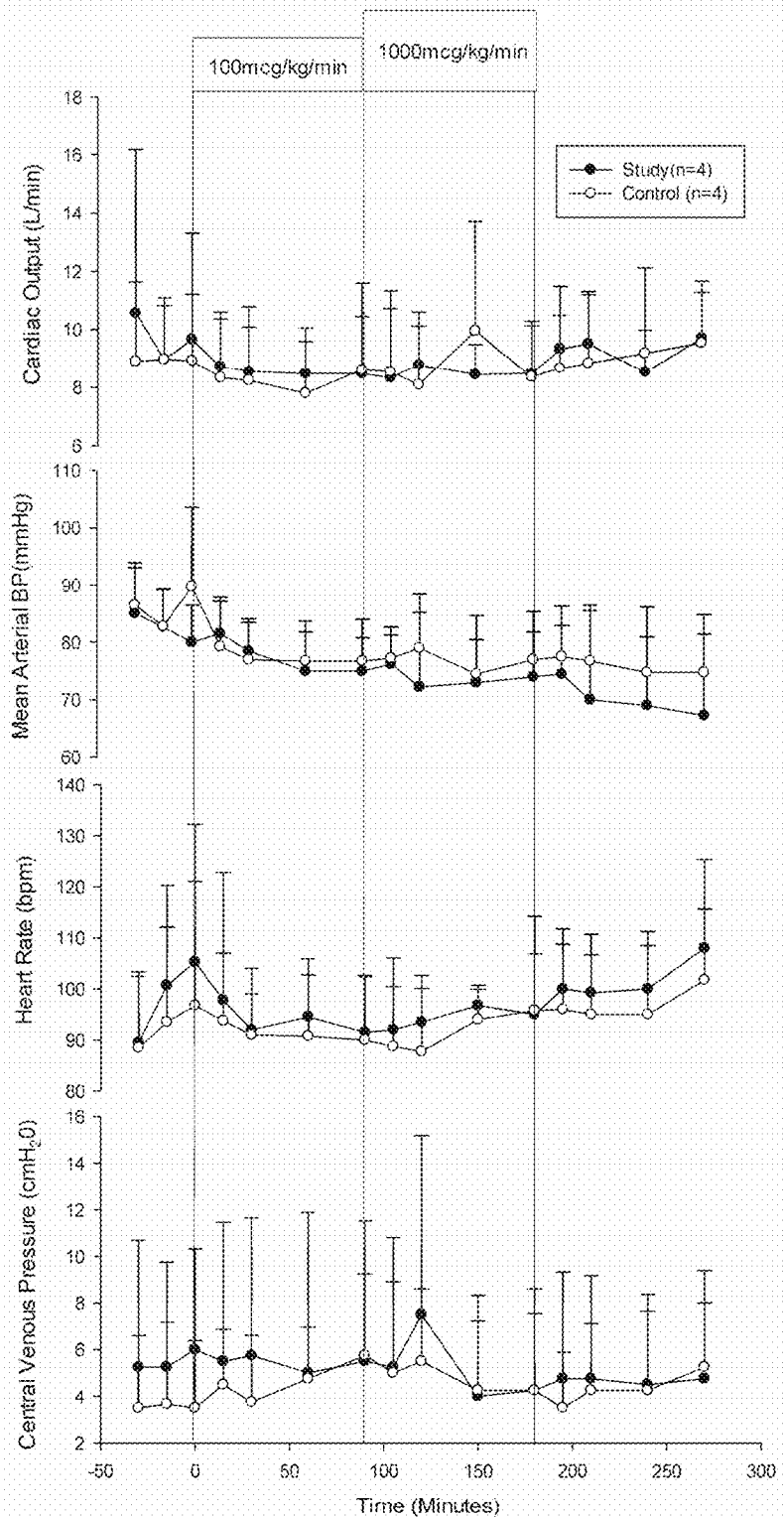
FIG. 11 shows that the infusion of human BNPsp(17-26) into 4 normal sheep at 100 and 1000 ug/kg·min had no effect upon venous pressure, heart rate, mean arterial pressure or cardiac output. Similar results were found for hormones and renal indices.

Infusion of human BNPsp(17-26) at 100-1000 ug/kg·min in 4 normal sheep had no significant effects upon haemodynamic, renal or hormonal indices (FIG. 11). The clearance of BNPsp(17-26) from the circulation in sheep was very fast, being in the order of minutes. This suggests a plasma half-life of less than 1 minute, or a very rapid proteolytic cleavage to a non-immunoreactive form.

Figure 12:
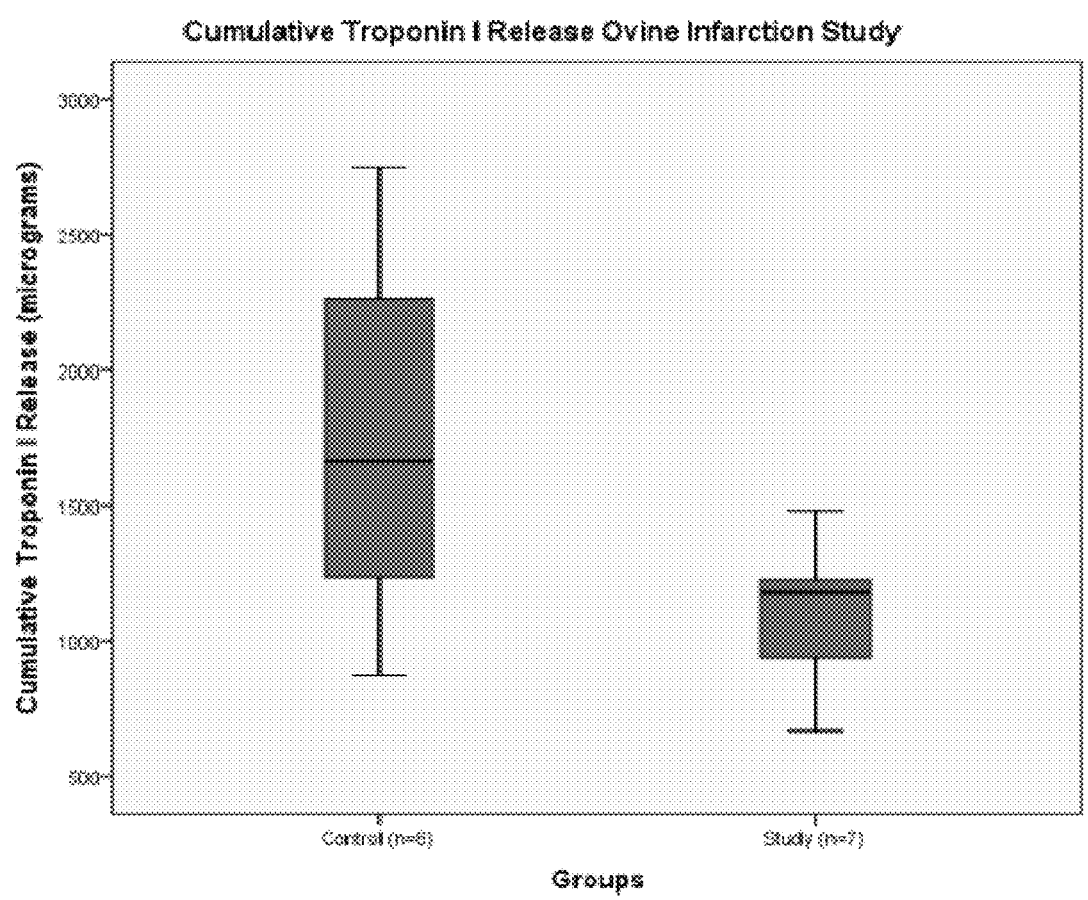
FIG. 12 shows the cumulative troponin I release in sheep undergoing cardiac ischemia and receiving human BNPsp (17-26). Treated sheep had significantly lower cumulative troponin I release (P<0.01) compared with control.

Following this positive safety/tolerance profile, we then administered 500 ng/kg·min synthetic human BNPsp(17-26) to 7 sheep undergoing cardiac ischemia induced by coronary ligation. Importantly, when compared with control saline infusions, BNPsp(17-26) significantly reduced cumulative cardiac troponin I (P<0.01) release post-ischemia (FIG. 12).

Example 5

Analysis of BNPsp(17-26) Metabolites Formed In Vivo During Ischemia

In this Example, the degradation of human BNPsp(17-26) into metabolites was assessed. Two methods were used. In a first experimental, an ex vivo set up was used wherein 1 nM BNPsp(17-26) was infused, at the time of reperfusion after 40 min ischemia into an isolated rat heart. The system was set to recirculate the BNPsp(17-26) containing buffer so the peptide was exposed to ischemic tissue for more than one pass through the heart. A 10 ml sample of perfusate was collected after 20 minutes of recirculation, extracted on a Sep Pak C18 cartridge and purified by immunoaffinity purification and reverse phase HPLC. This purified material was then subjected to tandem MS/MS for precise identification. The second experimental was in vivo, wherein 3 ml of peripheral plasma from sheep receiving 500 ng/kg·min BNPsp(17-26) during cardiac ischemia was purified as for the ex vivo isolated rat heart perfusate and analysed on tandem MS/MS.

Figure 13:
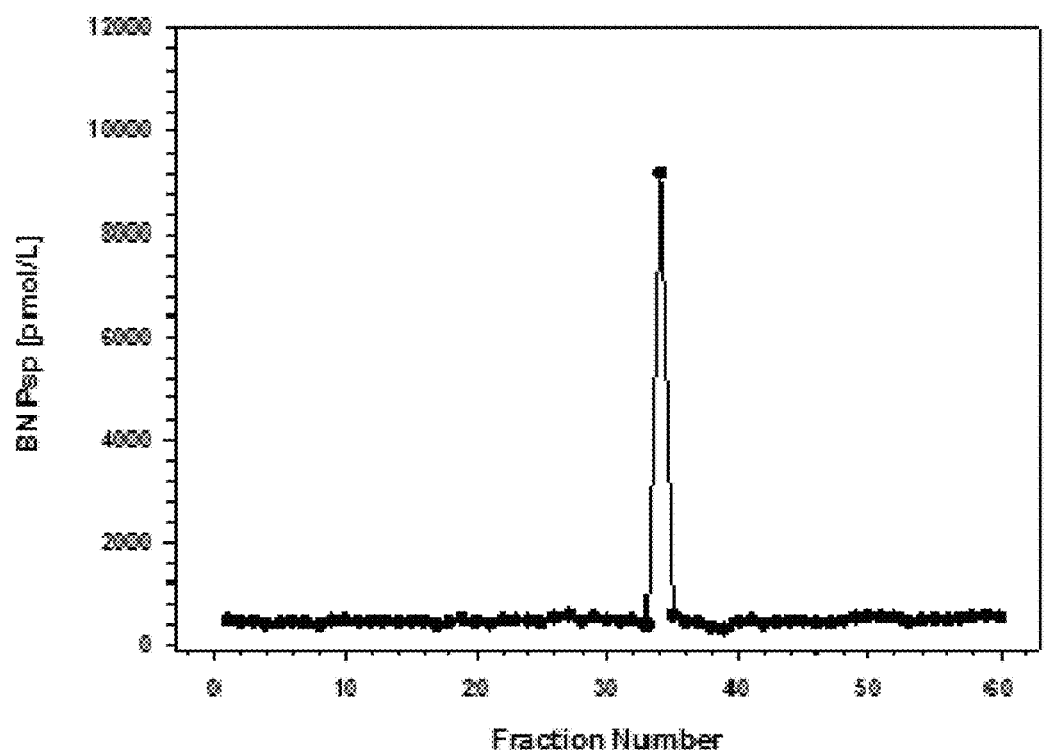
FIG. 13 shows the elution profile of proteolytically cleaved human BNPsp(18-26) that has been passed through either an ischemia isolated rat heart or in vivo sheep under cardiac coronary ligation. The elution position (fraction 34) is four fractions earlier than synthetic human BNPsp(17-26), indicated by the downward arrow.

These experiments assessed the degradation during ischemia of human BNPsp(17-26) to metabolites when passed through an isolated rat heart preparation or whole animal (sheep). In both setups, synthetic human BNPsp(17-26) was degraded to a smaller form, namely BNPsp(18-26), resulting from proteolytic cleavage of the amino terminal leucine. This is shown in FIG. 13. A single sharp peak resolved on RP-HPLC and was confirmed as human BNPsp(18-26) by tandem MS/MS. This indicates that the amino terminal end is most susceptible to initial degradation.

Example 6

Effect of Modifying the Amino Acid Sequence of BNPsp(17-26)

This set of experiments assessed modified BNPsp(17-26) peptides. This experiment repeated the preconditioning work outlined in the isolated rat heart model Examples, but with C-terminal ablated and an N-terminal extended version of BNPsp(17-26). Hearts were preconditioned with 30 minute doses of 0.3 nmol/L BNPsp(16-26) and BNPsp(17-24) prior to 40 minutes of global ischemia and 90 minutes reperfusion. Cardiac contractile and perfusion pressure indices were recorded.

Figure 14:
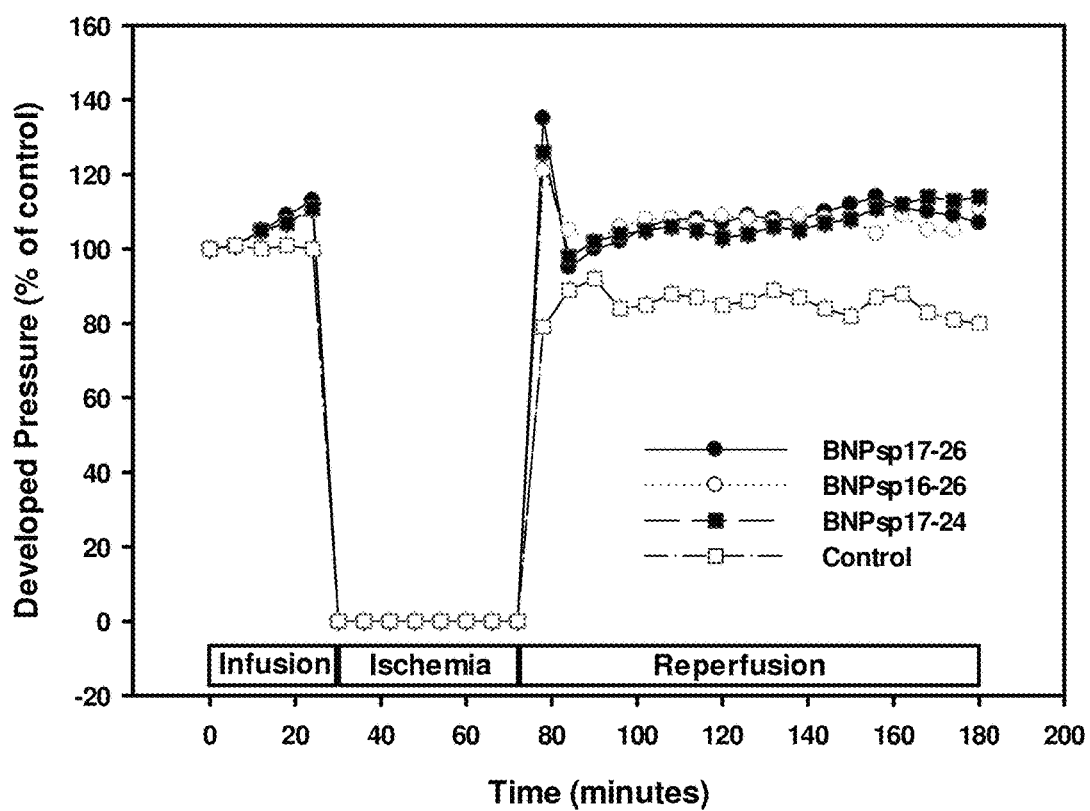
FIG. 14 shows the developed pressures in isolated perfused rat hearts receiving 0.3 nmol/L of altered BNPsp sequences (n=3 for each group).

Modification of the BNPsp(17-26) sequence in these initial experiments, either through N-terminal addition or C-terminal ablation, and the effects upon responses observed in isolated hearts are shown in FIG. 14. Importantly, the addition of phenylalanine (F) at position 16 to the N-terminus (thus creating BNPsp(16-26)) gave the same haemodynamic protective profile as BNPsp(17-26). A modified peptide with two C-terminal amino acids removed (i.e., BNPsp(17-24) also had a protective effect.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

We claim:

1. A method of treating a subject having or at risk for developing a cardiovascular disorder, comprising increasing Type-B natriuretic signal peptide fragment activity in said subject by administering to the subject a composition comprising a substantially pure Type-B natriuretic signal peptide fragment, wherein the amino acid sequence of said Type-B natriuretic signal peptide fragment consists of an amino acid sequence selected from one of SEQ ID NOS: 1 to 9.

2. A method according to claim 1, wherein the cardiovascular disorder is an acute coronary syndrome selected from the group consisting of ST-segment elevation myocardial infarction, non-ST-segment elevation myocardial infarction and unstable angina.

3. A method according to claim 1, wherein the composition comprises about 0.01 to about 100 milligrams of said Type-B natriuretic signal peptide fragment.

4. A method according to claim 1, wherein the subject is a mammal.

5. A method according to claim 1, wherein the amino acid sequence of the Type-B natriuretic signal peptide fragment consists of LHLAFLGGRS (SEQ ID NO: 1).

6. A method according to claim 1, wherein the subject is a human.

7. A method according to claim 6, wherein the amino acid sequence of the Type-B natriuretic signal peptide fragment consists of LHLAFLGGRS (SEQ ID NO: 1).

8. A method of treating a subject having or at risk for developing an acute coronary syndrome, comprising administering to the subject a composition comprising a Type-B natriuretic signal peptide fragment, wherein the amino acid sequence of said Type-B natriuretic signal peptide fragment consists of an amino acid sequence selected from one of SEQ ID NOS: 1 to 9.

9. A method according to claim 8, wherein the cardiovascular disorder is an acute coronary syndrome selected from the group consisting of ST-segment elevation myocardial infarction, non-ST-segment elevation myocardial infarction and unstable angina.

10. A method according to claim 8, wherein the composition comprises about 0.01 to about 100 milligrams of said Type-B natriuretic signal peptide fragment.

11. A method according to claim 8, wherein the amino acid sequence of the Type-B natriuretic signal peptide fragment consists of LHLAFLGGRS (SEQ ID NO: 1).

12. A method according to claim 8, wherein the subject is a mammal.

13. A method according to claim 12, wherein the subject is a human.

14. A method according to claim 13, wherein the amino acid sequence of the Type-B natriuretic signal peptide fragment consists of LHLAFLGGRS (SEQ ID NO: 1).

* * * * *

SEQUENCE LISTING

```
<160> NUMBER OF SEQ ID NOS: 19

<210> SEQ ID NO 1
<211> LENGTH: 10
<212> TYPE: PRT
<213> ORGANISM: Homo sapiens

<400> SEQUENCE: 1

Leu His Leu Ala Phe Leu Gly Gly Arg Ser
1               5                   10

<210> SEQ ID NO 2
<211> LENGTH: 9
```

```
<212> TYPE: PRT
<213> ORGANISM: Homo sapiens

<400> SEQUENCE: 2

Leu His Leu Ala Phe Leu Gly Gly Arg
1               5

<210> SEQ ID NO 3
<211> LENGTH: 8
<212> TYPE: PRT
<213> ORGANISM: Homo sapiens

<400> SEQUENCE: 3

Leu His Leu Ala Phe Leu Gly Gly
1               5

<210> SEQ ID NO 4
<211> LENGTH: 7
<212> TYPE: PRT
<213> ORGANISM: Homo sapiens

<400> SEQUENCE: 4

Leu His Leu Ala Phe Leu Gly
1               5

<210> SEQ ID NO 5
<211> LENGTH: 6
<212> TYPE: PRT
<213> ORGANISM: Homo sapiens

<400> SEQUENCE: 5

Leu His Leu Ala Phe Leu
1               5

<210> SEQ ID NO 6
<211> LENGTH: 5
<212> TYPE: PRT
<213> ORGANISM: Homo sapiens

<400> SEQUENCE: 6

Leu His Leu Ala Phe
1               5

<210> SEQ ID NO 7
<211> LENGTH: 4
<212> TYPE: PRT
<213> ORGANISM: Homo sapiens

<400> SEQUENCE: 7

Leu His Leu Ala
1

<210> SEQ ID NO 8
<211> LENGTH: 3
<212> TYPE: PRT
<213> ORGANISM: Homo sapiens

<400> SEQUENCE: 8

Leu His Leu
1

<210> SEQ ID NO 9
<211> LENGTH: 2
<212> TYPE: PRT
<213> ORGANISM: Homo sapiens
```

```
<400> SEQUENCE: 9

Leu His
1

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine, Ile, Val, Met, Ala, Phe or Gly
<220> FEATURE:
<221> NAME/KEY: MOD_RES
<222> LOCATION: (4)..(4)
<223> OTHER INFORMATION: Val, Leu, Ile or Gly
<220> FEATURE:
<221> NAME/KEY: MOD_RES
<222> LOCATION: (5)..(5)
<223> OTHER INFORMATION: Leu, Val, Ile, Ala, Tyr or Gly
<220> FEATURE:
<221> NAME/KEY: MOD_RES
<222> LOCATION: (6)..(6)
<223> OTHER INFORMATION: Norleucine, Ile, Val, Met, Ala, Phe or Gly
<220> FEATURE:
<221> NAME/KEY: MOD_RES
<222> LOCATION: (7)..(8)
<223> OTHER INFORMATION: Pro, Ala, Arg or Ser
<220> FEATURE:
<221> NAME/KEY: MOD_RES
<222> LOCATION: (9)..(9)
<223> OTHER INFORMATION: Arg, Gln, Asn or Gly
<220> FEATURE:
<221> NAME/KEY: MOD_RES
<222> LOCATION: (10)..(10)
<223> OTHER INFORMATION: Thr or Gly
<220> FEATURE:
<223> OTHER INFORMATION: see specification as filed for detailed
      description of substitutions and preferred embodiments

<400> SEQUENCE: 10

Leu His Xaa Xaa Xaa Xaa Xaa Xaa Xaa Xaa
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine, Ile, Val, Met, Ala, Phe or Gly
<220> FEATURE:
<221> NAME/KEY: MOD_RES
<222> LOCATION: (4)..(4)
<223> OTHER INFORMATION: Val, Leu, Ile or Gly
<220> FEATURE:
<221> NAME/KEY: MOD_RES
<222> LOCATION: (5)..(5)
<223> OTHER INFORMATION: Leu, Val, Ile, Ala, Tyr or Gly
<220> FEATURE:
<221> NAME/KEY: MOD_RES
<222> LOCATION: (6)..(6)
<223> OTHER INFORMATION: Norleucine, Ile, Val, Met, Ala, Phe or Gly
<220> FEATURE:
<221> NAME/KEY: MOD_RES
<222> LOCATION: (7)..(8)
<223> OTHER INFORMATION: Pro, Ala, Arg or Ser
```

```
<220> FEATURE:
<221> NAME/KEY: MOD_RES
<222> LOCATION: (9)..(9)
<223> OTHER INFORMATION: Arg, Gln, Asn or Gly
<220> FEATURE:
<223> OTHER INFORMATION: see specification as filed for detailed
      description of substitutions and preferred embodiments

<400> SEQUENCE: 11

Leu His Xaa Xaa Xaa Xaa Xaa Xaa Xaa
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine, Ile, Val, Met, Ala, Phe or Gly
<220> FEATURE:
<221> NAME/KEY: MOD_RES
<222> LOCATION: (4)..(4)
<223> OTHER INFORMATION: Val, Leu, Ile or Gly
<220> FEATURE:
<221> NAME/KEY: MOD_RES
<222> LOCATION: (5)..(5)
<223> OTHER INFORMATION: Leu, Val, Ile, Ala, Tyr or Gly
<220> FEATURE:
<221> NAME/KEY: MOD_RES
<222> LOCATION: (6)..(6)
<223> OTHER INFORMATION: Norleucine, Ile, Val, Met, Ala, Phe or Gly
<220> FEATURE:
<221> NAME/KEY: MOD_RES
<222> LOCATION: (7)..(8)
<223> OTHER INFORMATION: Pro, Ala, Arg or Ser
<220> FEATURE:
<223> OTHER INFORMATION: see specification as filed for detailed
      description of substitutions and preferred embodiments

<400> SEQUENCE: 12

Leu His Xaa Xaa Xaa Xaa Xaa Xaa
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine, Ile, Val, Met, Ala, Phe or Gly
<220> FEATURE:
<221> NAME/KEY: MOD_RES
<222> LOCATION: (4)..(4)
<223> OTHER INFORMATION: Val, Leu, Ile or Gly
<220> FEATURE:
<221> NAME/KEY: MOD_RES
<222> LOCATION: (5)..(5)
<223> OTHER INFORMATION: Leu, Val, Ile, Ala, Tyr or Gly
<220> FEATURE:
<221> NAME/KEY: MOD_RES
<222> LOCATION: (6)..(6)
<223> OTHER INFORMATION: Norleucine, Ile, Val, Met, Ala, Phe or Gly
<220> FEATURE:
<221> NAME/KEY: MOD_RES
<222> LOCATION: (7)..(7)
<223> OTHER INFORMATION: Pro, Ala, Arg or Ser
<220> FEATURE:
```

<223> OTHER INFORMATION: see specification as filed for detailed
      description of substitutions and preferred embodiments

<400> SEQUENCE: 13

Leu His Xaa Xaa Xaa Xaa Xaa
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine, Ile, Val, Met, Ala, Phe or Gly
<220> FEATURE:
<221> NAME/KEY: MOD_RES
<222> LOCATION: (4)..(4)
<223> OTHER INFORMATION: Val, Leu, Ile or Gly
<220> FEATURE:
<221> NAME/KEY: MOD_RES
<222> LOCATION: (5)..(5)
<223> OTHER INFORMATION: Leu, Val, Ile, Ala, Tyr or Gly
<220> FEATURE:
<221> NAME/KEY: MOD_RES
<222> LOCATION: (6)..(6)
<223> OTHER INFORMATION: Norleucine, Ile, Val, Met, Ala, Phe or Gly
<220> FEATURE:
<223> OTHER INFORMATION: see specification as filed for detailed
      description of substitutions and preferred embodiments

<400> SEQUENCE: 14

Leu His Xaa Xaa Xaa Xaa
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine, Ile, Val, Met, Ala, Phe or Gly
<220> FEATURE:
<221> NAME/KEY: MOD_RES
<222> LOCATION: (4)..(4)
<223> OTHER INFORMATION: Val, Leu, Ile or Gly
<220> FEATURE:
<221> NAME/KEY: MOD_RES
<222> LOCATION: (5)..(5)
<223> OTHER INFORMATION: Leu, Val, Ile, Ala, Tyr or Gly
<220> FEATURE:
<223> OTHER INFORMATION: see specification as filed for detailed
      description of substitutions and preferred embodiments

<400> SEQUENCE: 15

Leu His Xaa Xaa Xaa
1               5

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (3)..(3)
<223> OTHER INFORMATION: Norleucine, Ile, Val, Met, Ala, Phe or Gly
<220> FEATURE:
<221> NAME/KEY: MOD_RES
<222> LOCATION: (4)..(4)
<223> OTHER INFORMATION: Val, Leu, Ile or Gly
<220> FEATURE:
<223> OTHER INFORMATION: see specification as filed for detailed
      description of substitutions and preferred embodiments

<400> SEQUENCE: 16

Leu His Xaa Xaa
1

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine, Ile, Val, Met, Ala, Phe or Gly
<220> FEATURE:
<223> OTHER INFORMATION: see specification as filed for detailed
      description of substitutions and preferred embodiments

<400> SEQUENCE: 17

Leu His Xaa
1

<210> SEQ ID NO 18
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp, Gly or Glu
<220> FEATURE:
<221> NAME/KEY: MOD_RES
<222> LOCATION: (3)..(3)
<223> OTHER INFORMATION: Pro or Leu
<220> FEATURE:
<221> NAME/KEY: MOD_RES
<222> LOCATION: (4)..(4)
<223> OTHER INFORMATION: Gln, Lys, Arg, Cys or Leu
<220> FEATURE:
<221> NAME/KEY: MOD_RES
<222> LOCATION: (5)..(5)
<223> OTHER INFORMATION: Thr, Lys, Met or Ala
<220> FEATURE:
<221> NAME/KEY: MOD_RES
<222> LOCATION: (6)..(6)
<223> OTHER INFORMATION: Ala or Val
<220> FEATURE:
<221> NAME/KEY: MOD_RES
<222> LOCATION: (7)..(7)
<223> OTHER INFORMATION: Pro or Leu
<220> FEATURE:
<221> NAME/KEY: MOD_RES
<222> LOCATION: (8)..(8)
<223> OTHER INFORMATION: Ser, Leu or Pro
<220> FEATURE:
<221> NAME/KEY: MOD_RES
<222> LOCATION: (9)..(9)
<223> OTHER INFORMATION: Arg or Gln
<220> FEATURE:
<221> NAME/KEY: MOD_RES
```

```
<222> LOCATION: (10)..(10)
<223> OTHER INFORMATION: Ala, Thr or Met
<220> FEATURE:
<221> NAME/KEY: MOD_RES
<222> LOCATION: (11)..(11)
<223> OTHER INFORMATION: Leu, Ile or Val
<220> FEATURE:
<221> NAME/KEY: MOD_RES
<222> LOCATION: (13)..(13)
<223> OTHER INFORMATION: Leu or Phe
<220> FEATURE:
<221> NAME/KEY: MOD_RES
<222> LOCATION: (18)..(18)
<223> OTHER INFORMATION: His, Asn or Tyr
<220> FEATURE:
<221> NAME/KEY: MOD_RES
<222> LOCATION: (20)..(20)
<223> OTHER INFORMATION: Ala or Ser
<220> FEATURE:
<221> NAME/KEY: MOD_RES
<222> LOCATION: (21)..(21)
<223> OTHER INFORMATION: Phe, Pro or Leu
<220> FEATURE:
<221> NAME/KEY: MOD_RES
<222> LOCATION: (24)..(24)
<223> OTHER INFORMATION: Gly or Cys
<220> FEATURE:
<221> NAME/KEY: MOD_RES
<222> LOCATION: (25)..(25)
<223> OTHER INFORMATION: Arg or His
<220> FEATURE:
<221> NAME/KEY: MOD_RES
<222> LOCATION: (26)..(26)
<223> OTHER INFORMATION: Ser or Pro

<400> SEQUENCE: 18

Met Xaa Xaa Xaa Xaa Xaa Xaa Xaa Xaa Xaa Xaa Leu Xaa Leu Leu Phe
1               5                   10                  15

Leu Xaa Leu Xaa Xaa Leu Gly Xaa Xaa Xaa
            20                  25

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Norleucine, Ile, Val, Met, Ala, Phe or Gly
<220> FEATURE:
<221> NAME/KEY: MOD_RES
<222> LOCATION: (4)..(4)
<223> OTHER INFORMATION: Val, Leu, Ile or Gly
<220> FEATURE:
<221> NAME/KEY: MOD_RES
<222> LOCATION: (5)..(5)
<223> OTHER INFORMATION: Leu, Val, Ile, Ala, Tyr or Gly
<220> FEATURE:
<221> NAME/KEY: MOD_RES
<222> LOCATION: (6)..(6)
<223> OTHER INFORMATION: Norleucine, Ile, Val, Met, Ala, Phe or Gly
<220> FEATURE:
<221> NAME/KEY: MOD_RES
<222> LOCATION: (7)..(8)
<223> OTHER INFORMATION: Pro, Ala, Arg or Ser
<220> FEATURE:
<221> NAME/KEY: MOD_RES
<222> LOCATION: (9)..(9)
<223> OTHER INFORMATION: Gln, Asn or Gly
<220> FEATURE:
<221> NAME/KEY: MOD_RES
<222> LOCATION: (10)..(10)
<223> OTHER INFORMATION: Ser, Thr or Gly
```

```
<220> FEATURE:
<223> OTHER INFORMATION: see specification as filed for detailed
      description of substitutions and preferred embodiments

<400> SEQUENCE: 19

Leu His Xaa Xaa Xaa Xaa Xaa Xaa Xaa Xaa
1               5                   10
```